US012039495B2

(12) United States Patent
Ward et al.

(10) Patent No.: US 12,039,495 B2
(45) **Date of Patent: *Jul. 16, 2024**

(54) SYSTEMS AND METHODS FOR CODING DATA FROM A MEDICAL ENCOUNTER

(71) Applicant: T-System, Inc., Dallas, TX (US)

(72) Inventors: James Ward, Plano, TX (US); Richard Wunnebuger, Westcliffe, CO (US); Stephen Hilliard, Richardson, TX (US); Hank Hikspoors, McKinney, TX (US)

(73) Assignee: T-System, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/351,824

(22) Filed: Jul. 13, 2023

(65) Prior Publication Data

US 2023/0368137 A1 Nov. 16, 2023

Related U.S. Application Data

(63) Continuation of application No. 16/121,591, filed on Sep. 4, 2018, now Pat. No. 11,783,291, which is a continuation of application No. 14/170,437, filed on Jan. 31, 2014, now Pat. No. 10,078,729.

(51) Int. Cl.

| | |
|---|---|
| ***G16H 10/60*** | (2018.01) |
| ***G06Q 10/10*** | (2023.01) |
| ***G16H 15/00*** | (2018.01) |
| ***G16H 30/00*** | (2018.01) |

(Continued)

(52) U.S. Cl.

CPC ............. *G06Q 10/10* (2013.01); *G16H 10/60* (2018.01); *G16H 15/00* (2018.01); *G16H 30/00* (2018.01);

(Continued)

(58) Field of Classification Search

CPC ............................... G16H 10/60; G16H 15/00

See application file for complete search history.

(56) References Cited

U.S. PATENT DOCUMENTS 7,379,885 B1 * 5/2008 Zakim .................... G16H 20/10 600/300

8,265,961 B2 9/2012 Callas (Continued)

FOREIGN PATENT DOCUMENTS

WO 2013116788 A1 8/2013

OTHER PUBLICATIONS

International Search Report and Written Opinion issued for PCT/US2015/013474, dated May 14, 201, 8 pages.

*Primary Examiner* — Mamon Obeid

*Assistant Examiner* — Chance L Smith

(74) *Attorney, Agent, or Firm* — BrownWinick Law Firm; Christopher A. Proskey

(57) ABSTRACT

In certain arrangements, systems and methods assist in gathering relevant data in a doctor-patient encounter for obtaining a properly specified diagnosis code. In one embodiment, selectable data items which are provided as part of a medical charting program may be correlated with one or more standardized diagnosis codes (e.g. ICD-10 codes). Upon selection of the appropriate data items when charting a patient encounter, one or more diagnosis codes which are correlated with the selected data items may be flagged and/or generated for later use, such as for filing a claim submission as part of a billing process or to further enhance the clinical workflow of patient encounter documentation.

28 Claims, 39 Drawing Sheets

(51) Int. Cl.

| | |
|---|---|
| ***G16H 40/20*** | (2018.01) |
| ***G16Z 99/00*** | (2019.01) |
| *G16H 70/00* | (2018.01) |
| *G16H 80/00* | (2018.01) |

(52) U.S. Cl.
CPC ............. *G16H 40/20* (2018.01); *G16Z 99/00* (2019.02); *G16H 70/00* (2018.01); *G16H 80/00* (2018.01)

(56) References Cited

U.S. PATENT DOCUMENTS

| | | | | |
|---|---|---|---|---|
| 8,510,129 | B2 | 8/2013 | Morris | |
| 2002/0087358 | A1* | 7/2002 | Gilbert ................... | G16H 50/20 705/2 |
| 2003/0046111 | A1 | 3/2003 | Snitkin | |
| 2005/0131738 | A1 | 6/2005 | Morris | |
| 2005/0273363 | A1* | 12/2005 | Lipscher ................ | G06Q 10/06 705/2 |
| 2008/0319942 | A1 | 12/2008 | Courdy et al. | |
| 2009/0125850 | A1* | 5/2009 | Karstens ............... | G06F 3/0481 715/866 |
| 2010/0094657 | A1 | 4/2010 | Stern et al. | |
| 2010/0305969 | A1 | 12/2010 | Bacon | |
| 2011/0119309 | A1 | 5/2011 | Aronson | |
| 2011/0238441 | A1* | 9/2011 | Callas .................... | G06Q 40/08 705/2 |
| 2015/0106111 | A1 | 4/2015 | Gray | |
| 2015/0356646 | A1* | 12/2015 | Spitznagel ............. | G16H 40/20 705/2 |
| 2016/0012187 | A1* | 1/2016 | Zasowski ............... | G16H 40/60 705/3 |

* cited by examiner

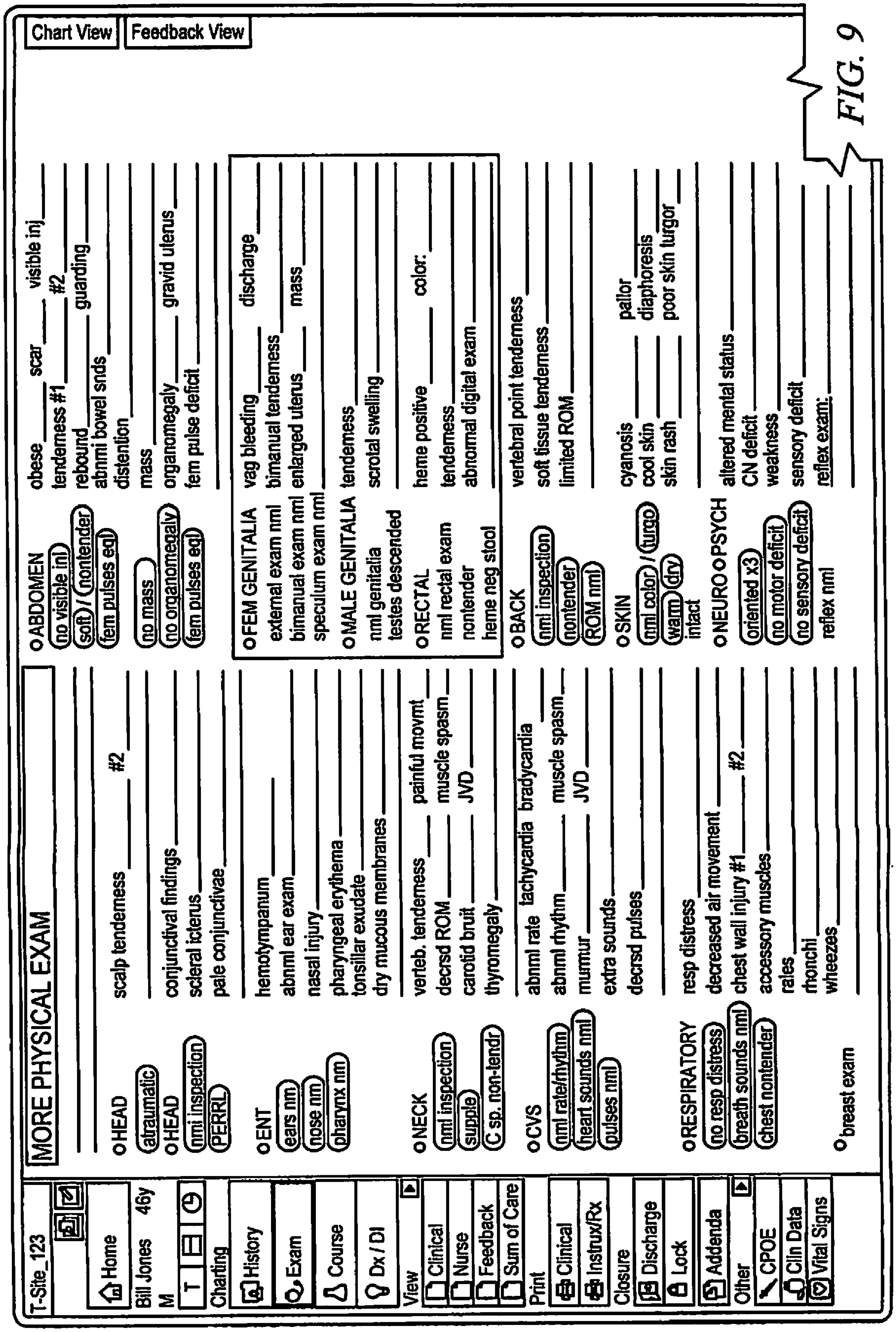

FIG. 9

MORE PHYSICAL EXAM

- ○ HEAD
  - (atraumatic) scalp tenderness _____ #2 _____
- ○ HEAD
  - (nml inspection) conjunctival findings _____
  - (PERRL) scleral icterus _____
  - pale conjunctivae _____
- ○ ENT
  - hemotympanum _____
  - (ears nml) abnml ear exam _____
  - (nose nml) nasal injury _____
  - (pharynx nml) pharyngeal erythema _____
  - tonsillar exudate _____
  - dry mucous membranes _____
- ○ NECK
  - (nml inspection) verteb. tenderness _____ painful movmt _____
  - (supple) decrsd ROM _____ muscle spasm _____
  - (C sp. non-tendr) carotid bruit _____ JVD _____
  - thyromegaly _____
- ○ CVS
  - (nml rate/rhythm) abnml rate _____ tachycardia _____ bradycardia _____
  - (heart sounds nml) abnml rhythm _____ muscle spasm _____
  - (pulses nml) murmur _____ JVD _____
  - extra sounds _____
  - decrsd pulses _____
- ○ RESPIRATORY
  - (no resp distress) resp distress _____
  - (breath sounds nml) decreased air movement _____
  - (chest nontender) chest wall injury #1 _____ #2 _____
  - accessory muscles _____
  - rales _____
  - rhonchi _____
  - wheezes _____
- ○ breast exam _____

- ○ ABDOMEN
  - (no visible inj) obese _____ scar _____ visible inj _____
  - (soft / nontender) tenderness #1 _____ #2 _____
  - (fem pulses eql) rebound _____ guarding _____
  - abnml bowel snds _____
  - distention _____
  - (no mass) mass _____
  - (no organomegaly) organomegaly _____ gravid uterus _____
  - (fem pulses eql) fem pulse deficit _____
- ○ FEM GENITALIA
  - external exam nml vag bleeding _____ discharge _____
  - bimanual exam nml bimanual tenderness _____
  - speculum exam nml enlarged uterus _____ mass _____
- ○ MALE GENITALIA
  - nml genitalia tenderness _____
  - testes descended scrotal swelling _____
- ○ RECTAL
  - nml rectal exam heme positive _____ color: _____
  - nontender tenderness _____
  - heme neg stool abnormal digital exam _____
- ○ BACK
  - (nml inspection) vertebral point tenderness _____
  - (nontender) soft tissue tenderness _____
  - (ROM nml) limited ROM _____
- ○ SKIN
  - (nml color) / (turgo) cyanosis _____ pallor _____
  - (warm) (dry) cool skin _____ diaphoresis _____
  - intact skin rash _____ poor skin turgor _____
- ○ NEURO ○ PSYCH
  - (oriented x3) altered mental status _____
  - (no motor deficit) CN deficit _____
  - (no sensory deficit) weakness _____
  - reflex nml sensory deficit _____
  - reflex exam: _____

Chart View | Feedback View

T-Site_123
Bill Jones 46y
M
Charting
- History
- Exam
- Course
- Dx / DI
View
- Clinical
- Nurse
- Feedback
- Sum of Care
Print
- Clinical
- Instrux/Rx
Closure
- Discharge
- Lock
Other
- Addenda
- CPOE
- Clin Data
- Vital Signs
Home

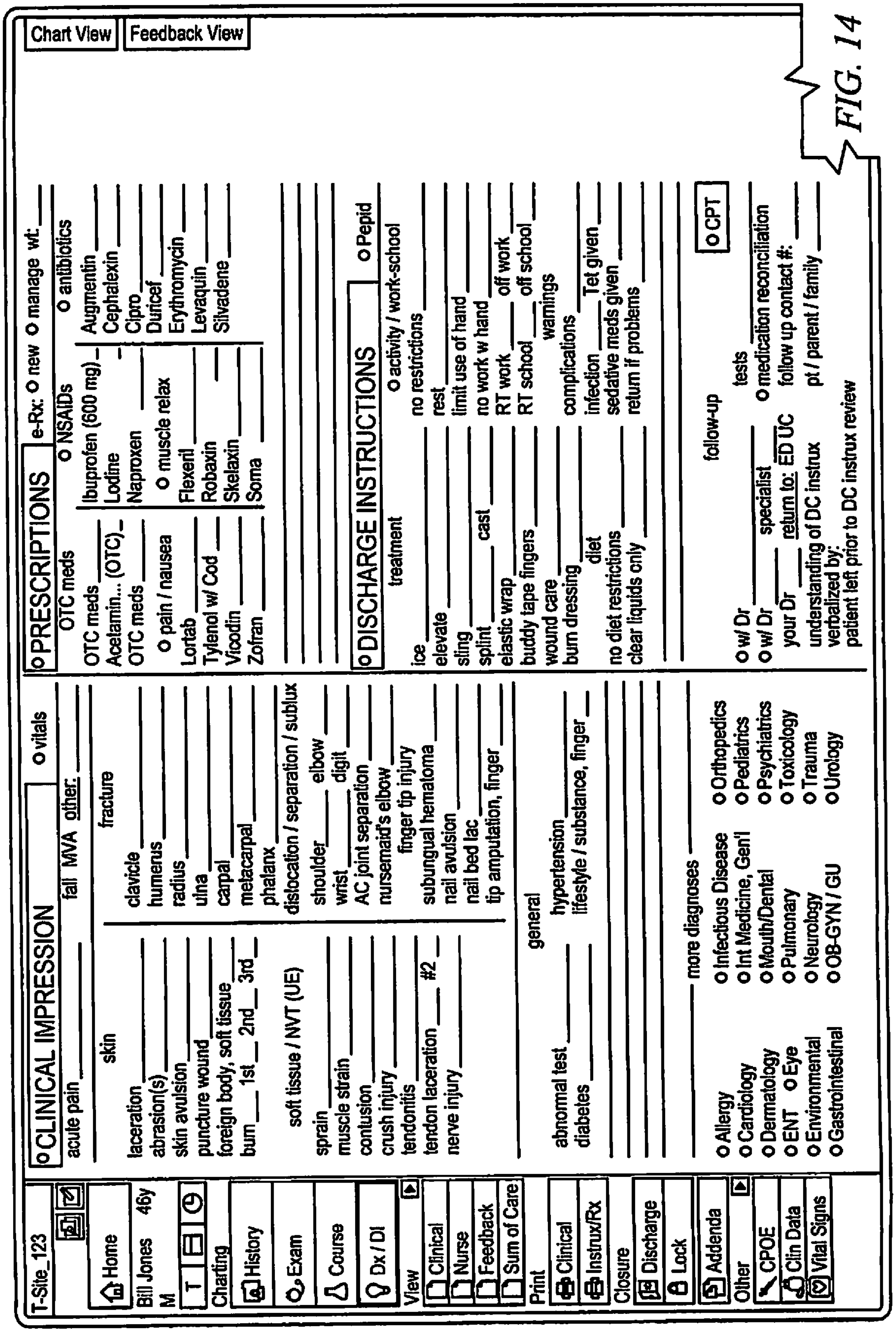

FIG. 14

T-Site_123 | Chart View | Feedback View

Bill Jones 46y
M  T

Charting
- Home
- History
- Exam
- Course
- Dx / DI

View
- Clinical
- Nurse
- Feedback
- Sum of Care

Print
- Clinical
- Instrux/Rx

Closure
- Discharge
- Lock

Other
- Addenda

- CPOE
- Clin Data
- Vital Signs

○ CLINICAL IMPRESSION                    ○ vitals acute pain _____ fall  MVA  other: _____
          _____  fracture _____ skin
- laceration _____         clavicle _____
- abrasion(s) _____        humerus _____
- skin avulsion _____      radius _____
- puncture wound _____     ulna _____
- foreign body, soft tissue _____  carpal _____
- burn ___ 1st ___ 2nd ___ 3rd ___ metacarpal _____
                                   phalanx _____ soft tissue / NVT (UE)   dislocation / separation / sublux
- sprain _____               shoulder _____ elbow _____
- muscle strain _____        wrist _____ digit _____
- contusion _____            AC joint separation _____
- crush injury _____         nursemaid's elbow _____
- tendonitis _____           finger tip injury _____
- tendon laceration _____ #2 _____  subungual hematoma _____
- nerve injury _____         nail avulsion _____
                             nail bed lac _____
                             tip amputation, finger _____ general
- abnormal test _____        hypertension _____
- diabetes _____             lifestyle / substance, finger _____

— more diagnoses —
- ○ Allergy          ○ Infectious Disease  ○ Orthopedics
- ○ Cardiology       ○ Int Medicine, Gen'l ○ Pediatrics
- ○ Dermatology      ○ Mouth/Dental        ○ Psychiatrics
- ○ ENT  ○ Eye       ○ Pulmonary           ○ Toxicology
- ○ Environmental    ○ Neurology           ○ Trauma
- ○ Gastrointestinal ○ OB-GYN / GU         ○ Urology ○ PRESCRIPTIONS  e-Rx: ○ new  ○ manage wt: _____

OTC meds _____        ○ NSAIDs _____       ○ antibiotics
Acetamin... (OTC) _____  Ibuprofen (600 mg) _____  Augmentin _____
OTC meds _____        Lodine _____         Cephalexin _____
                      Naproxen _____       Cipro _____
○ pain / nausea       ○ muscle relax       Duricef _____
Lortab _____          Flexeril _____       Erythromycin _____
Tylenol w/ Cod _____  Robaxin _____        Levaquin _____
Vicodin _____         Skelaxin _____       Silvadene _____
Zofran _____          Soma _____

○ DISCHARGE INSTRUCTIONS                    ○ Pepid treatment                    ○ activity / work-school
- ice _____                      no restrictions _____
- elevate _____                  rest _____
- sling _____                    limit use of hand _____
- splint _____ cast _____        no work w hand _____
- elastic wrap _____             RT work _____ off work _____
- buddy tape fingers _____       RT school _____ off school _____
- wound care _____                     warnings
- burn dressing _____            complications _____
            diet _____           infection _____ Tet given _____
- no diet restrictions _____     sedative meds given _____
- clear liquids only _____       return if problems _____ follow-up
- ○ w/ Dr _____                  tests _____
- ○ w/ Dr _____  specialist _____  ○ medication reconciliation
  your Dr _____  return to: ED UC   follow up contact #: _____
  understanding of DC instrux        pt / parent / family _____
  verbalized by: _____
  patient left prior to DC instrux review                ○ CPT

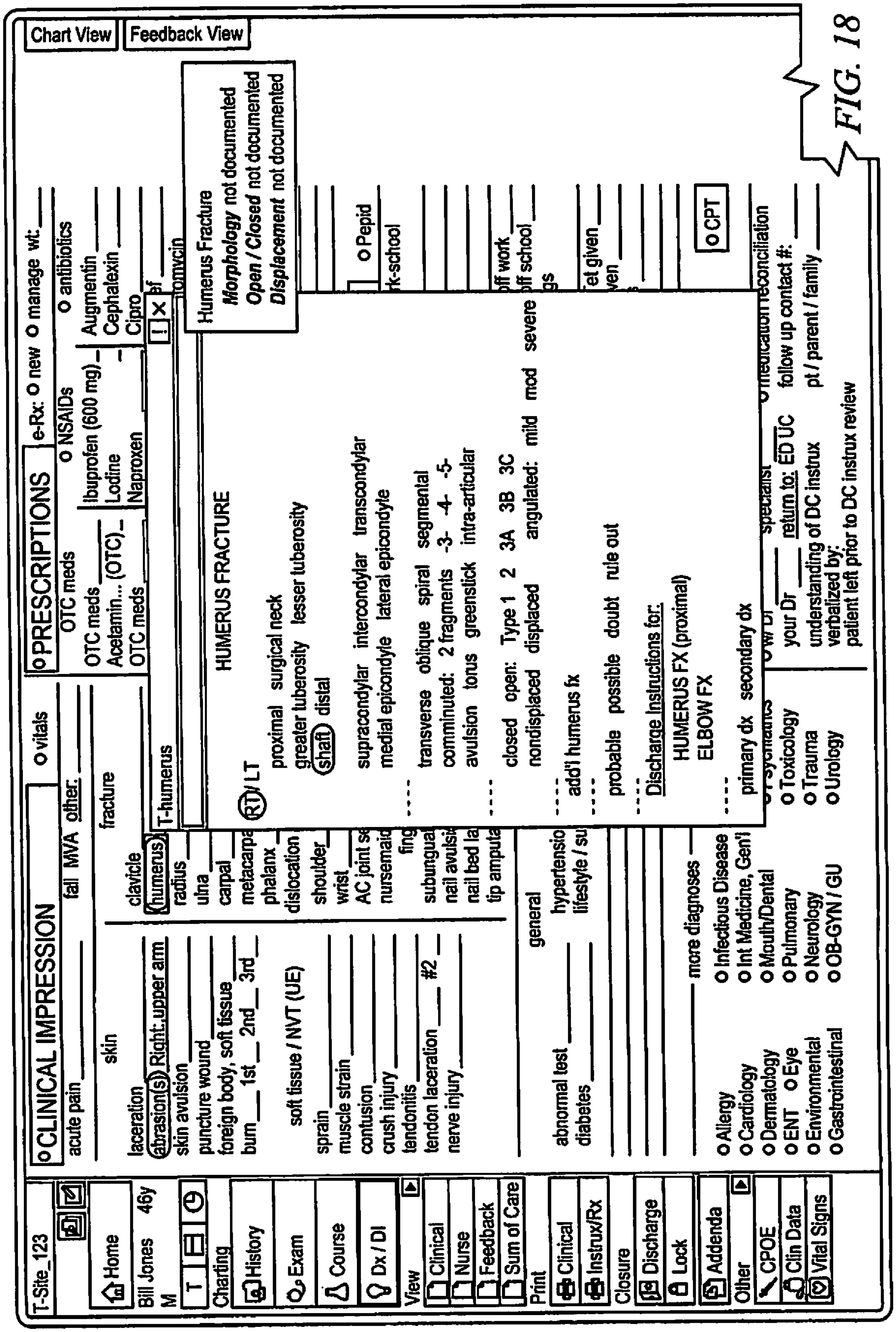

FIG. 18

[Rotated screenshot of a clinical charting interface]

Left sidebar:
- T-Site_123
- Home — Bill Jones, 46y, M
- Charting: History, Exam, Course, Dx / DI
- View: Clinical, Nurse, Feedback, Sum of Care
- Print: Clinical, Instrux/Rx
- Closure: Discharge, Lock
- Other: Addenda
- CPOE, Clin Data, Vital Signs ○ CLINICAL IMPRESSION          ○ vitals
acute pain ____
         fall  MVA  other: ____
skin ____                    fracture
laceration ____              clavicle
abrasion(s) Right: upper arm   [humerus]   T-humerus
skin avulsion ____           radius
puncture wound ____          ulna
foreign body, soft tissue ____   carpal
burn ___ 1st ___ 2nd ___ 3rd ___   metacarpa
                             phalanx
soft tissue / NVT (UE)       dislocation
sprain ____                  shoulder ____
muscle strain ____           wrist ____
contusion ____               AC joint se
crush injury ____            nursemaid
tendonitis ____                    fing
tendon laceration ____ #2    subungua
nerve injury ____            nail avulsi
                             nail bed la
                             tip amputa
                general ____
                hypertensio
                lifestyle / su
        — more diagnoses —
○ Allergy              ○ Infectious Disease
○ Cardiology           ○ Int Medicine, Gen'l
○ Dermatology          ○ Mouth/Dental
○ ENT   ○ Eye          ○ Pulmonary
○ Environmental        ○ Neurology
○ Gastrointestinal     ○ OB-GYN / GU ○ PRESCRIPTIONS   e-Rx: ○ new  ○ manage wt: ____
OTC meds          ○ NSAIDs          ○ antibiotics
OTC meds ____     Ibuprofen (600 mg) ____   Augmentin ____
Acetamin... (OTC) ____   Lodine ____        Cephalexin ____
OTC meds ____     Naproxen ____     Cipro ____
                                    ____omycin
                                    [ ]×__of____

HUMERUS FRACTURE         Humerus Fracture
                         *Morphology* not documented
RT / LT                  Open / Closed not documented
                         Displacement not documented
proximal  surgical neck
greater tuberosity  lesser tuberosity
(shaft)  distal supracondylar  intercondylar  transcondylar
medial epicondyle  lateral epicondyle transverse  oblique  spiral  segmental
comminuted: 2 fragments  -3-  -4-  -5-
avulsion  torus  greenstick  intra-articular closed  open: Type 1  2  3A  3B  3C
nondisplaced  displaced    angulated: mild  mod  severe
                                                        ○ Pepid
probable  possible  doubt  rule out                     rk-school Discharge Instructions for:                             off work
HUMERUS FX (proximal)                                   off school
ELBOW FX                                                gs primary dx  secondary dx                                et given
○ Toxicology                                            ven
○ Trauma
○ Urology                                               ○ CPT specialist ____       ○ medication reconciliation
your Dr ____   return to: EDUC    follow up contact #: ____
       understanding of DC instrux      pt / parent / family
       verbalized by: ____
       patient left prior to DC instrux review Chart View | Feedback View

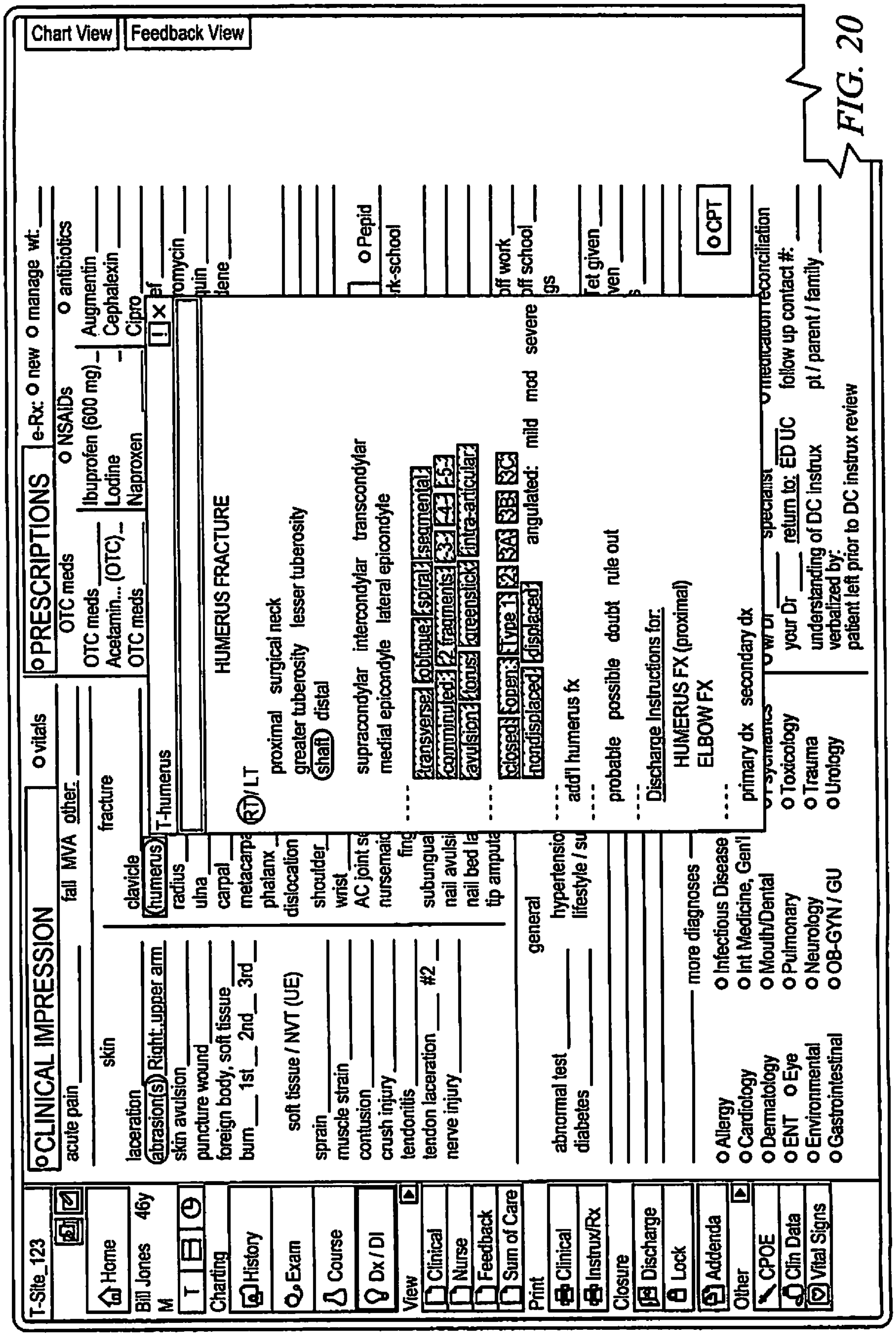

FIG. 20

[Chart View] [Feedback View]

T-Site_123
Bill Jones 46y
M

Charting
- Home
- History
- Exam
- Course
- Dx / DI

View
- Clinical
- Nurse
- Feedback
- Sum of Care

Print
- Clinical
- Instrux/Rx

Closure
- Discharge
- Lock
- Addenda

Other
- CPOE
- Clin Data
- Vital Signs

○ CLINICAL IMPRESSION ___ ○ vitals ___ ○ PRESCRIPTIONS ___ e-Rx: ○ new ○ manage wt: ___
acute pain ___ fall MVA other: ___ OTC meds ○ NSAIDs ○ antibiotics
skin ___ fracture ___ OTC meds Ibuprofen (600 mg) ___ Augmentin ___
laceration ___ clavicle ___ Acetamin... (OTC) ___ Lodine ___ Cephalexin ___
abrasion(s) Right: upper arm (humerus) T-humerus OTC meds ___ Naproxen ___ Cipro ___
skin avulsion ___ radius ___ □ x af
puncture wound ___ ulna ___ HUMERUS FRACTURE romycin ___
foreign body, soft tissue ___ carpal ___ quin ___
burn ___ 1st ___ 2nd ___ 3rd ___ metacarpa ___ dene ___
soft tissue / NVT (UE) phalanx ___ proximal  surgical neck
sprain ___ dislocation greater tuberosity  lesser tuberosity ○ Pepcid ___
muscle strain ___ shoulder shaft  distal rk-school ___
contusion ___ wrist (RT)/ LT
crush injury ___ AC joint s supracondylar  intercondylar  transcondylar
tendonitis ___ nursemaid medial epicondyle  lateral epicondyle
tendon laceration ___ #2 ___ fing Transverse Oblique Spiral 3 segmental
nerve injury ___ subungua Comminuted 3  2 fragments  3  4  5
nail avulsi Avulsion 3 torus greenstick Intra-articular off work ___
nail bed la Closed Open 3 Type 1 2 3A 3B 3C off school ___
tip amputa Nondisplaced displaced angulated: mild mod severe gs ___
general add'l humerus fx et given ___
abnormal test ___ hypertensio ven ___
diabetes ___ lifestyle / su probable  possible  doubt  rule out s ___
 Discharge Instructions for:
more diagnoses HUMERUS FX (proximal)
○ Allergy ○ Infectious Disease ELBOW FX ○ CPT
○ Cardiology ○ Int Medicine, Gen'l primary dx   secondary dx
○ Dermatology ○ Mouth/Dental ow D specialist ___ medication reconciliation
○ ENT ○ Eye ○ Pulmonary ○ Toxicology your Dr ___ return to: ED UC  follow up contact #: ___
○ Environmental ○ Neurology ○ Trauma understanding of DC instrux pt / parent / family ___
○ Gastrointestinal ○ OB-GYN / GU ○ Urology verbalized by: ___
patient left prior to DC instrux review

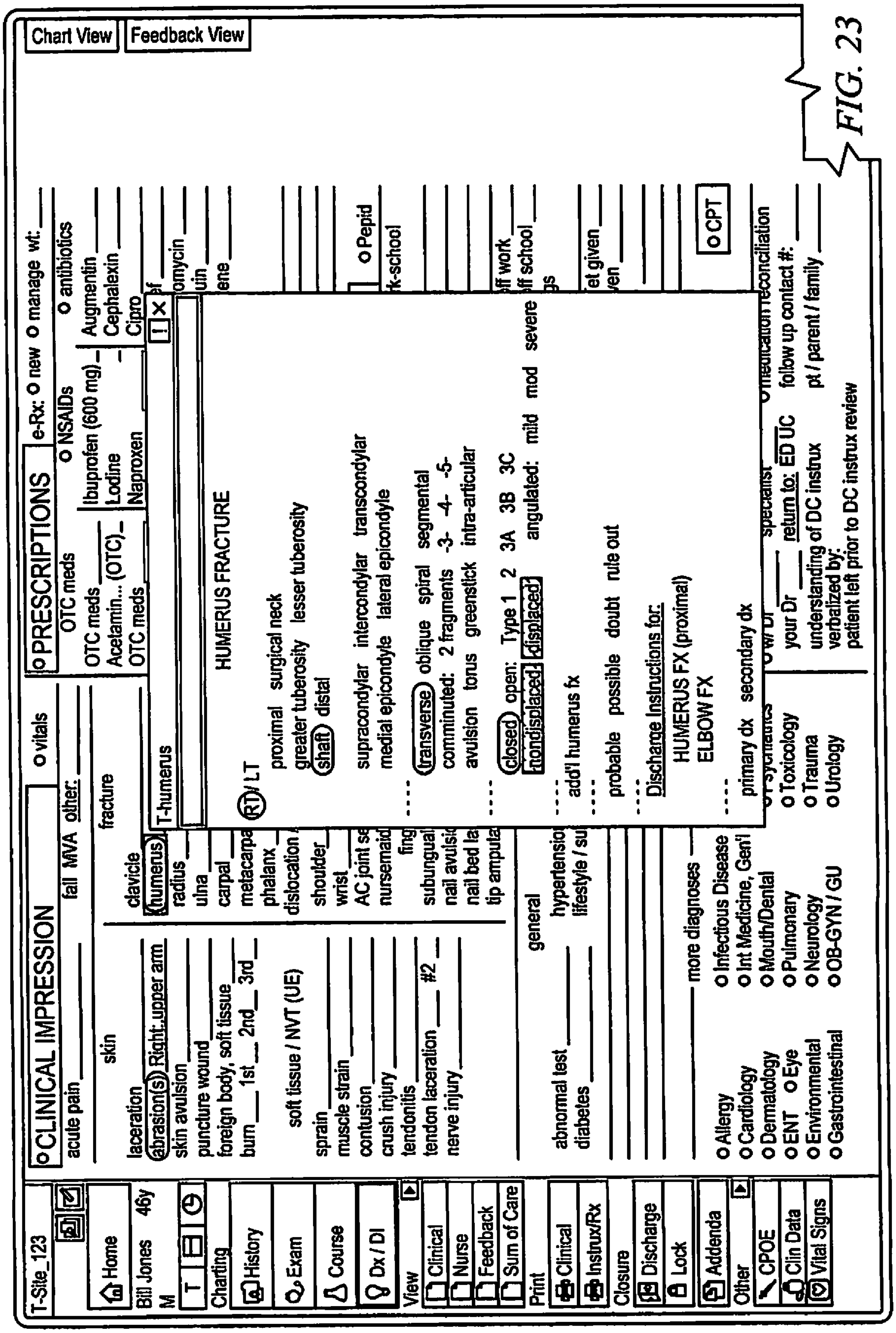

FIG. 23

T-Site_123
Home
Bill Jones   46y
M   T □ ⊕
Charting
History
Exam
Course
Dx / DI
View
Clinical
Nurse
Feedback
Sum of Care
Print
Clinical
Instrux/Rx
Closure
Discharge
Lock
Addenda
Other
CPOE
Clin Data
Vital Signs

| Chart View | Feedback View |

○ CLINICAL IMPRESSION   ○ vitals   e-Rx: ○ new  ○ manage wt: ___
acute pain   fall MVA other: ___   ○ PRESCRIPTIONS   ○ antibiotics
skin   fracture   OTC meds   Ibuprofen (600 mg) __ Augmentin ___
laceration ___   clavicle   Acetamin... (OTC) __ Lodine   Cephalexin ___
abrasion(s) Right: upper arm   (Humerus)   OTC meds ___ Naproxen   Cipro ___
skin avulsion ___   radius   T-humerus   ___omycin ___
puncture wound ___   ulna   □ ✕   ___uin ___
foreign body, soft tissue ___   carpal   HUMERUS FRACTURE   ___ene ___
burn ___ 1st __ 2nd __ 3rd __   metacarpal
soft tissue / NVT (UE)   phalanx   (RT)/ LT
sprain ___   dislocation   proximal  surgical neck   ○ Pepcid ___
muscle strain ___   shoulder ___   greater tuberosity  lesser tuberosity
contusion ___   wrist ___   shaft  distal   ___k-school
crush injury ___   AC joint se___
tendonitis ___   nursemaid ___   supracondylar  intercondylar  transcondylar
tendon laceration ___ #2 ___   fing___   medial epicondyle  lateral epicondyle
nerve injury ___   subungual ___
   nail avulsi___   transverse  oblique  spiral  segmental   ___ff work
   nail bed la___   comminuted:  2 fragments  -3-  -4-  -5-   ___ff school
   tip amputa___   avulsion  torus  greenstick  intra-articular   ___et given
general ___   hypertensio___   closed  open:  Type 1  2  3A  3B  3C   ___ven
abnormal test ___   lifestyle / su___   nondisplaced displaced  angulated:  mild  mod  severe
diabetes ___
   add'l humerus fx
— more diagnoses —
○ Allergy   ○ Infectious Disease   probable  possible  doubt  rule out
○ Cardiology   ○ Int Medicine, Gen'l   Discharge Instructions for:
○ Dermatology   ○ Mouth/Dental   HUMERUS FX (proximal)
○ ENT  ○ Eye   ○ Pulmonary   ELBOW FX
○ Environmental   ○ Neurology
○ Gastrointestinal   ○ OB-GYN / GU   primary dx   secondary dx ○ Toxicology   specialist ___   ○ medication reconciliation
   ○ Trauma   return to: EDUC   follow up contact #: ___
   ○ Urology   your Dr ___   pt / parent / family ___
      understanding of DC instrux   □ CPT
      verbalized by: ___
      patient left prior to DC instrux review

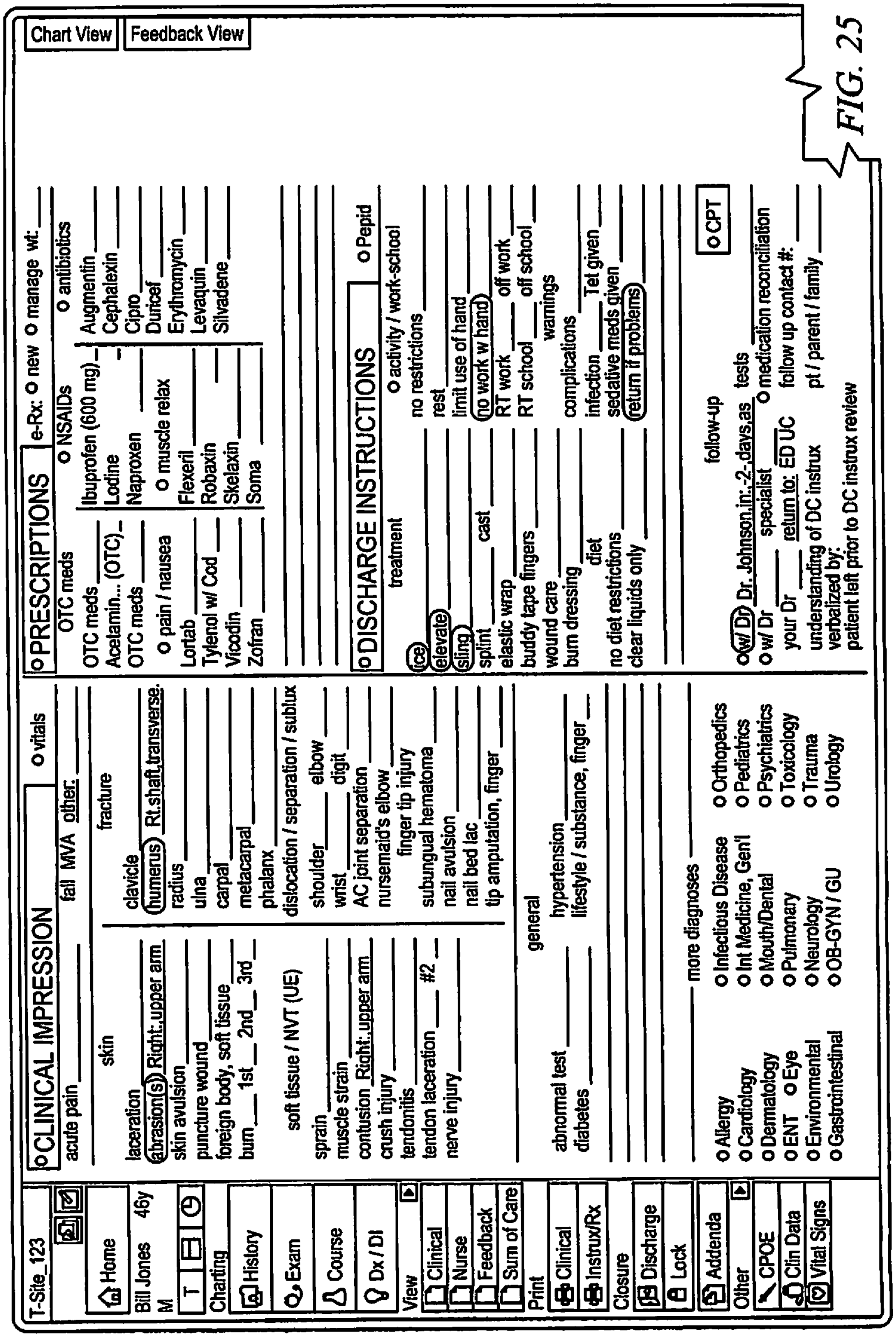

FIG. 25

T-Site_123

Home
Bill Jones  46y
M
Charting
- History
- Exam
- Course
- Dx / DI

View
- Clinical
- Nurse
- Feedback
- Sum of Care

Print
- Clinical
- Instrux/Rx

Closure
- Discharge
- Lock

Addenda
Other
CPOE
Clin Data
Vital Signs

Chart View | Feedback View

○ CLINICAL IMPRESSION          ○ vitals acute pain _____ fall MVA other: _____ skin
laceration _____
(abrasion(s)) Right: upper arm _____
skin avulsion _____
puncture wound _____
foreign body, soft tissue _____
burn ___ 1st ___ 2nd ___ 3rd ___ fracture
clavicle _____
(humerus) Rt.shaft,transverse _____
radius _____
ulna _____
carpal _____
metacarpal _____
phalanx _____
dislocation / separation / subluxation
shoulder _____ elbow _____
wrist _____ digit _____
AC joint separation _____
nursemaid's elbow _____
finger tip injury _____
subungual hematoma _____
nail avulsion _____
nail bed lac _____
tip amputation, finger _____ soft tissue / NVT (UE)
sprain _____
muscle strain _____
contusion Right: upper arm _____
crush injury _____
tendonitis _____
tendon laceration ___ #2 _____
nerve injury _____ general
hypertension _____
lifestyle / substance, finger _____
abnormal test _____
diabetes _____

— more diagnoses —
○ Allergy            ○ Infectious Disease   ○ Orthopedics
○ Cardiology         ○ Int Medicine, Gen'l  ○ Pediatrics
○ Dermatology        ○ Mouth/Dental         ○ Psychiatrics
○ ENT  ○ Eye         ○ Pulmonary            ○ Toxicology
○ Environmental      ○ Neurology            ○ Trauma
○ Gastrointestinal   ○ OB-GYN / GU          ○ Urology ○ PRESCRIPTIONS   e-Rx: ○ new ○ manage wt:___

OTC meds           ○ NSAIDs        ○ antibiotics
OTC meds           Ibuprofen (600 mg) _____ Augmentin _____
Acetamin...(OTC) _____ Lodine _____ Cephalexin _____
OTC meds           Naproxen _____ Cipro _____
                                    Duricef _____
○ pain / nausea   ○ muscle relax   Erythromycin _____
Lortab _____     Flexeril _____  Levaquin _____
Tylenol w/ Cod _____ Robaxin _____ Silvadene _____
Vicodin _____    Skelaxin _____
Zofran _____     Soma _____

○ DISCHARGE INSTRUCTIONS          ○ Pepcid treatment                 ○ activity / work-school
                          no restrictions _____
(ice)                     rest _____
(elevate)                 limit use of hand _____
(sling)                   (no work w hand) _____
splint ___ cast ___       RT work ___ off work ___
elastic wrap _____      RT school ___ off school ___
buddy tape fingers _____     warnings
wound care _____        complications _____
burn dressing _____     infection ___ Tet given ___
         diet             sedative meds given _____
no diet restrictions _____  (return if problems)
clear liquids only _____ follow-up
○ w/ Dr Dr. Johnson in: 2 days as tests _____           ○ CPT
○ w/ Dr _____ specialist ___ ○ medication reconciliation
your Dr _____ return to: ED UC follow up contact #: _____
understanding of DC instrux _____ pt / parent / family
verbalized by: _____
patient left prior to DC instrux review

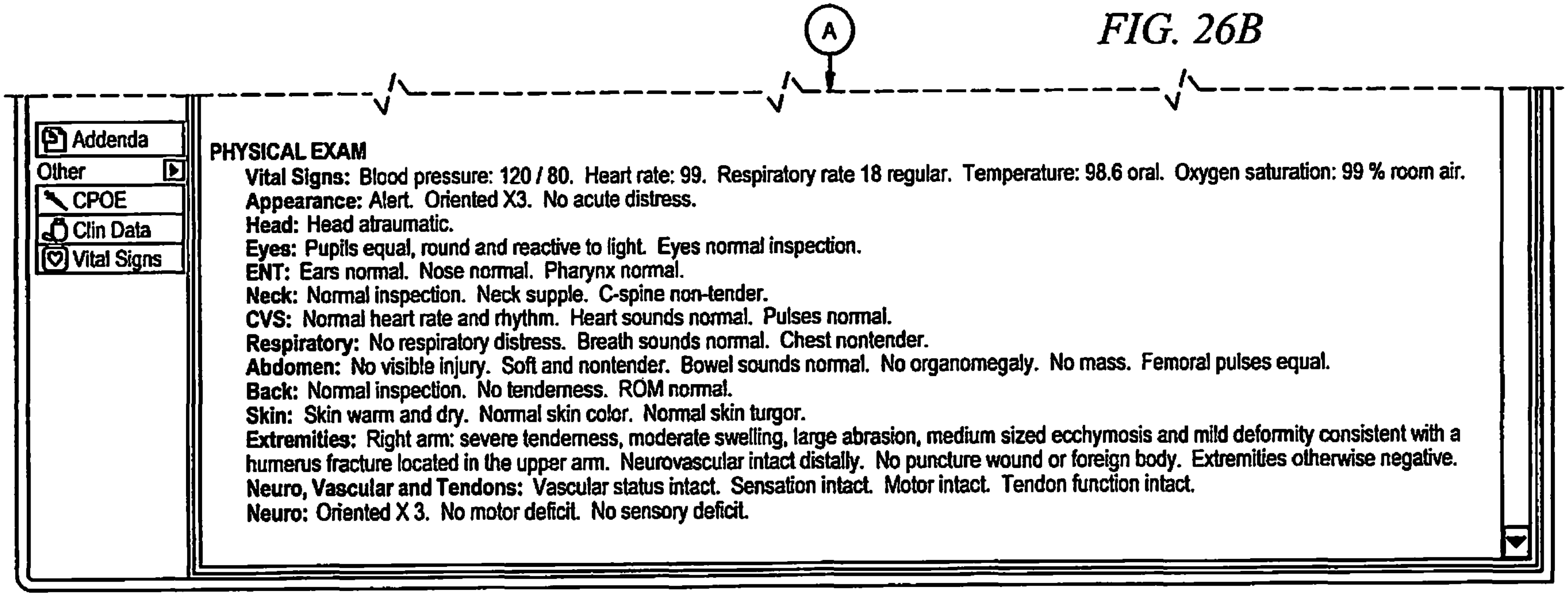

FIG. 26B

PHYSICAL EXAM
Vital Signs: Blood pressure: 120 / 80. Heart rate: 99. Respiratory rate 18 regular. Temperature: 98.6 oral. Oxygen saturation: 99 % room air.
Appearance: Alert. Oriented X3. No acute distress.
Head: Head atraumatic.
Eyes: Pupils equal, round and reactive to light. Eyes normal inspection.
ENT: Ears normal. Nose normal. Pharynx normal.
Neck: Normal inspection. Neck supple. C-spine non-tender.
CVS: Normal heart rate and rhythm. Heart sounds normal. Pulses normal.
Respiratory: No respiratory distress. Breath sounds normal. Chest nontender.
Abdomen: No visible injury. Soft and nontender. Bowel sounds normal. No organomegaly. No mass. Femoral pulses equal.
Back: Normal inspection. No tenderness. ROM normal.
Skin: Skin warm and dry. Normal skin color. Normal skin turgor.
Extremities: Right arm: severe tenderness, moderate swelling, large abrasion, medium sized ecchymosis and mild deformity consistent with a humerus fracture located in the upper arm. Neurovascular intact distally. No puncture wound or foreign body. Extremities otherwise negative.
Neuro, Vascular and Tendons: Vascular status intact. Sensation intact. Motor intact. Tendon function intact.
Neuro: Oriented X 3. No motor deficit. No sensory deficit.

Addenda
Other
CPOE
Clin Data
Vital Signs

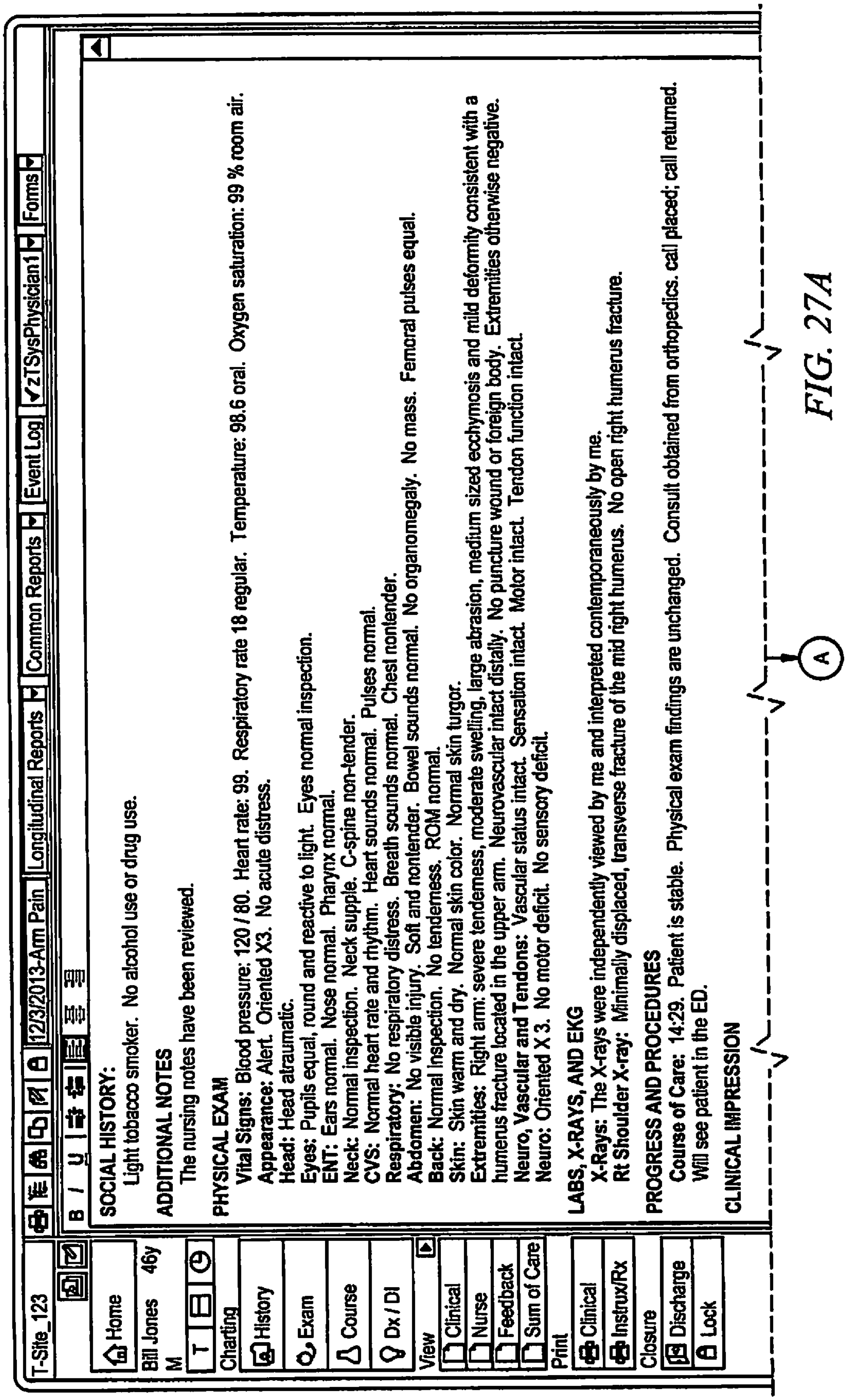

FIG. 27A

T-Site_123

Home
Bill Jones 46y
M

Charting
- History
- Exam
- Course
- Dx / DI

View
- Clinical
- Nurse
- Feedback
- Sum of Care

Print
- Clinical
- Instrux/Rx

Closure
- Discharge
- Lock

12/3/2013 - Arm Pain | Longitudinal Reports | Common Reports | Event Log | zTSvsPhysician1 | Forms

B I U

SOCIAL HISTORY:
Light tobacco smoker. No alcohol use or drug use.

ADDITIONAL NOTES
The nursing notes have been reviewed.

PHYSICAL EXAM
Vital Signs: Blood pressure: 120 / 80. Heart rate: 99. Respiratory rate 18 regular. Temperature: 98.6 oral. Oxygen saturation: 99 % room air.
Appearance: Alert. Oriented X3. No acute distress.
Head: Head atraumatic.
Eyes: Pupils equal, round and reactive to light. Eyes normal inspection.
ENT: Ears normal. Nose normal. Pharynx normal.
Neck: Normal inspection. Neck supple. C-spine non-tender.
CVS: Normal heart rate and rhythm. Heart sounds normal. Pulses normal.
Respiratory: No respiratory distress. Breath sounds normal. Chest nontender.
Abdomen: No visible injury. Soft and nontender. Bowel sounds normal. No organomegaly. No mass. Femoral pulses equal.
Back: Normal Inspection. No tenderness. ROM normal.
Skin: Skin warm and dry. Normal skin color. Normal skin turgor.
Extremities: Right arm: severe tenderness, moderate swelling, large abrasion, medium sized ecchymosis and mild deformity consistent with a humerus fracture located in the upper arm. Neurovascular intact distally. No puncture wound or foreign body. Extremities otherwise negative.
Neuro, Vascular and Tendons: Vascular status intact. Sensation intact. Motor intact. Tendon function intact.
Neuro: Oriented X 3. No motor deficit. No sensory deficit.

LABS, X-RAYS, AND EKG
X-Rays: The X-rays were independently viewed by me and interpreted contemporaneously by me.
Rt Shoulder X-ray: Minimally displaced, transverse fracture of the mid right humerus. No open right humerus fracture.

PROGRESS AND PROCEDURES
Course of Care: 14:29. Patient is stable. Physical exam findings are unchanged. Consult obtained from orthopedics, call placed; call returned. Will see patient in the ED.

CLINICAL IMPRESSION

Ⓐ

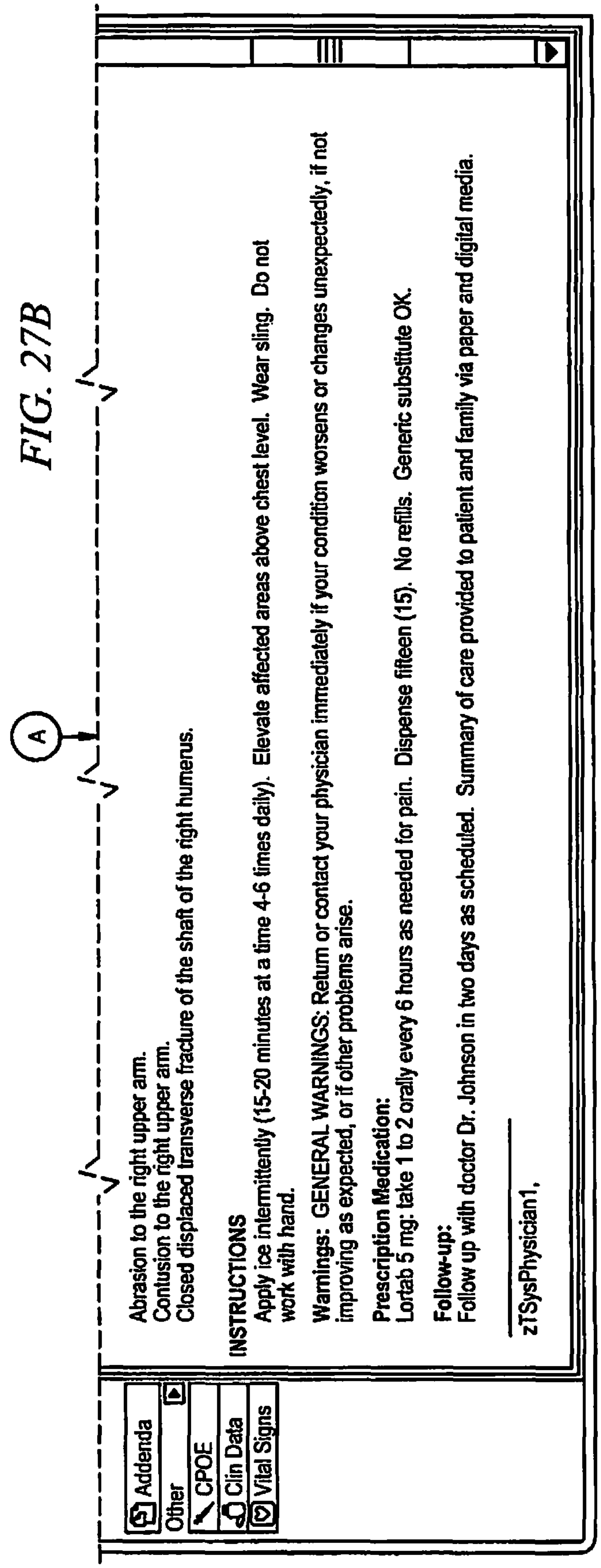

FIG. 27B

Abrasion to the right upper arm.
Contusion to the right upper arm.
Closed displaced transverse fracture of the shaft of the right humerus.

INSTRUCTIONS
Apply ice intermittently (15-20 minutes at a time 4-6 times daily). Elevate affected areas above chest level. Wear sling. Do not work with hand.

Warnings: GENERAL WARNINGS: Return or contact your physician immediately if your condition worsens or changes unexpectedly, if not improving as expected, or if other problems arise.

Prescription Medication:
Lortab 5 mg: take 1 to 2 orally every 6 hours as needed for pain. Dispense fifteen (15). No refills. Generic substitute OK.

Follow-up:
Follow up with doctor Dr. Johnson in two days as scheduled. Summary of care provided to patient and family via paper and digital media.

zTSysPhysician1,

Addenda
Other
CPOE
Clin Data
Vital Signs

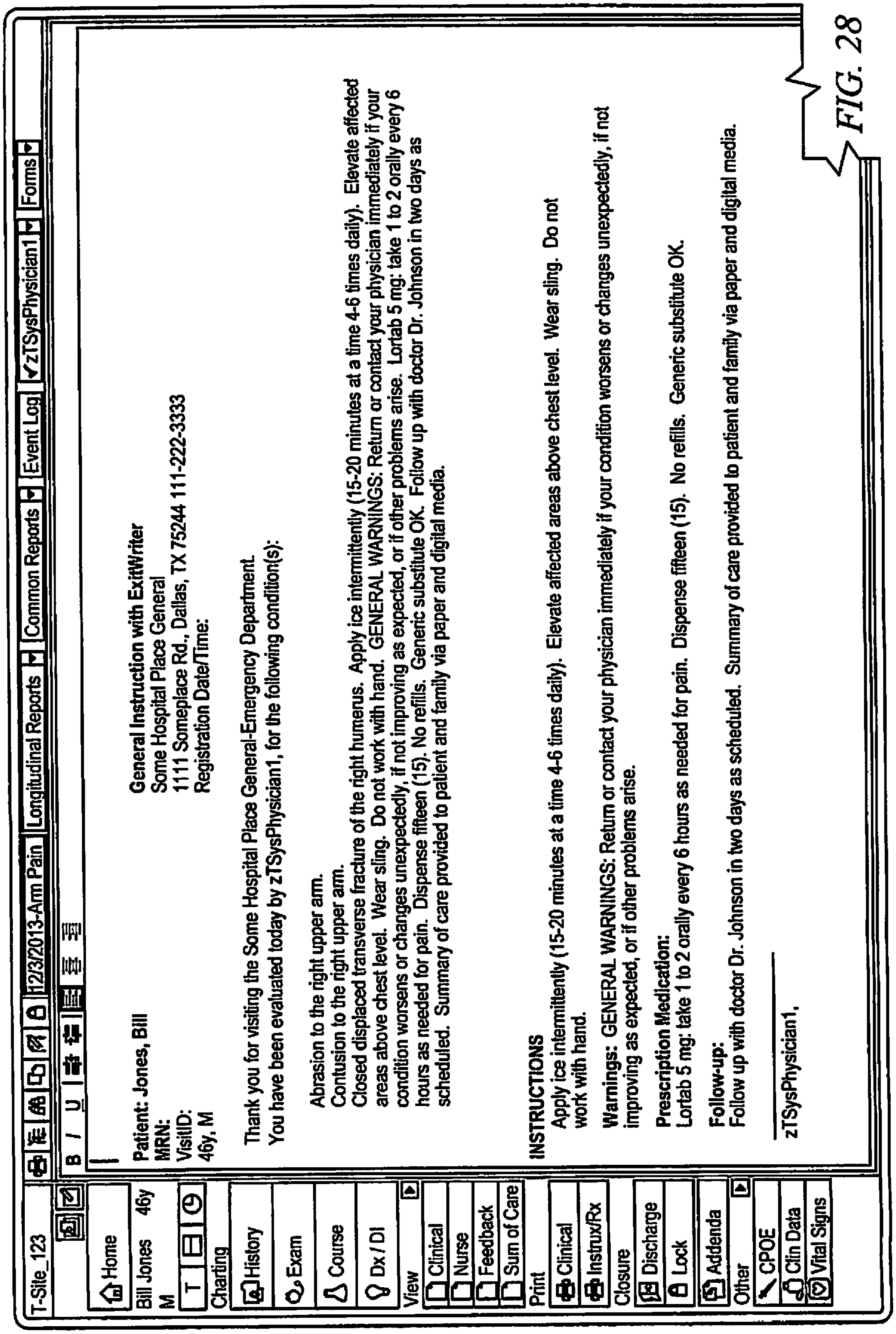

FIG. 28

General Instruction with ExitWriter
Some Hospital Place General
1111 Someplace Rd., Dallas, TX 75244 111-222-3333
Registration Date/Time:

Patient: Jones, Bill
MRN:
VisitID:
46y, M

Thank you for visiting the Some Hospital Place General-Emergency Department.
You have been evaluated today by zTSysPhysician1, for the following condition(s):

Abrasion to the right upper arm.
Contusion to the right upper arm.
Closed displaced transverse fracture of the right humerus. Apply ice intermittently (15-20 minutes at a time 4-6 times daily). Elevate affected areas above chest level. Wear sling. Do not work with hand. GENERAL WARNINGS: Return or contact your physician immediately if your condition worsens or changes unexpectedly, or if other problems arise. Lortab 5 mg: take 1 to 2 orally every 6 hours as needed for pain. Dispense fifteen (15). No refills. Generic substitute OK. Follow up with doctor Dr. Johnson in two days as scheduled. Summary of care provided to patient and family via paper and digital media.

INSTRUCTIONS
Apply ice intermittently (15-20 minutes at a time 4-6 times daily). Elevate affected areas above chest level. Wear sling. Do not work with hand.
Warnings: GENERAL WARNINGS: Return or contact your physician immediately if your condition worsens or changes unexpectedly, if not improving as expected, or if other problems arise.
Prescription Medication:
Lortab 5 mg: take 1 to 2 orally every 6 hours as needed for pain. Dispense fifteen (15). No refills. Generic substitute OK.
Follow-up:
Follow up with doctor Dr. Johnson in two days as scheduled. Summary of care provided to patient and family via paper and digital media.

zTSysPhysician1,

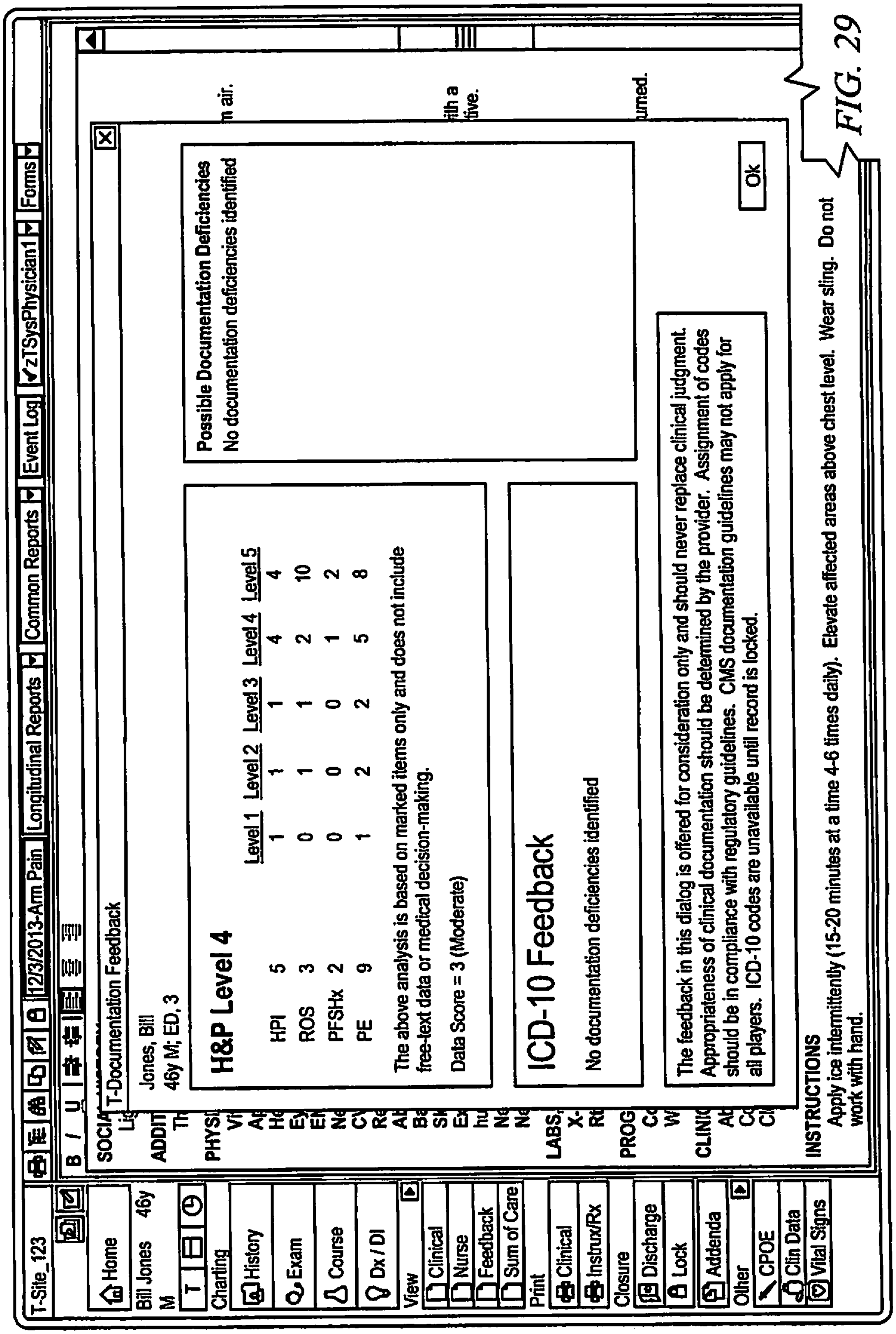

FIG. 29

(rotated screenshot of EHR interface)

T-Site_123
Home
Bill Jones 46y
M

Charting
History
Exam
Course
Dx / DI

View
Clinical
Nurse
Feedback
Sum of Care

Print
Clinical
Instrux/Rx

Closure
Discharge
Lock
Addenda
Other
CPOE
Clin Data
Vital Signs

12/3/2013-Arm Pain | Longitudinal Reports | Common Reports | Event Log | zTSysPhysician1 | Forms T-Documentation Feedback Jones, Bill
46y M; ED, 3

H&P Level 4

|  | Level 1 | Level 2 | Level 3 | Level 4 | Level 5 |
|---|---|---|---|---|---|
| HPI | 5 | 1 | 1 | 4 | 4 |
| ROS | 3 | 0 | 1 | 2 | 10 |
| PFSHx | 2 | 0 | 0 | 1 | 2 |
| PE | 9 | 1 | 2 | 5 | 8 |

The above analysis is based on marked items only and does not include free-text data or medical decision-making.

Data Score = 3 (Moderate)

ICD-10 Feedback

No documentation deficiencies identified

Possible Documentation Deficiencies

No documentation deficiencies identified

Ok

The feedback in this dialog is offered for consideration only and should never replace clinical judgment. Appropriateness of clinical documentation should be determined by the provider. Assignment of codes should be in compliance with regulatory guidelines. CMS documentation guidelines may not apply for all payers. ICD-10 codes are unavailable until record is locked.

INSTRUCTIONS
Apply ice intermittently (15-20 minutes at a time 4-6 times daily). Elevate affected areas above chest level. Wear sling. Do not work with hand.

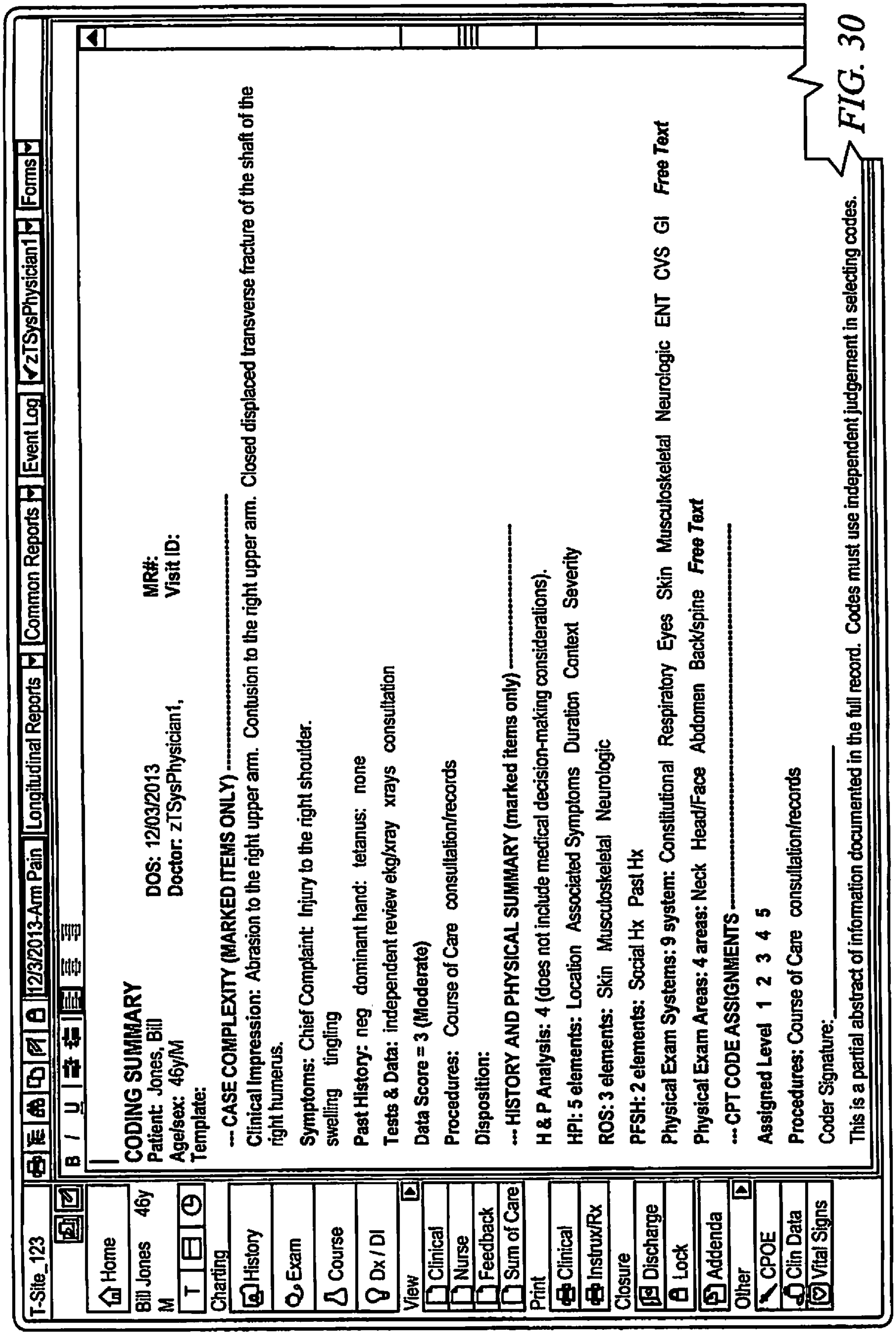

FIG. 30

T-Site_123

Bill Jones 46y
M

Home

Charting
- History
- Exam
- Course
- Dx / DI

View
- Clinical
- Nurse
- Feedback
- Sum of Care

Print
- Clinical
- Instrux/Rx

Closure
- Discharge
- Lock
- Addenda

Other
- CPOE
- Clin Data
- Vital Signs

| 12/3/2013-Arm Pain | Longitudinal Reports | Common Reports | Event Log | zTSysPhysician1 | Forms |

CODING SUMMARY
Patient: Jones, Bill          DOS: 12/03/2013          MR#:
Age/sex: 46y/M                Doctor: zTSysPhysician1,     Visit ID:
Template:

--- CASE COMPLEXITY (MARKED ITEMS ONLY) ---
Clinical Impression: Abrasion to the right upper arm. Contusion to the right upper arm. Closed displaced transverse fracture of the shaft of the right humerus.

Symptoms: Chief Complaint: Injury to the right shoulder.
swelling  tingling

Past History: neg  dominant hand:  tetanus:  none

Tests & Data: independent review ekg/xray  xrays  consultation

Data Score = 3 (Moderate)

Procedures: Course of Care  consultation/records

Disposition:

--- HISTORY AND PHYSICAL SUMMARY (marked items only) ---
H & P Analysis: 4 (does not include medical decision-making considerations).
HPI: 5 elements: Location  Associated Symptoms  Duration  Context  Severity
ROS: 3 elements: Skin  Musculoskeletal  Neurologic
PFSH: 2 elements: Social Hx  Past Hx
Physical Exam Systems: 9 system: Constitutional  Respiratory  Eyes  Skin  Musculoskeletal  Neurologic  ENT  CVS  GI  *Free Text*
Physical Exam Areas: 4 areas: Neck  Head/Face  Abdomen  Back/spine  *Free Text*

--- CPT CODE ASSIGNMENTS ---
Assigned Level  1  2  3  4  5
Procedures: Course of Care  consultation/records
Coder Signature:
This is a partial abstract of information documented in the full record. Codes must use independent judgement in selecting codes.

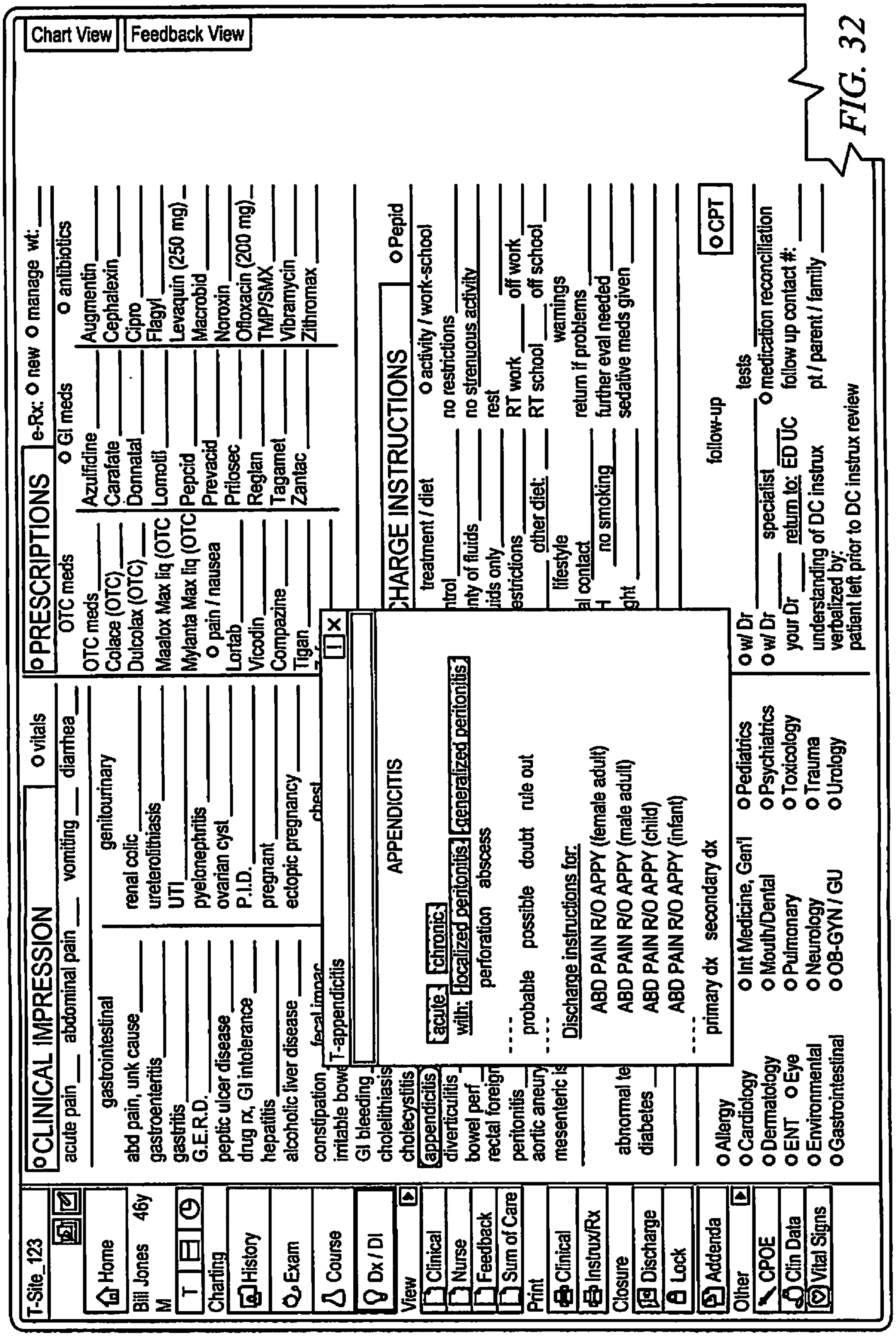

FIG. 32

[Chart View] [Feedback View]

T-Site_123
Home — Bill Jones 46y M
Charting
- History
- Exam
- Course
- Dx / DI View
- Clinical
- Nurse
- Feedback
- Sum of Care Print
- Clinical
- Instruc/Rx Closure
- Discharge
- Lock Addenda
Other
- CPOE
- Clin Data
- Vital Signs ○ CLINICAL IMPRESSION _____ ○ vitals
acute pain ___ abdominal pain ___ vomiting ___ diarrhea ___
gastrointestinal                    genitourinary
abd pain, unk cause ___             renal colic ___
gastroenteritis ___                 ureterolithiasis ___
gastritis ___                       UTI ___
G.E.R.D. ___                        pyelonephritis ___
peptic ulcer disease ___            ovarian cyst ___
drug rx, GI intolerance ___         P.I.D. ___
hepatitis ___                       pregnant ___
alcoholic liver disease ___         ectopic pregnancy ___
constipation ___ fecal impac___     chest
irritable bowel ___
GI bleeding ___
cholelithiasis ___
cholecystitis ___
appendicitis ___  T-appendicitis
diverticulitis ___
bowel perf ___
rectal foreign ___
peritonitis ___
aortic aneury ___
mesenteric is___
abnormal te___
diabetes ___

○ Allergy          ○ Int Medicine, Gen'l   ○ Pediatrics
○ Cardiology       ○ Mouth/Dental          ○ Psychiatrics
○ Dermatology      ○ Pulmonary             ○ Toxicology
○ ENT  ○ Eye       ○ Neurology             ○ Trauma
○ Environmental    ○ OB-GYN / GU           ○ Urology
○ Gastrointestinal ○ PRESCRIPTIONS    e-Rx:  ○ new  ○ manage  wt: ___
     OTC meds           ○ GI meds              ○ antibiotics
OTC meds ___           Azulfidine ___         Augmentin ___
Colace (OTC) ___       Carafate ___           Cephalexin ___
Dulcolax (OTC) ___     Donnatal ___           Cipro ___
Maalox Max liq (OTC)___ Lomotil ___           Flagyl ___
Mylanta Max liq (OTC)__ Pepcid ___            Levaquin (250 mg) ___
   ○ pain / nausea     Prevacid ___           Macrobid ___
Lortab ___             Prilosec ___           Noroxin ___
Vicodin ___            Reglan ___             Ofloxacin (200 mg) ___
Compazine ___          Tagamet ___            TMP/SMX ___
Tigan ___              Zantac ___             Vibramycin ___
                                              Zithromax ___

APPENDICITIS                              □ ×

[acute] [chronic]
with: [localized peritonitis] [generalized peritonitis]
     perforation   abscess
- - -
     probable   possible   doubt   rule out Discharge instructions for:
     ABD PAIN R/O APPY (female adult)
     ABD PAIN R/O APPY (male adult)
     ABD PAIN R/O APPY (child)
     ABD PAIN R/O APPY (infant)
- - -
     primary dx   secondary dx ○ CHARGE INSTRUCTIONS                     ○ Pepid
     treatment / diet          ○ activity / work-school
 ___trol                     no restrictions ___
 ___nty of fluids            no strenuous activity ___
 ___ids only                 rest ___
 ___strictions               ___ RT work ___ off work ___
           other diet:       ___ RT school ___ off school ___
                lifestyle              warnings
 ___l contact                return if problems ___
 ___H  no smoking            further eval needed ___
 ___ght                      sedative meds given ___ follow-up
                    ___ tests ___
○ w/ Dr ___ specialist ___  ○ medication reconciliation
○ w/ Dr ___ return to: ED UC  follow up contact #: ___
your Dr ___ understanding of DC instrux    pt / parent / family
            verbalized by: ___           ○ CPT
            patient left prior to DC instrux review

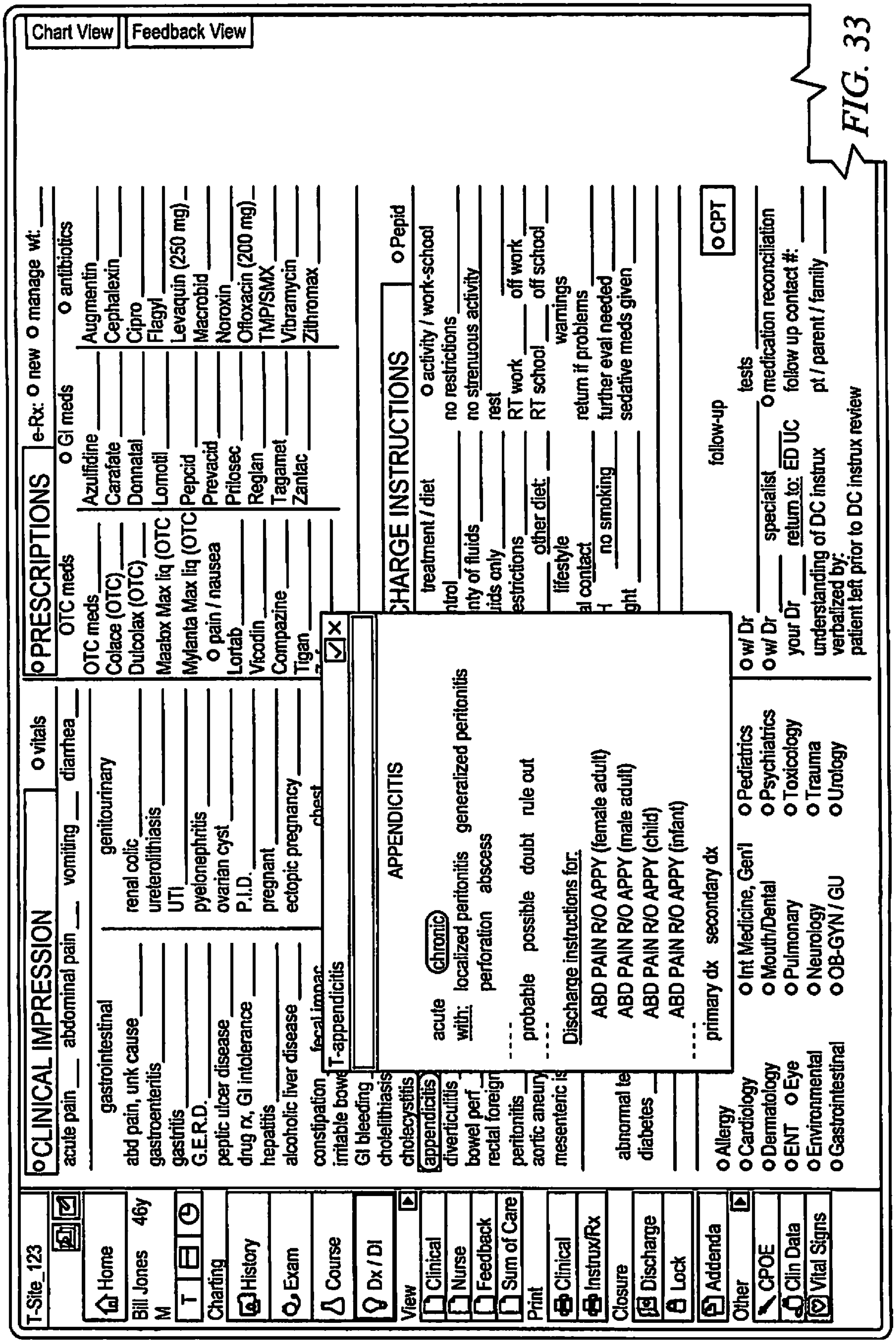

FIG. 33

T-Site_123
Bill Jones 46y M
T | | ⊘

Charting
- Home
- History
- Exam
- Course
- Dx / DI

View
- Clinical
- Nurse
- Feedback
- Sum of Care

Print
- Clinical
- Instrux/Rx

Closure
- Discharge
- Lock

Other
- Addenda

CPOE
- Clin Data
- Vital Signs

Chart View | Feedback View

○ CLINICAL IMPRESSION ○ vitals
acute pain___ abdominal pain___ vomiting___ diarrhea___
gastrointestinal                    genitourinary
abd pain, unk cause ___    renal colic ___
gastroenteritis ___              ureterolithiasis ___
gastritis ___                         UTI ___
G.E.R.D. ___                       pyelonephritis ___
peptic ulcer disease ___     ovarian cyst ___
drug rx, GI intolerance ___ P.I.D. ___
hepatitis ___                       pregnant ___
alcoholic liver disease ___ ectopic pregnancy ___
constipation ___                              chest___
fecal impac___
irritable bowe T-appendicitis          ☑ ×
GI bleeding
cholelithiasis       APPENDICITIS
cholecystitis
appendicitis      acute  (Chronic)
diverticulitis     with: localized peritonitis  generalized peritonitis
bowel perf              perforation  abscess
rectal foreign
peritonitis        probable  possible  doubt  rule out
aortic aneury
mesenteric i    Discharge instructions for:
                        ABD PAIN R/O APPY (female adult)
abnormal te    ABD PAIN R/O APPY (male adult)
diabetes         ABD PAIN R/O APPY (child)
                        ABD PAIN R/O APPY (infant)

primary dx   secondary dx

○ Allergy           ○ Int Medicine, Gen'l  ○ Pediatrics
○ Cardiology     ○ Mouth/Dental          ○ Psychiatrics
○ Dermatology ○ Pulmonary                ○ Toxicology
○ ENT  ○ Eye   ○ Neurology                 ○ Trauma
○ Environmental ○ OB-GYN / GU          ○ Urology
○ Gastrointestinal ○ PRESCRIPTIONS   e-Rx: ○ new  ○ manage  w/: ___
OTC meds                    ○ GI meds___        ○ antibiotics
OTC meds ___             Azulfidine ___      Augmentin ___
Colace (OTC) ___        Carafate ___         Cephalexin ___
Dulcolax (OTC) ___     Donnatal ___         Cipro ___
Maalox Max liq (OTC) Lomotil ___            Flagyl ___
Mylanta Max liq (OTC)Pepcid ___             Levaquin (250 mg) ___
  ○ pain / nausea          Prevacid ___         Macrobid ___
Lortab ___                     Pritosec ___          Noroxin ___
Vicodin ___                    Reglan ___            Ofloxacin (200 mg) ___
Compazine ___            Tagamet ___          TMP/SMX ___
Tigan ___                      Zantac ___              Vibramycin ___
                                                                      Zithromax ___

○ DISCHARGE INSTRUCTIONS             ○ Pepid
   treatment / diet          ○ activity / work-school
___trol                              no restrictions
nty of fluids                    no strenuous activity
uids only                        rest
estrictions                      RT work___ off work___
            other diet___   RT school___ off school___
   lifestyle                       warnings
___                                 return if problems
   ___no smoking          further eval needed
___ght                            sedative meds given follow-up                              ☐ CPT
○ w/ Dr ___              ___specialist      ○ medication reconciliation
○ w/ Dr ___              return to: ED UC   follow up contact #: ___
your Dr ___              tests ___               pt / parent / family ___
  understanding of DC instrux
  verbalized by: ___
  patient left prior to DC instrux review

SYSTEMS AND METHODS FOR CODING DATA FROM A MEDICAL ENCOUNTER

CROSS-REFERENCE TO RELATED APPLICATIONS

The present application is a Continuation Application of U.S. patent application Ser. No. 16/121,591, filed Sep. 4, 2018, and entitled "SYSTEMS AND METHODS FOR CODING DATA FROM A MEDICAL ENCOUNTER," which is a Continuation Application of U.S. patent application Ser. No. 14/170,437, filed Jan. 31, 2014, and entitled "SYSTEMS AND METHODS FOR CODING DATA FROM A MEDICAL ENCOUNTER," the disclosures of which are each incorporated by reference herein in their entireties.

FIELD OF THE DISCLOSURE

The present application relates to documenting medical encounters and more specifically to coding diagnoses resulting from a doctor-patient encounter.

OVERVIEW OF THE DISCLOSURE

Throughout a doctor-patient encounter a physician generally must keep precise records corresponding to the patient. These patient records include information relating to patient history, current problems, diagnoses for a particular visit, courses of treatment and medical reports. These records serve many functions relating to the actual treatment of the patient in order to safeguard proper care. More recently, proper records and documentation are also required for physicians to create proper billing statements so they can receive payments from a patient's insurance provider for services rendered.

One important aspect that must be provided for in a claims submission to a payment provider is a diagnosis relating to the patient which justifies actions taken by a physician. Without a diagnosis in a claim submission, many actions taken by a physician will not be deemed to be necessary by a payment provider and therefore will not be covered for payment. A diagnosis is usually provided on a claim submission in the form of a code. Currently, codes which are standardized under the International Classification of Diseases 9 standard (ICD-9) are widely utilized. There are approximately 13,000 codes in the ICD-9 standard which cover a broad spectrum of medicine. For billing purposes, a physician will generally employ a biller/coder that takes a physician's written diagnosis and matches it to a specific ICD-9 code and enters it onto a claim form for submission. This system generally works as the codes are sufficiently broad enough that a coder can look up the proper code. Additionally, because a physician may work in specific areas of medicine, a coder can become familiar with common codes.

Beginning on Oct. 1, 2014, many in the medical field will be required to utilize codes in the ICD-10 for billing purposes. ICD-10 utilizes over 68,000 codes and can be very specific (e.g. identifies right versus left side, code allows for description of comorbidities, manifestations, etiology/causation, complications, detailed anatomic location, sequelae, degree of impairment, biologic and chemical agents, phase/stage, lymph node involvement, age related, procedure or implant related, etc.). This raises many issues in the overall practice of medicine both on the billing side and during an actual patient encounter due to the fact that more/different details may be required to determine a proper diagnosis code.

For example, currently if a patient sees a physician because of a broken arm, a physician may note that the patient has a "closed radius shaft fracture" under ICD-9 (which corresponds to code 813.21). However, if the same terminology was utilized under ICD-10, the description would be a "closed unspecified fracture of the shaft of an unspecified radius." Because multiple portions needed to generate a code would remain unspecified, payment to a physician could be delayed or even rejected. Further, it is notable that for the example of a fractured radius there are 27 possible ICD-9 codes whereas there are 2,960 possible ICD-10 codes. Because of this, not only has the billing process been altered by requiring coders to manage more detailed possibilities for diagnoses and procedures, additional data may need to be obtained/documented by a physician during a patient encounter beyond what a physician is accustomed to obtaining during the normal course of practicing medicine.

One current solution to this problem that has been implemented utilizes a natural language processing engine to locate and determine an appropriate code. In this solution, a computing device receives a typed or dictated natural language input and automatically searches the ICD-10 code database for proper diagnosis codes. This solution raises multiple issues. First, the technology underlying the natural language searches is still unreliable and inaccurate. Further, because a physician does not necessarily know what new information is needed, the proper terminology to plug into the natural language algorithm may not be present.

Another approach entails simply conducting a key word search whereupon a physician or billing/coding professional enters a diagnosis and/or other key terms. However, in many cases depending on the type of problems exhibited by a patient, a key word search may yield 500 or more results. These results would then need to be reviewed and a code would be selected. This approach is not always feasible and/or conducive to finding a proper code in an efficient manner. Further, as with the natural language solution, because the physician may not necessarily know what new information is needed, the proper terminology to plug into the search engine may not be present in the patient documentation.

SUMMARY OF THE DISCLOSURE

The present application provides for systems and methods which assist in gathering and/or documenting relevant data in a doctor-patient encounter for obtaining a proper, fully specified, diagnosis and/or procedure code. In one embodiment, selectable data items which are provided as part of a medical charting program may be correlated with one or more standardized diagnosis/procedure codes (e.g. ICD-10 codes). Upon selection of the appropriate data items when charting a patient encounter, one or more codes which are correlated with the selected data items may be flagged and/or generated for later use, such as for filing a claim submission as part of a billing process.

In one embodiment, as selectable data items are selected, dynamic tracking of entered information with respect to one or more diagnosis codes may be implemented. For example, as data items corresponding to one or more codes are received, embodiments may track the data items and corresponding codes to determine if one or more data items are needed to definitively select a diagnosis code. When one or more data items are missing, in order to properly code a diagnosis or procedure, embodiments may provide an indication to a user that more information is needed. Embodiments may further display which particular items are needed.

In another embodiment, a diagnosis or procedure code may require a particular selection of data items from different categories. As a data item from such categories are missing, embodiments may provide an indication to the user and may also display which categories of data remain to be addressed in order to properly specify a particular diagnosis code.

In one embodiment, error checking methods may also be implemented such that when a user completes, or finishes a portion of, the data item collection and one or more data entries are missing with respect to a likely diagnosis or procedure, the user may be notified of the deficiencies and provided with information regarding steps that can be completed in order to yield a properly specified code.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE FIGURES

For a more complete understanding, reference is now made to the following descriptions taken in conjunction with the accompanying drawings, in which:

FIG. 9 illustrates an example display for a medical data entry program in accordance with an embodiment of the present application;

FIG. 14 illustrates an example display for a medical data entry program in accordance with an embodiment of the present application;

FIG. 18 illustrates an example display for a medical data entry program in accordance with an embodiment of the present application;

FIG. 20 illustrates an example display for a medical data entry program in accordance with an embodiment of the present application;

FIG. 23 illustrates an example display for a medical data entry program in accordance with an embodiment of the present application;

FIG. 25 illustrates an example display for a medical data entry program in accordance with an embodiment of the present application;

FIGS. 26A and 26B illustrate an example display for a medical data entry program in accordance with an embodiment of the present application;

FIGS. 27A and 27B illustrate an example display for a medical data entry program in accordance with an embodiment of the present application;

FIG. 28 illustrates an example display for a medical data entry program in accordance with an embodiment of the present application;

FIG. 29 illustrates an example display for a medical data entry program in accordance with an embodiment of the present application;

FIG. 30 illustrates an example display for a medical data entry program in accordance with an embodiment of the present application;

FIG. 32 illustrates an example display for a medical data entry program in accordance with an embodiment of the present application;

FIG. 33 illustrates an example display for a medical data entry program in accordance with an embodiment of the present application;

DETAILED DESCRIPTION OF THE DISCLOSURE

In order to clearly describe the inventive concepts of the present application, the following figures illustrate various screen shots of a common workflow that may be undertaken during a doctor-patient encounter. The illustrated example is implemented in a prototype version of the EV™ program by T-System Incorporated. It is appreciated that the specific medical problems shown, and the order of entry of data items, is provided for the sake of example. The context of the following discussion will illustrate that various methods may be utilized to implement embodiments of the present application.

Figure 1:
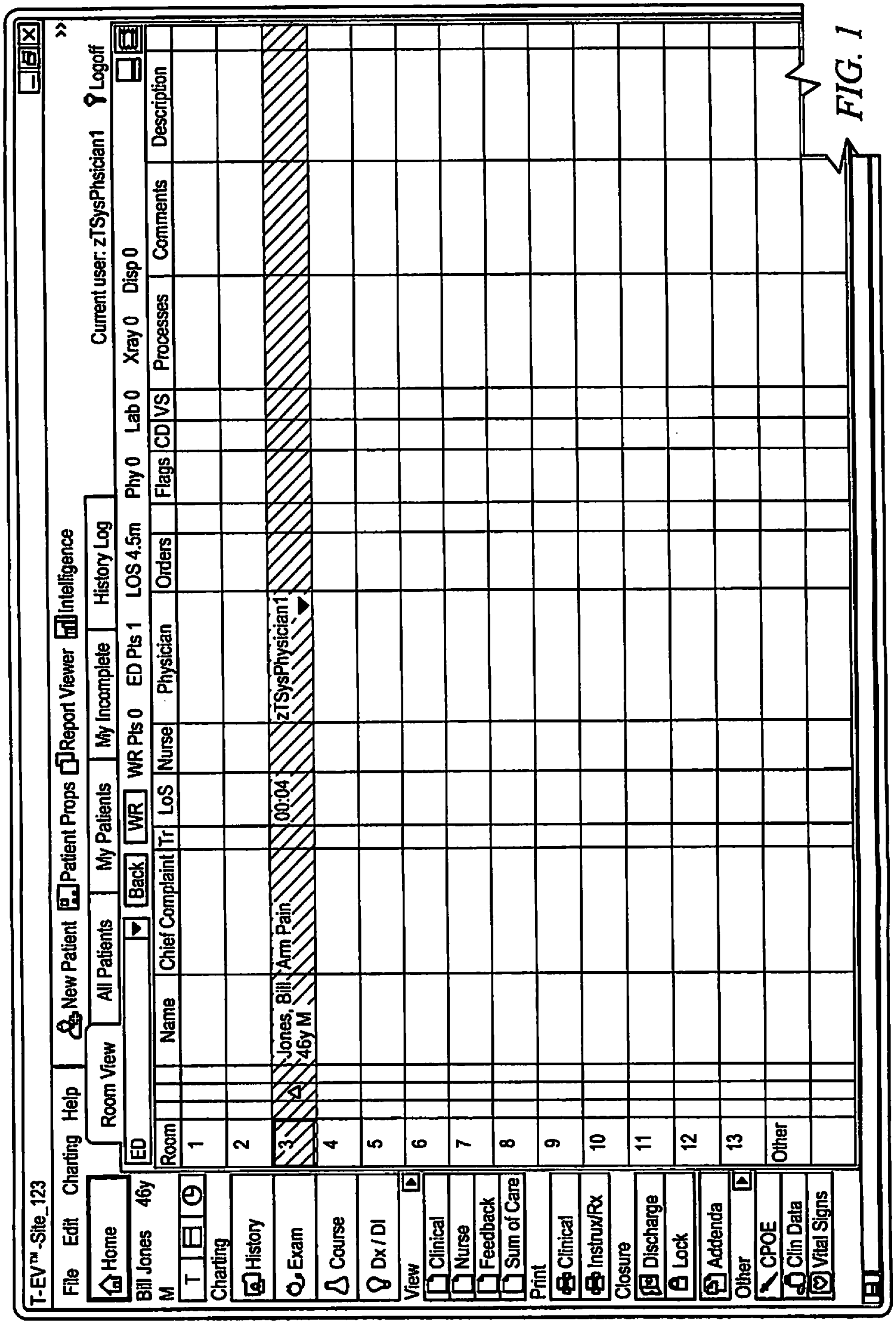
FIG. 1 illustrates an example display for a medical data entry program in accordance with an embodiment of the present application.

FIG. 1 illustrates an initial home screen for a medical data entry program in accordance with an embodiment of the present application. A listing of patients may be provided whereupon a doctor selects a patient that will be or has been encountered. A patient encounter will generally have four portions or categories of information to document. For example, a "History," "Exam," "Course" and "DX/DI" tab on the left side of the screen may be selected which contains a display of selectable data elements for the respective portions of the encounter. The history screen allows data regarding the medical history of the patient and present illness to be entered. The exam screen allows for the entering of data elements representing findings of a physical exam and other tests. The course screen allows for the entry of a course of treatment, results from tests and other information. Finally, the DX/DI screen allows for the entry of data elements pertaining to clinical impressions, diagnoses, discharge instructions and prescriptions.

In many cases, diagnosis or procedure information and a large portion of the data to be received for the purposes of generating a diagnosis/procedure code will be provided by a user under the DX/DI screen. However, embodiments may utilize information from other screens either as contextual information for determining a code, or for actual data entry points. Further, data entered in one or more sections may be imported into other sections for use. For example, a code may require a selection of which arm has been broken (right or left). This information may be entered in the history screen or under the DX/DI screen. When entered in the history screen, such information may be cross-populated where needed.

It is appreciated that the completion and use of the illustrated medical data entry program may be implemented during multiple stages of the encounter (e.g. before, during and/or after). A user may utilize any computing device with sufficient processing resources to implement the described system, e.g. a hand-held tablet device, notebook computer, workstation, etc. Such a device may be connected to a central network (such as one or more of a WAN, LAN, Internet, and the like) and may send/receive data over the network when needed. For example, upon receiving a data entry, a hand-held device may query a remote database for information, receive information and/or store data remotely.

Figure 2:
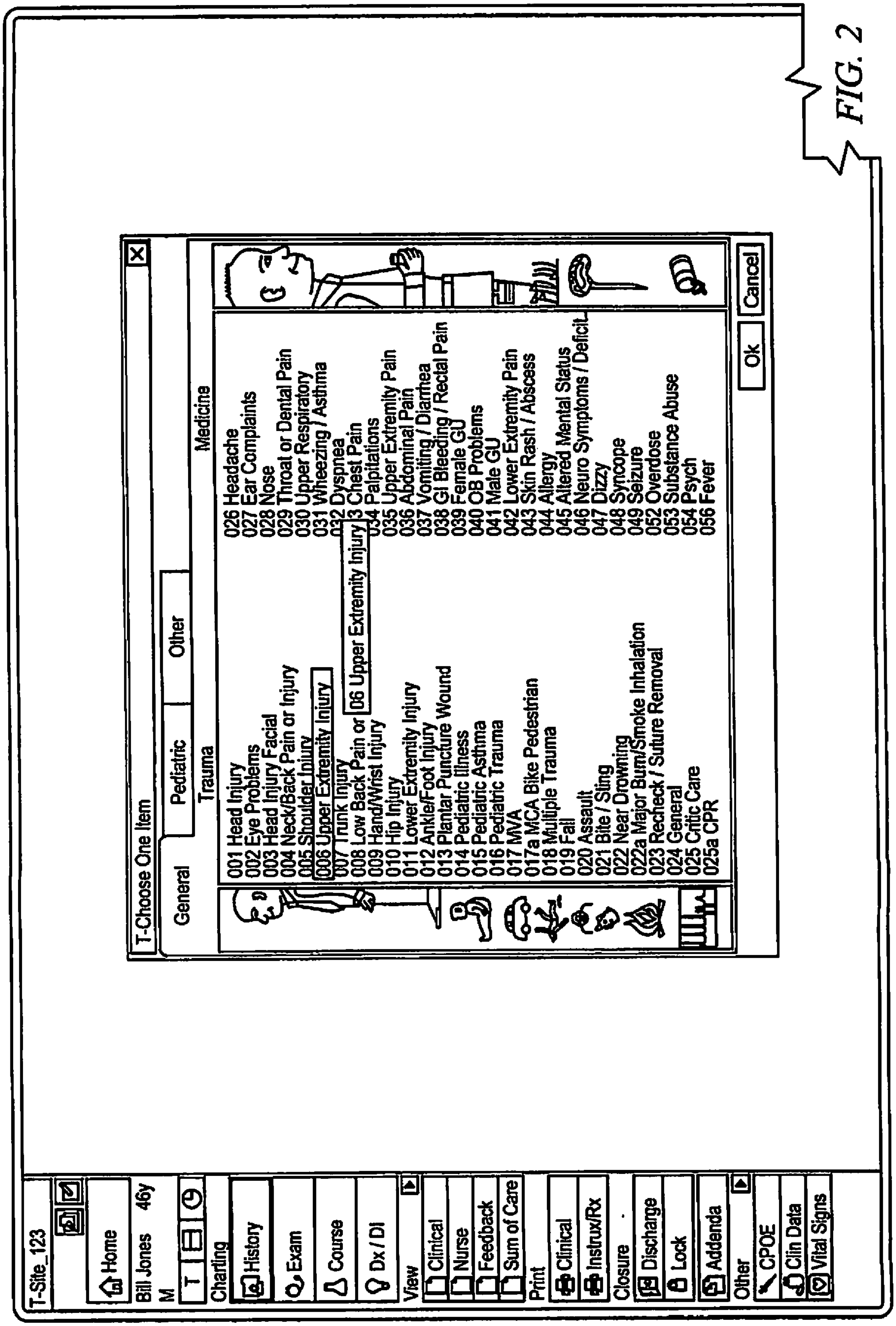
FIG. 2 illustrates an example display for a medical data entry program in accordance with an embodiment of the present application.

Upon selecting a patient, in this case "Bill Jones," a physician may be presented with a template selection screen shown in FIG. 2. The template selection screen allows a physician (or other medical professional) to select a chief medical complaint. Upon selection of a chief medical complaint, a template of selectable data elements is loaded into the system and data elements pertaining to the selected complaint will be presented in the respective history, exam, course, and DX/DI screens. In the illustrated example, the "upper extremity injury" chief medical complaint is selected.

Figure 3:
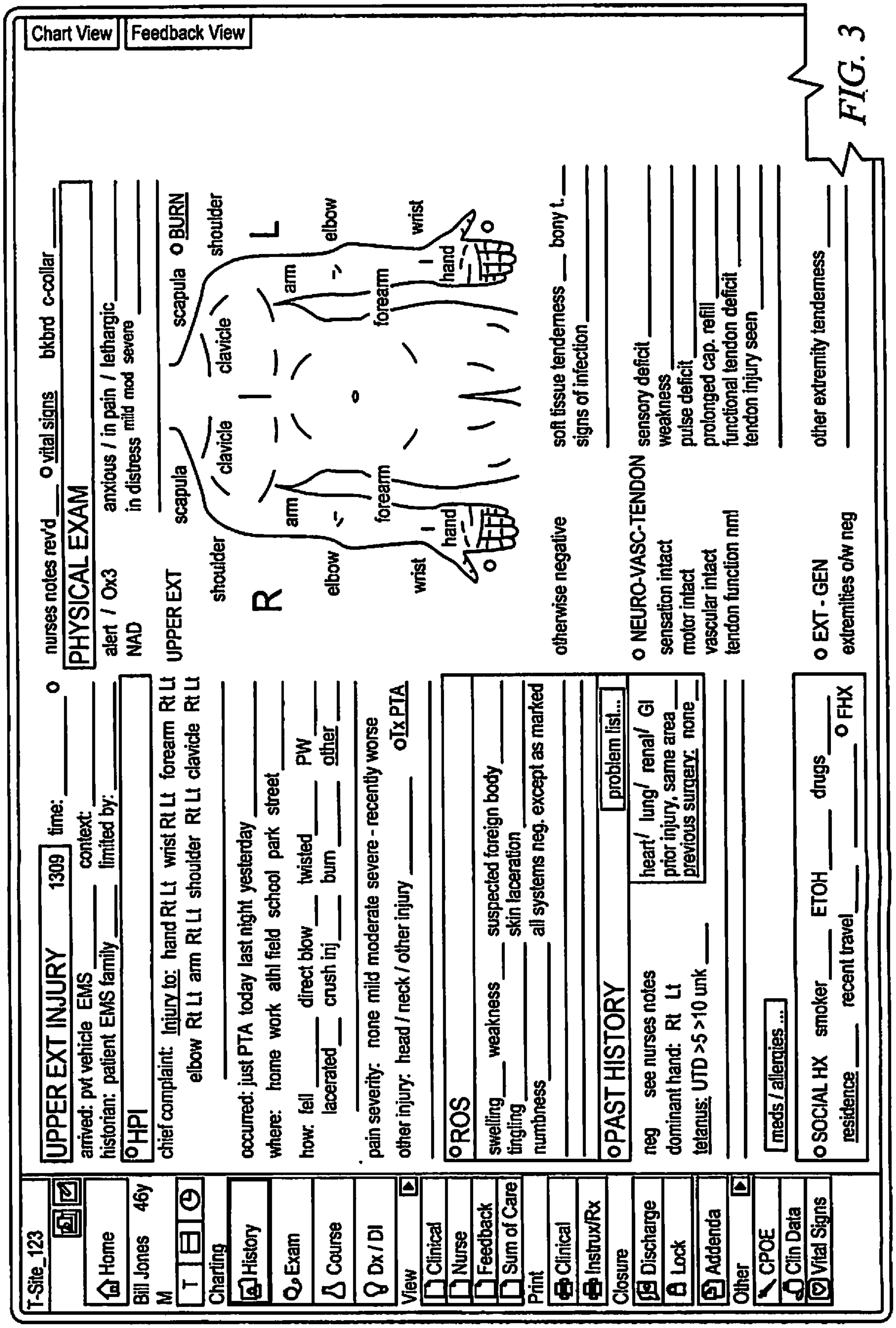
FIG. 3 illustrates an example display for a medical data entry program in accordance with an embodiment of the present application.

FIG. 3 illustrates a history screen in accordance with an embodiment of the present invention. The displayed history screen corresponds to the selected upper extremity injury template. Multiple selectable data elements are provided to a physician/medical professional for selection. One or more of the selectable elements are directed toward the selected chief medical complaint. For example, the upper extremity injury template has selectable data regarding where the injury occurred, e.g. right/left hand, wrist, forearm, elbow, shoulder or clavicle. Other portions may gather additional detail regarding how the injury occurred, when/where it occurred, etc. It is noted that on this particular trauma template physical exam information may also be entered on the history screen as the most relevant information may fit onto a single page (which is usually preferred by the user).

Figure 4:
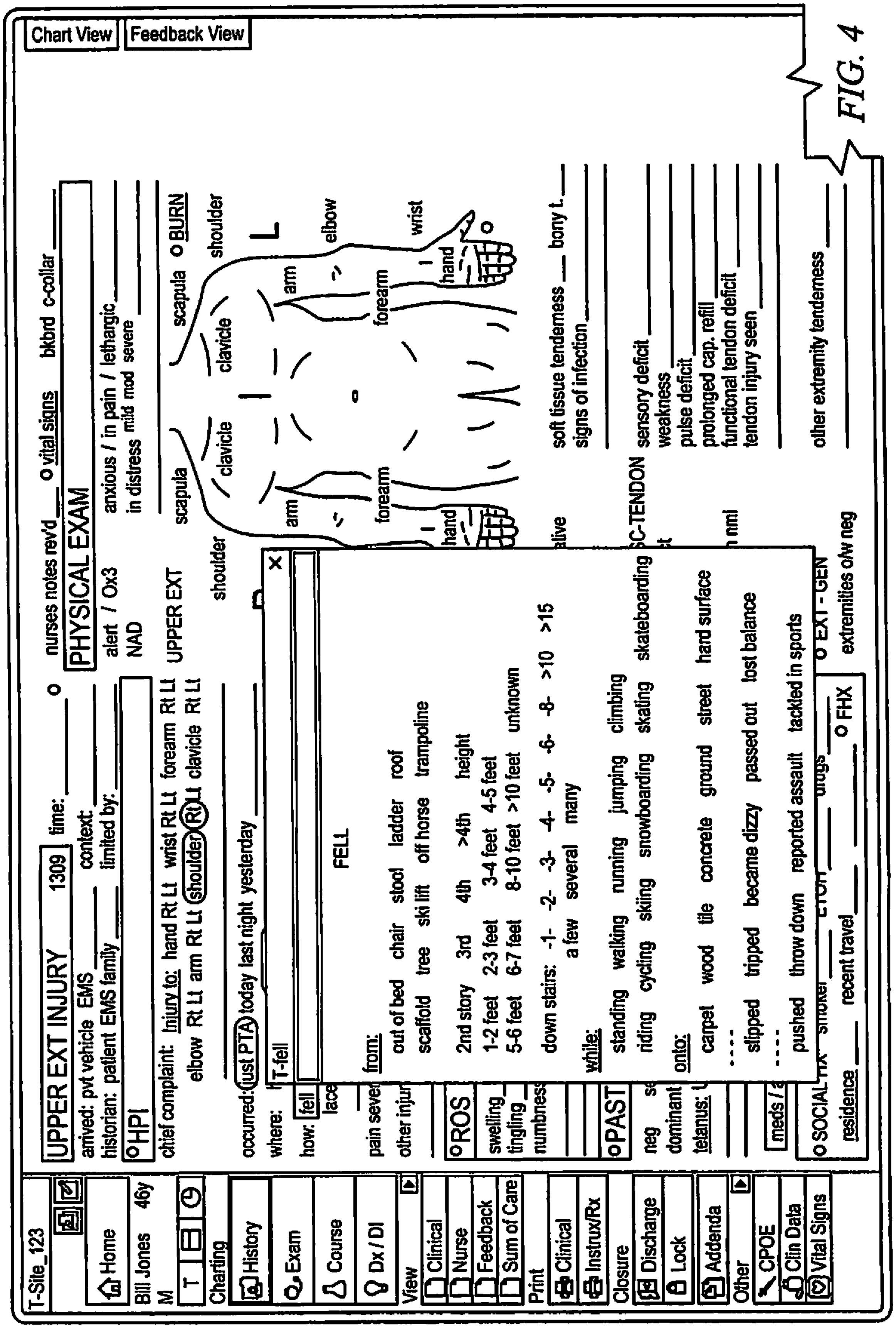
FIG. 4 illustrates an example display for a medical data entry program in accordance with an embodiment of the present application.
Figure 5:
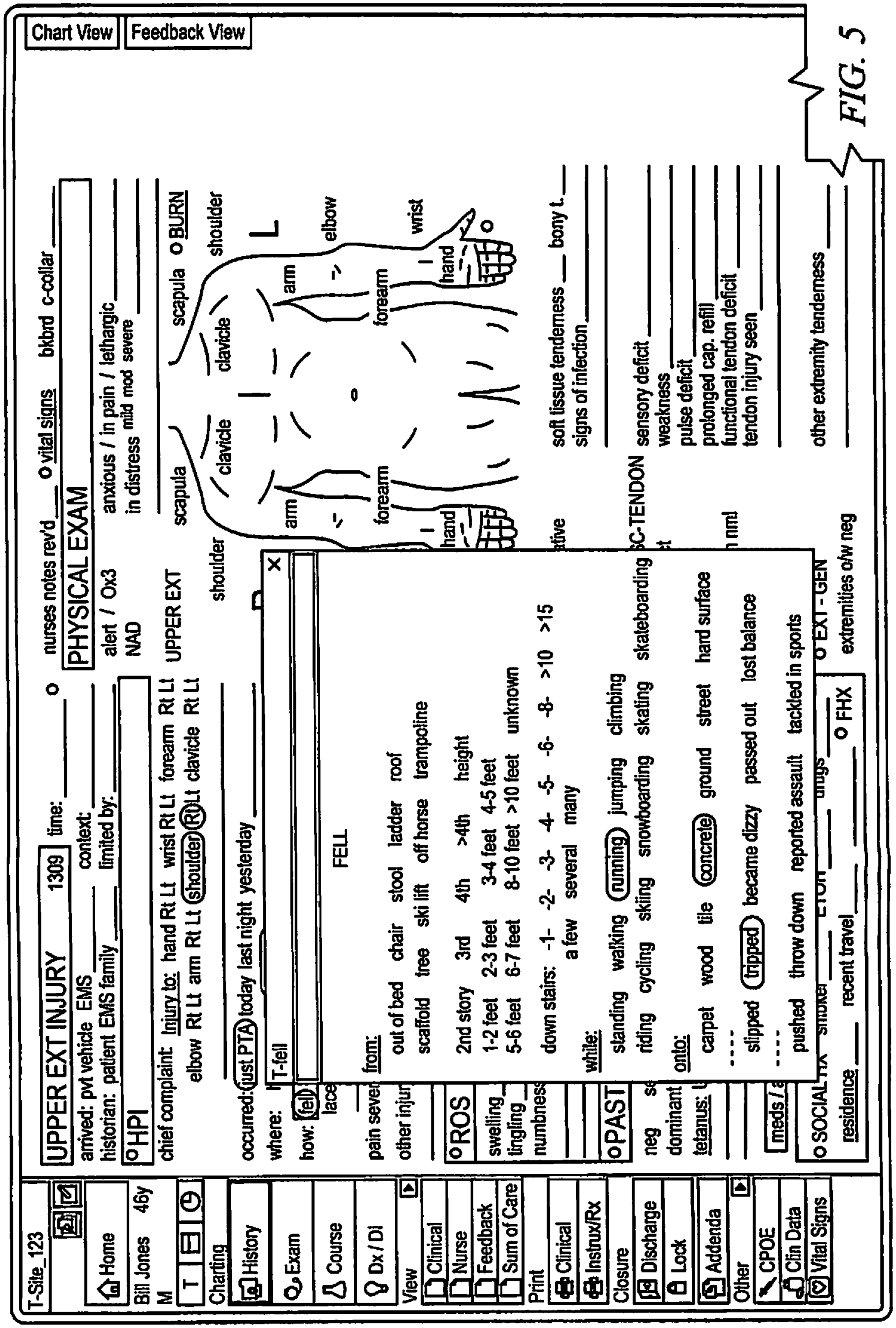
FIG. 5 illustrates an example display for a medical data entry program in accordance with an embodiment of the present application.

FIG. 4 illustrates the history screen of FIG. 3 having selections of data elements. For example, the medical professional has indicated that the relevant injury is to the right shoulder, and it occurred just prior to the patient's arrival at the emergency room. Typically, the medical professional would start marking circles and backslashes to positively select, or to rule out a particular data element, using a right and left mouse click. In the illustrated example the data element corresponding to "fell" is selected and a pop-up screen opens which allows for additional data to be entered. For example, information regarding a fall such as the activity being undertaken, the distance of the fall, etc., may be entered. As can be seen in FIG. 5, the user has selected that the fall occurred while running and onto concrete.

It is appreciated that the collected (or selected) data elements which are entered outside of the diagnosis section may provide information that is correlated to a specific code, such as an ICD-10 CM or PCS code. For example, some ICD-10 codes require a description of the mechanism of action for an injury (W01.198A). This information may be utilized to derive/locate a diagnosis code and/or may be provided to other portions of the medical data entry system where needed to provide information for obtaining a diagnosis code. Further, data points that may not be directly on point to terminology of a diagnosis/procedure code may be utilized to provide context when correlating the selected data to a code. For example, data regarding the height of a fall and the location of landing may provide contextual information regarding the severity of a fall. This information may be utilized to fill in or provide context to allow for the data entry system to suggest possible codes for selection (or to suggest additional data points needed to meet the elements of a particular code).

Figure 6:
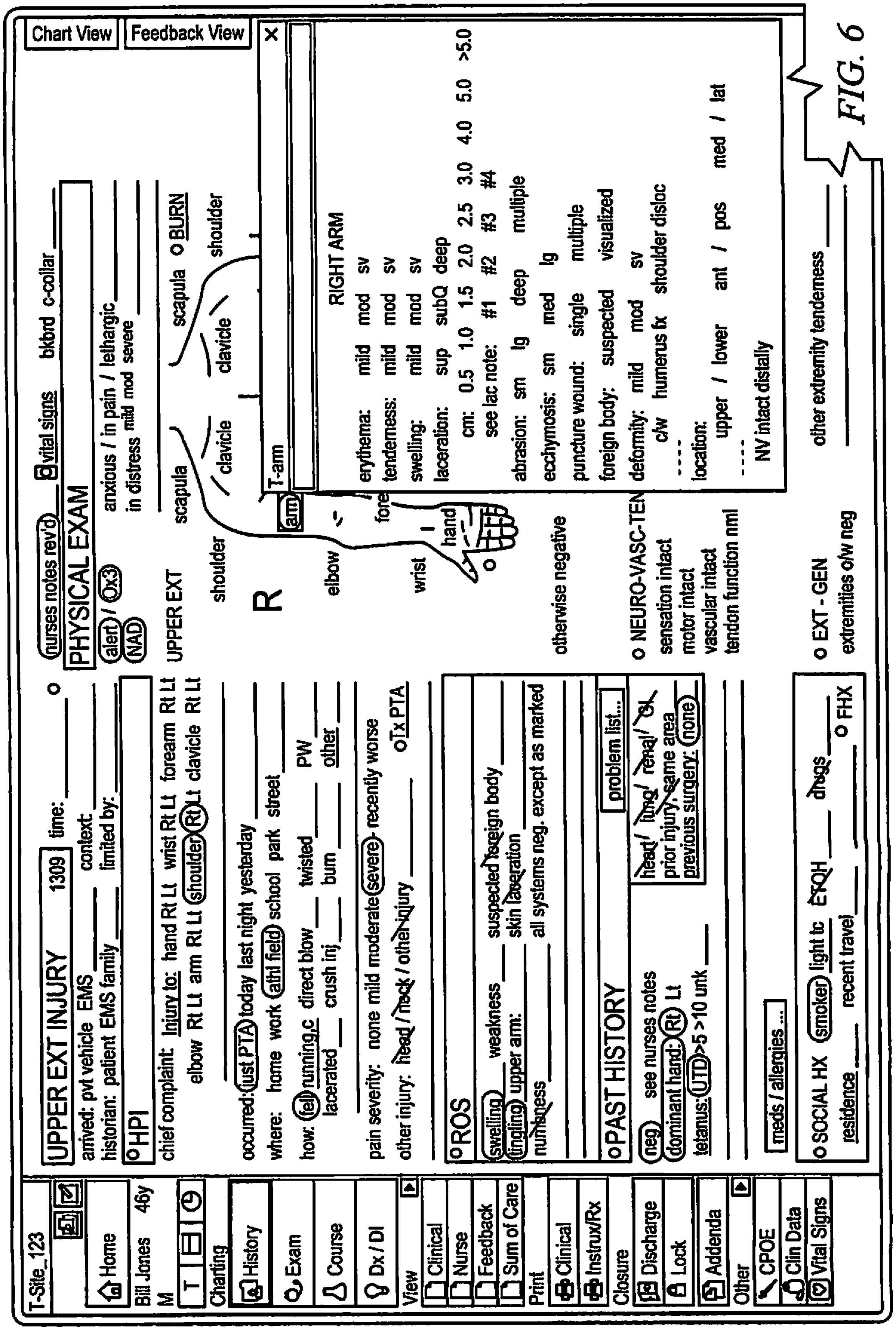
FIG. 6 illustrates an example display for a medical data entry program in accordance with an embodiment of the present application.

Referring now to FIG. 6, the user is now documenting data points from a physical examination of the patient. The user has clicked the entry for the right arm and has received a pop-up allowing for more information to be entered.

It is appreciated that as discussed above, the selection of "right arm" may be imported from other portions (such as a selection in the history portion) Likewise, if right arm was not selected in the history portion, the selection of data elements in the exam portion may backfill entries in the history. Further, any of such entries may be provided forward to the diagnosis/clinical impression sections and a medical professional may review such selections to determine whether they should remain selected for diagnosis purposes. For example, in codes regarding a broken arm, it is now required to specify whether the right or left arm has been injured. The selections discussed herein provide such information for coding. These data points, once entered in one portion, may be carried to other portions of the entry system such as other documentation sections, discrepancy checking sections and the like.

Figure 7:
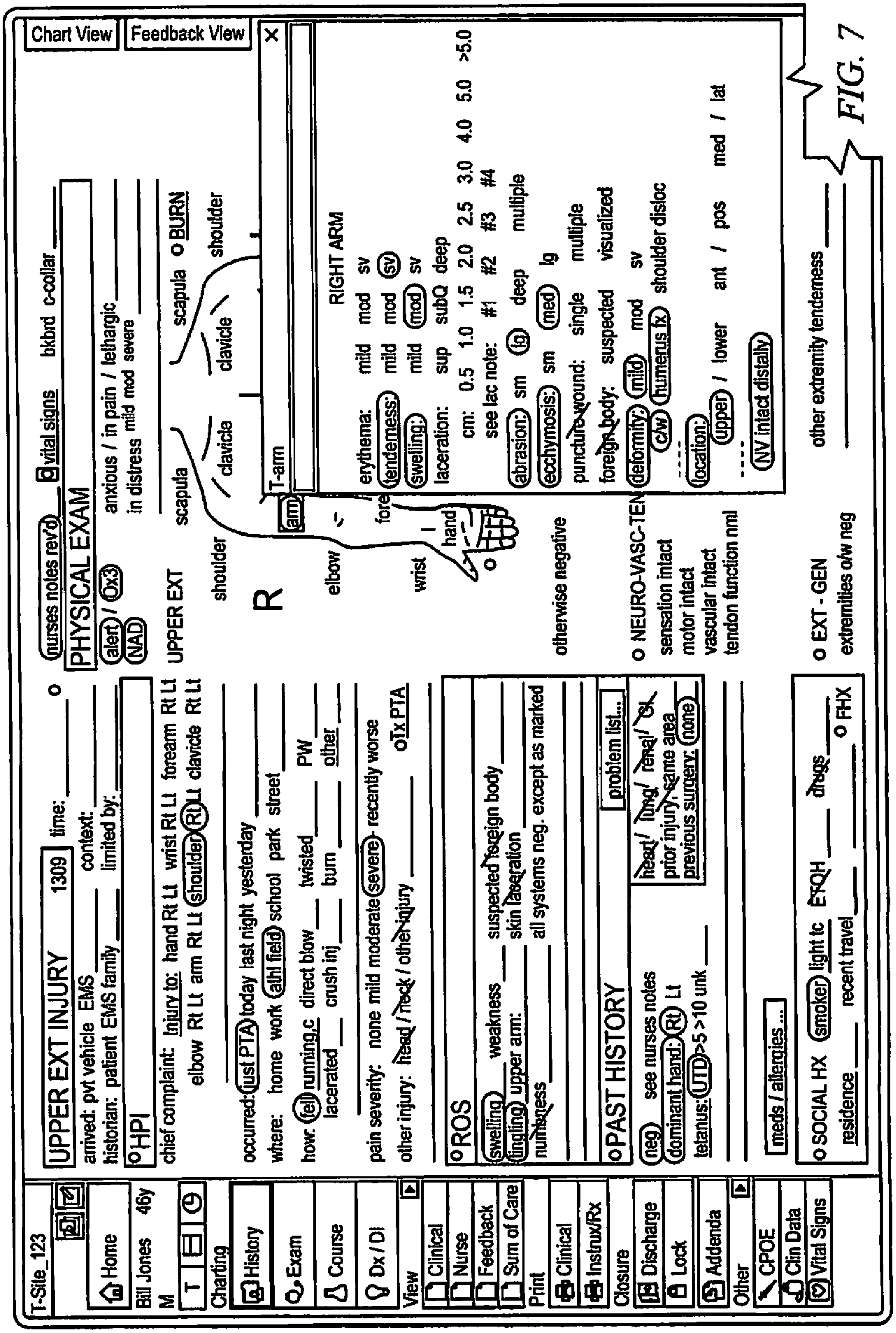
FIG. 7 illustrates an example display for a medical data entry program in accordance with an embodiment of the present application.

In FIG. 7 various selections in the right arm pop up shown on FIG. 6 are entered. The circles represent positive findings whereas the slashes represent negative findings. It is appreciated that a coder (or an automated program finding a code(s) which is most closely correlated with the entered information) could utilize the findings in the physical examination section even if full findings are not provided by a physician in a diagnosis. For example, the selection of "large abrasion" on the right upper arm could be associated with an ICD-10 code: S40.811A. Likewise, the ecchymosis (contusion) data point could be associated with: S40.021A.

Figure 8:
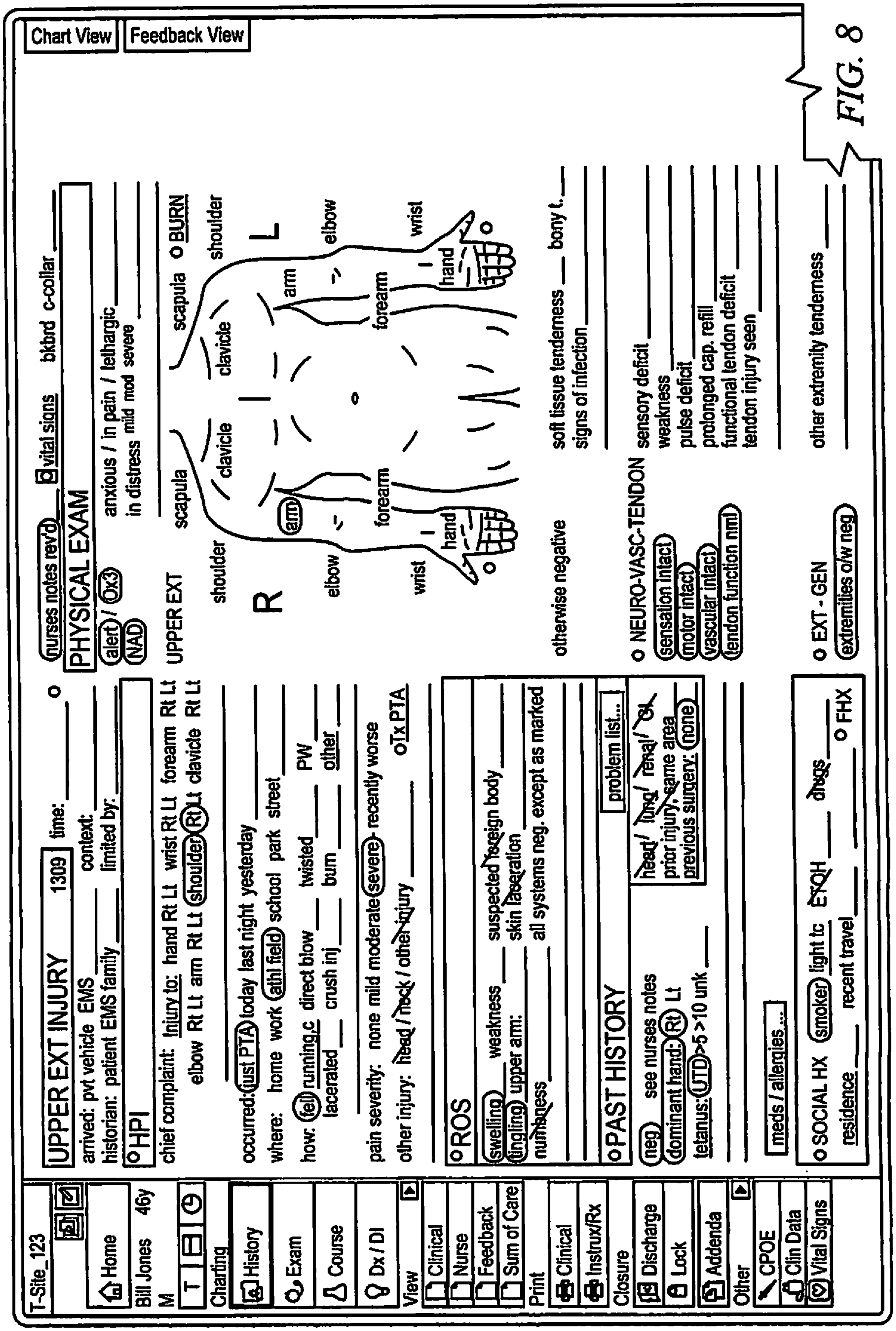
FIG. 8 illustrates an example display for a medical data entry program in accordance with an embodiment of the present application.

FIG. 8 illustrates the documentation of the history tab in completed form for the selected patient. At this point, a user may select the exam tab on the left side of the screen and display the exam template screen at FIG. 9 for the selected upper extremity injury medical complaint. In this case, additional physical examination details may be provided beyond what was provided on the first screen. For example in a fall/trauma example, while the right arm has been indicated as being broken, physical examination of the head, neck, respiratory system, etc., may also be warranted. This portion may function as described above with respect to the history screen. As such, entries on this screen may provide data points or context points to other portions of the system. Further, additional pop-up screens may be provided to capture further detail regarding the patient as described above.

Figure 10:
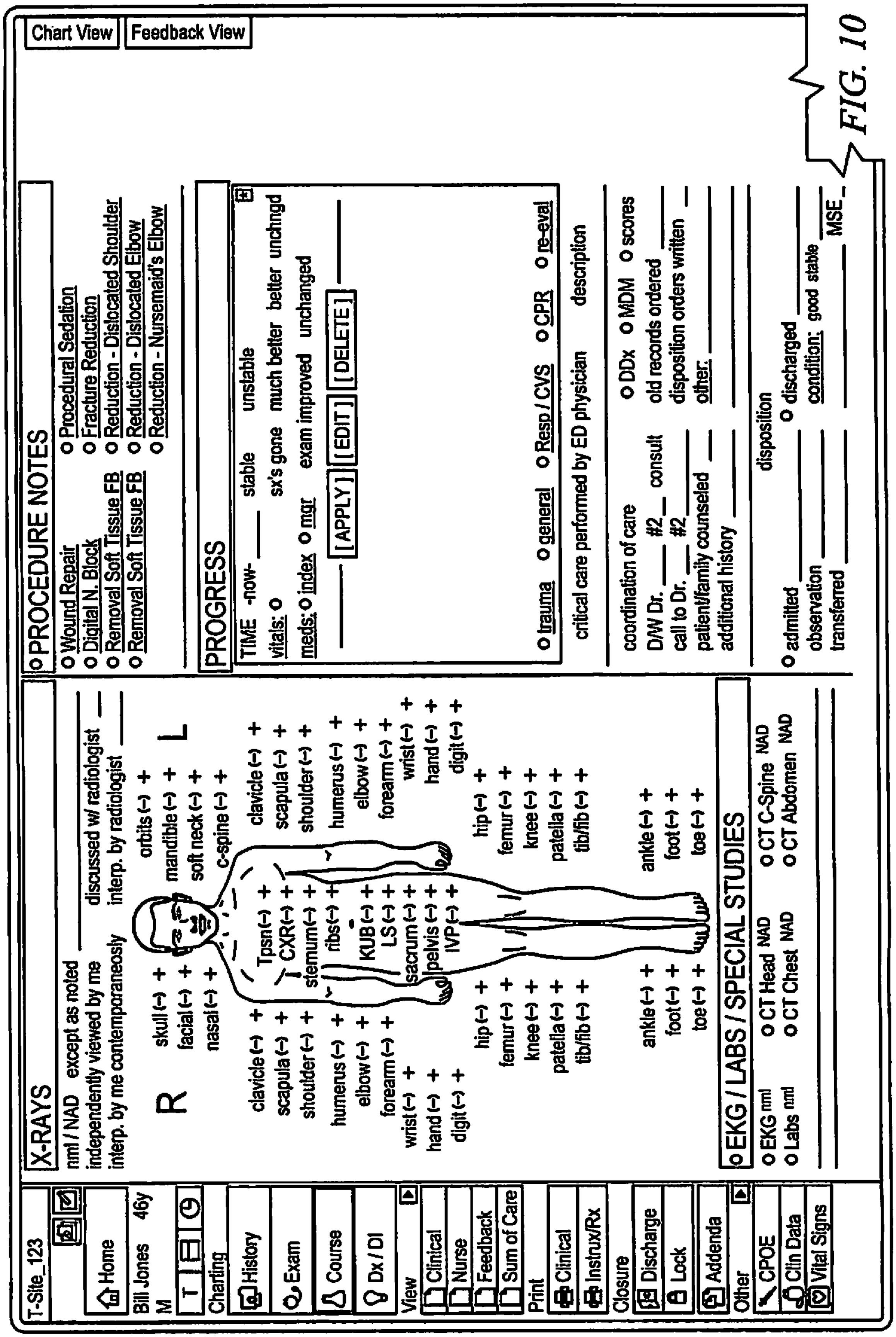
FIG. 10 illustrates an example display for a medical data entry program in accordance with an embodiment of the present application.
Figure 11:
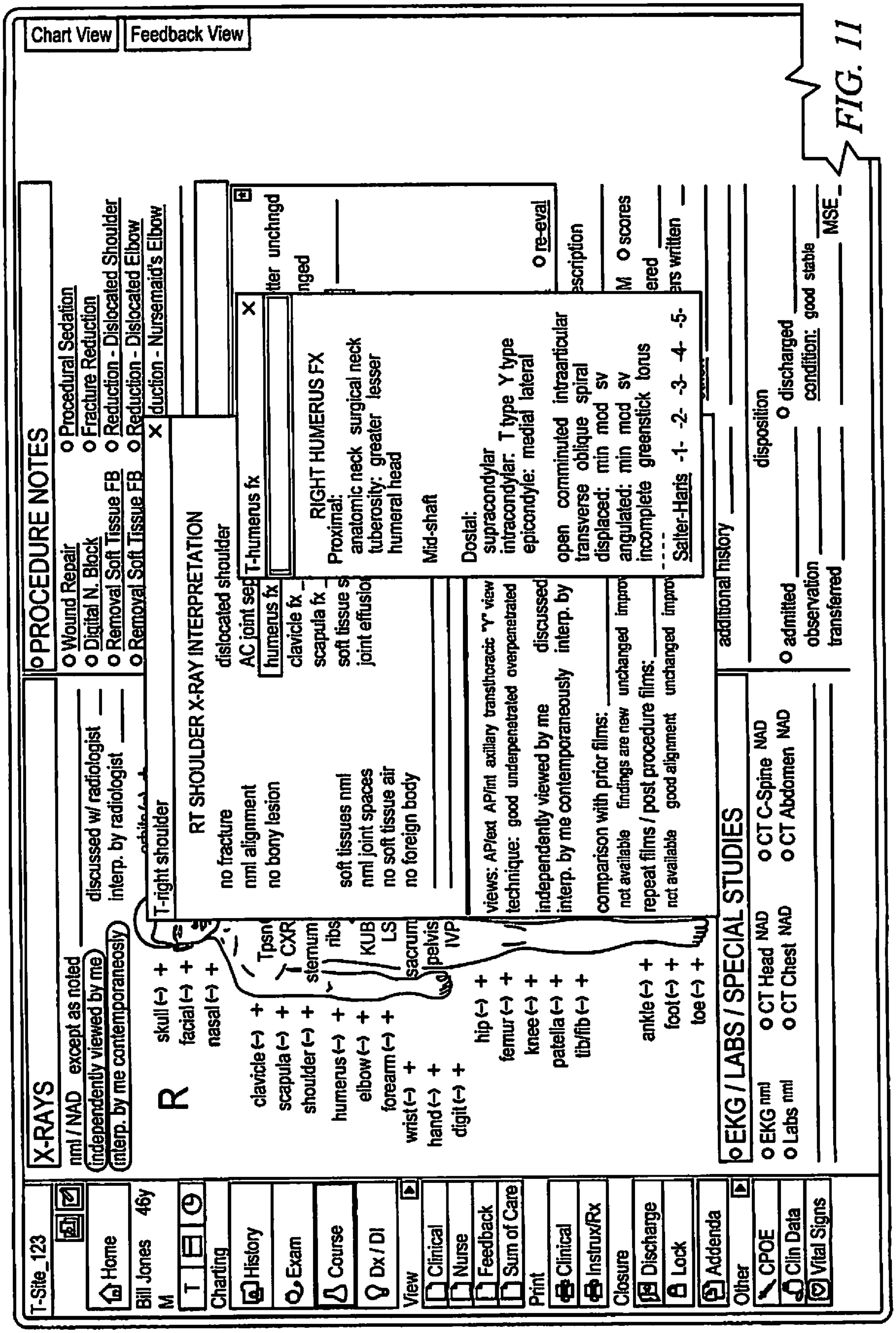
FIG. 11 illustrates an example display for a medical data entry program in accordance with an embodiment of the present application.
Figure 12:
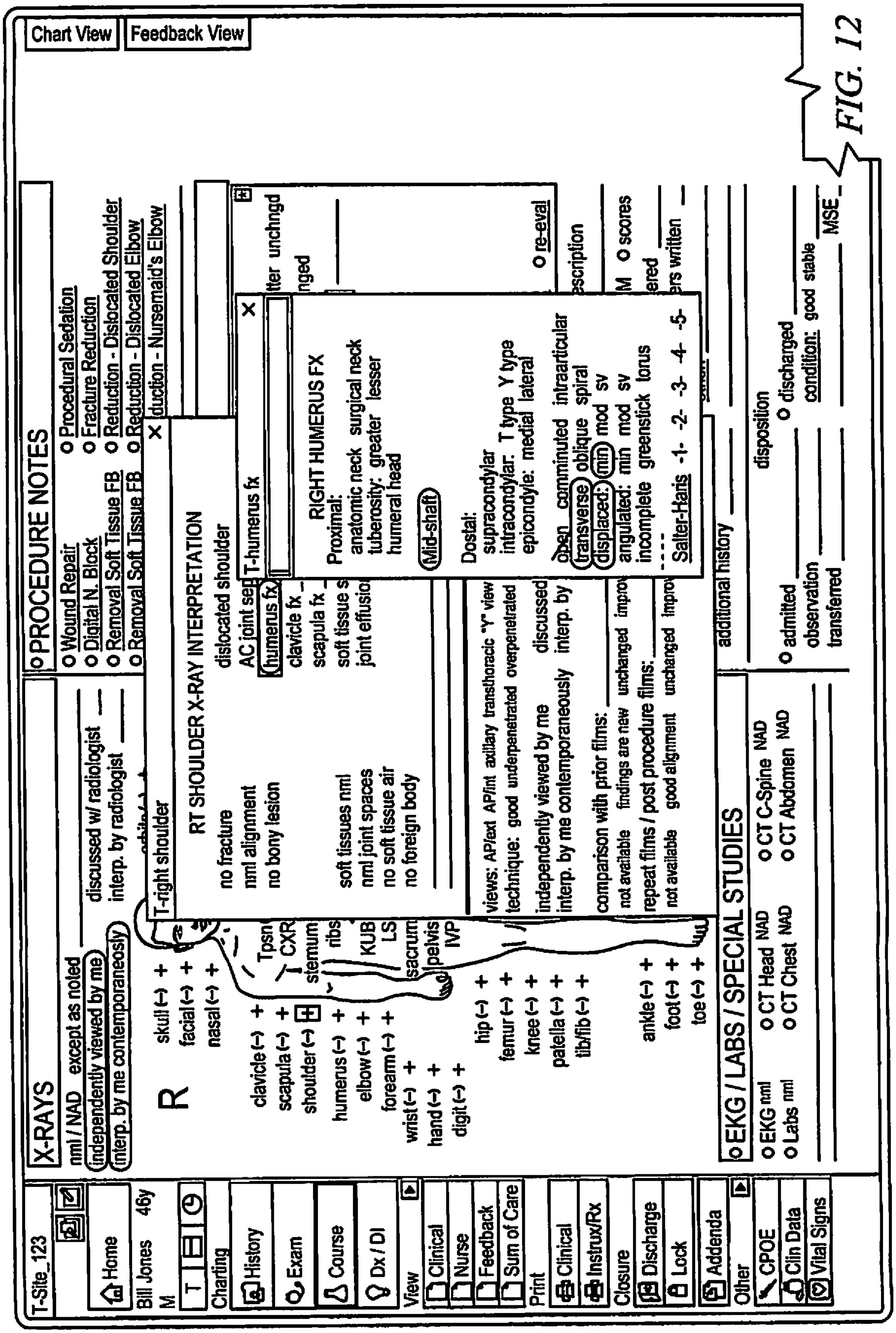
FIG. 12 illustrates an example display for a medical data entry program in accordance with an embodiment of the present application.
Figure 13:
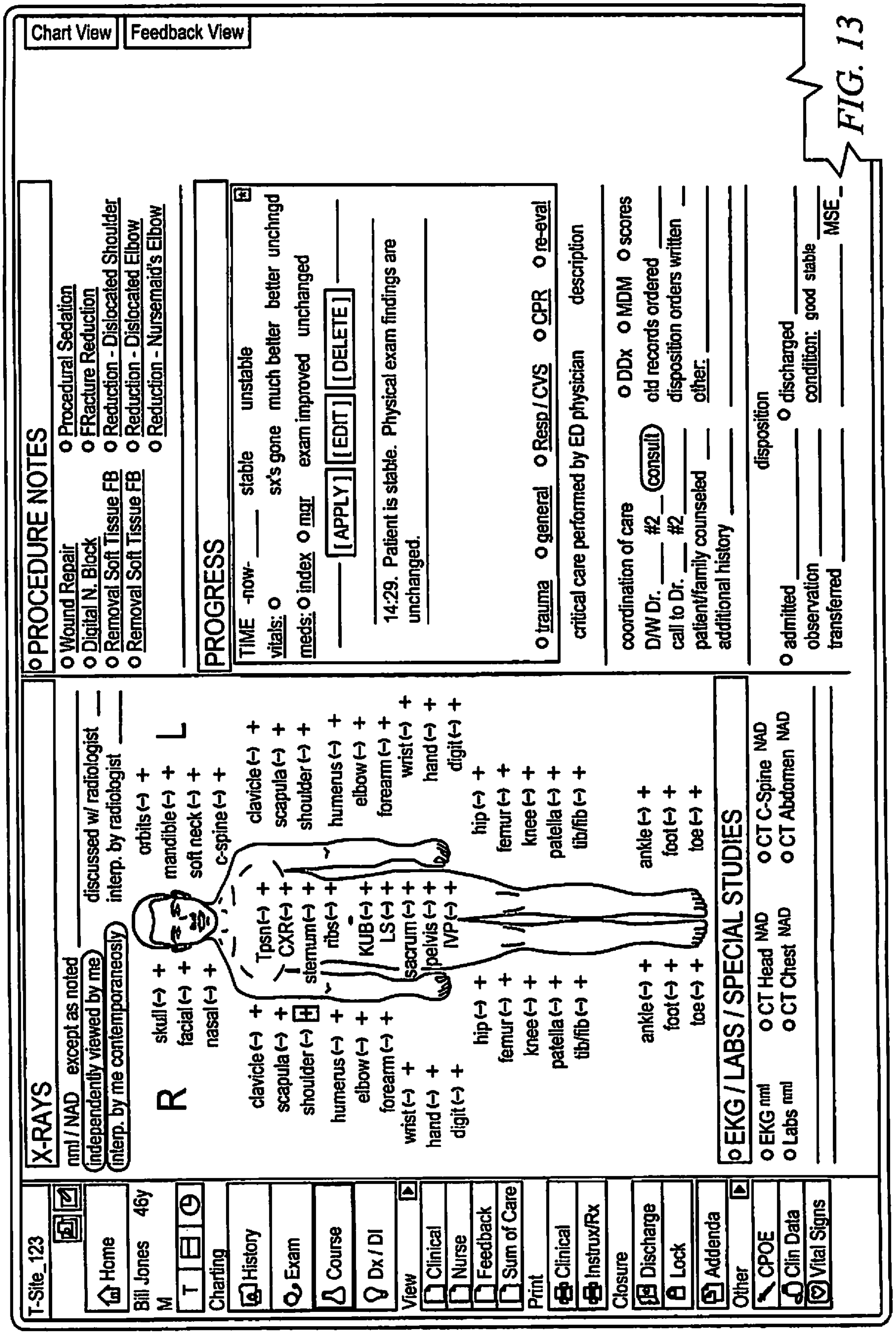
FIG. 13 illustrates an example display for a medical data entry program in accordance with an embodiment of the present application.

FIG. 10 illustrates the course template screen for the selected upper extremity injury medical complaint of FIG. 2. This page of the template may allow for the user to document test findings, such as for x-ray imaging results along with other notes regarding medical procedures for the patient. Referring to FIG. 11, when the user clicks the "+" sign next to "right humerus," a pop-up for the X-ray interpretation is opened and the user may click on the "humerus fracture" to make a selection. Additional detail may be entered for this selection (shown in FIG. 12) which further describes the fracture such as where the fracture is located, whether the fracture is open, and the like. It is appreciated that the humerus fracture entry and further entries represent further degrees of detail than illustrated in the previous two template screens which merely noted that a broken arm was present. As additional degrees of detail are obtained/documented, each detail may be provided to the diagnosis section for purposes of obtaining sufficient diagnosis code detail to obtain an accurate diagnosis code. A finalized course template form is illustrated at FIG. 13.

Figure 15:
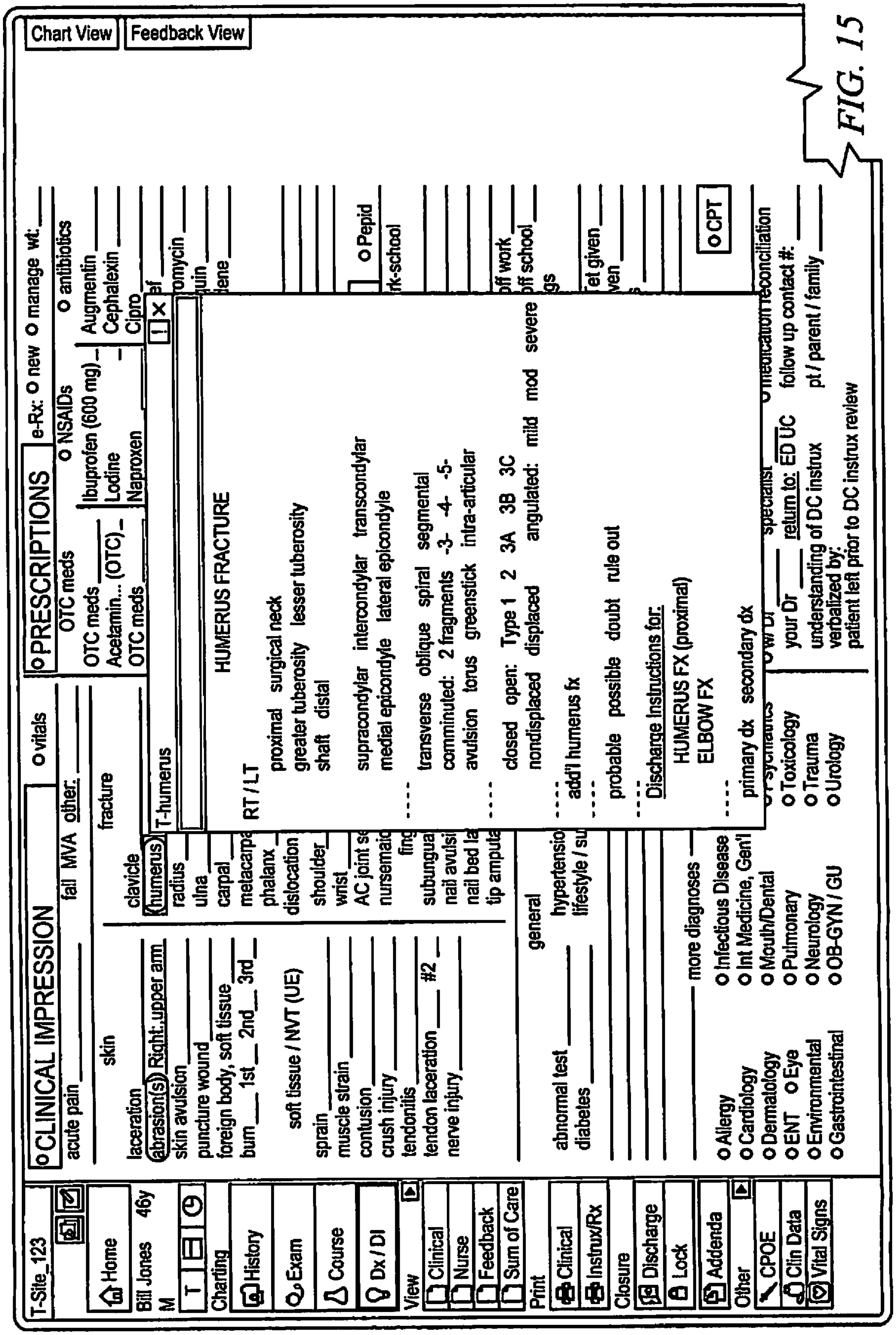
FIG. 15 illustrates an example display for a medical data entry program in accordance with an embodiment of the present application.

FIG. 14 illustrates the DX/DI template screen for the selected upper extremity injury medical complaint of FIG. 2. On this screen, a user may enter clinical impressions or diagnoses as well as document prescriptions and discharge instructions. In some embodiments, a large portion of the data provided in order to properly classify a diagnosis/procedure code may be entered and obtained/documented at this template screen. Referring to FIG. 15, the physician has entered information regarding clinical impressions. For example, an abrasion on the right upper arm is noted. Additionally, a humerus fracture has also been selected and a pop-up window having additional data elements pertaining to the humerus fracture is provided. As stated above, information regarding a humerus fracture may already be imported into the diagnosis screen. In another embodiment, indications that such information may be present may also be provided so as to notify the physician that specific information exists while still allowing the physician to enter the diagnosis himself or herself. Such a notification may be provided as a listing, a different form of selection (e.g. highlights over data items, greyed boxes, checkboxes and the like). It is appreciated that in some clinical scenarios medical professionals may select the DX/DI template screen and provide this information before documenting the history, exam, and test results as described previously. The order of such entries are not fixed in a particular manner. Further, as information from a history/exam entry portions may be forward populated, likewise DX/DI entries may be backward populated.

Figure 16:
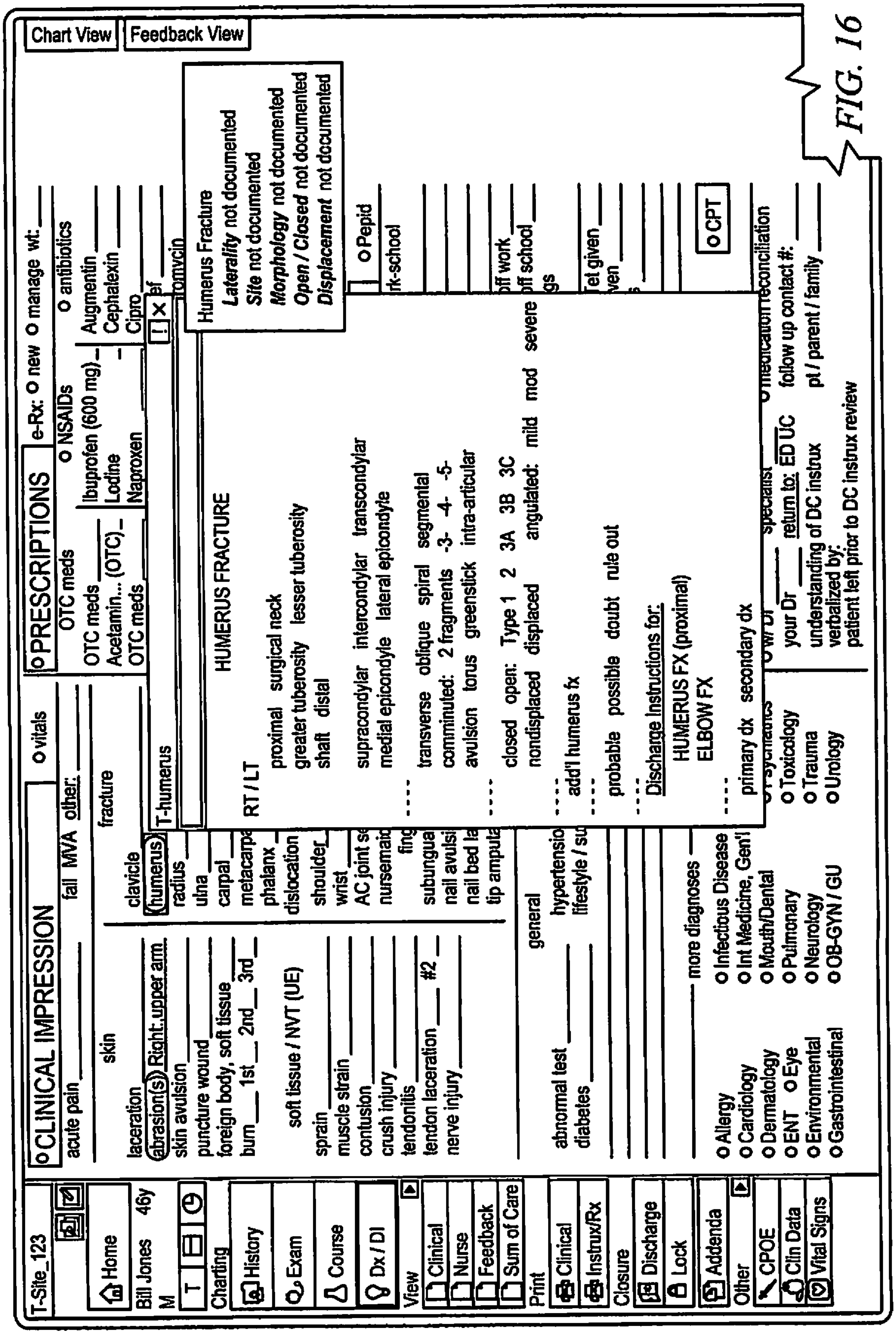
FIG. 16 illustrates an example display for a medical data entry program in accordance with an embodiment of the present application.

Upon selection of humerus fracture, the pop-up window provides detailed data items for selection. In the illustrated embodiment of FIG. 15, the pop-up window also includes an indication in the top right corner (in this case, an exclamation point) that connotes that insufficient information exists to select a fully specified diagnosis code. Upon clicking or hovering (or any other input indication) over the exclamation point as shown on FIG. 16, missing items pertaining to one or more diagnosis codes are listed. Such items may be individual items or may represent categories of items in which one or more data items should be selected. For example, the missing items include a selection as to whether the fracture is open or closed, whether the fracture is located on the right or left arm (laterality), etc. A physician will likely readily know the answer to these data elements, but would not necessarily have previously known that an answer was needed in order to provide adequate findings for obtaining a properly specified diagnosis code. Accordingly, embodiments may obtain data as part of a patient encounter. This data may be correlated with possible diagnosis codes to determine whether one or more codes could be selected. Once the possible codes are known, the system may prompt the physician to enter more information in order to refine the obtained/documented data and to further match a possible diagnosis code.

Figure 17:
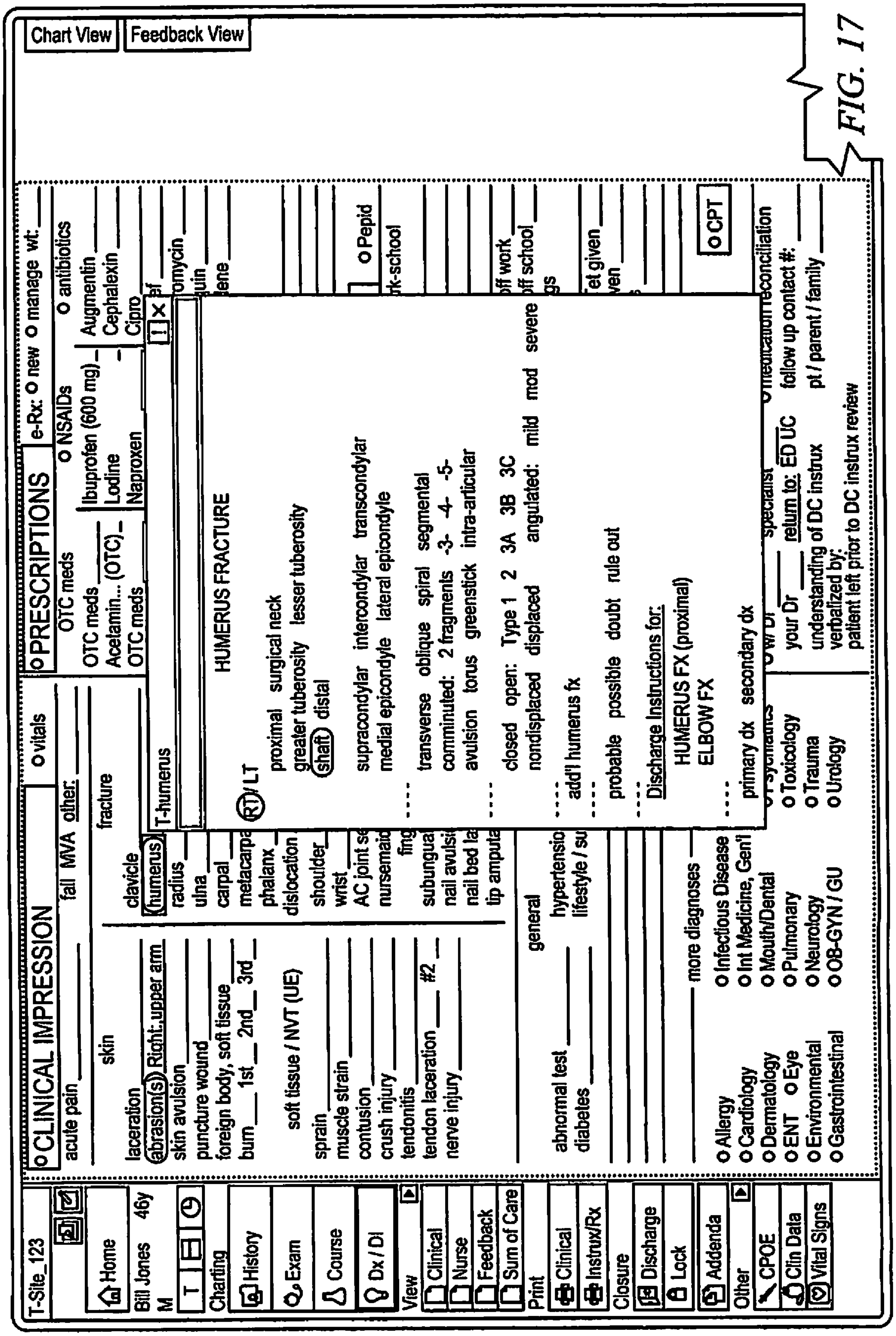
FIG. 17 illustrates an example display for a medical data entry program in accordance with an embodiment of the present application.
Figure 19:
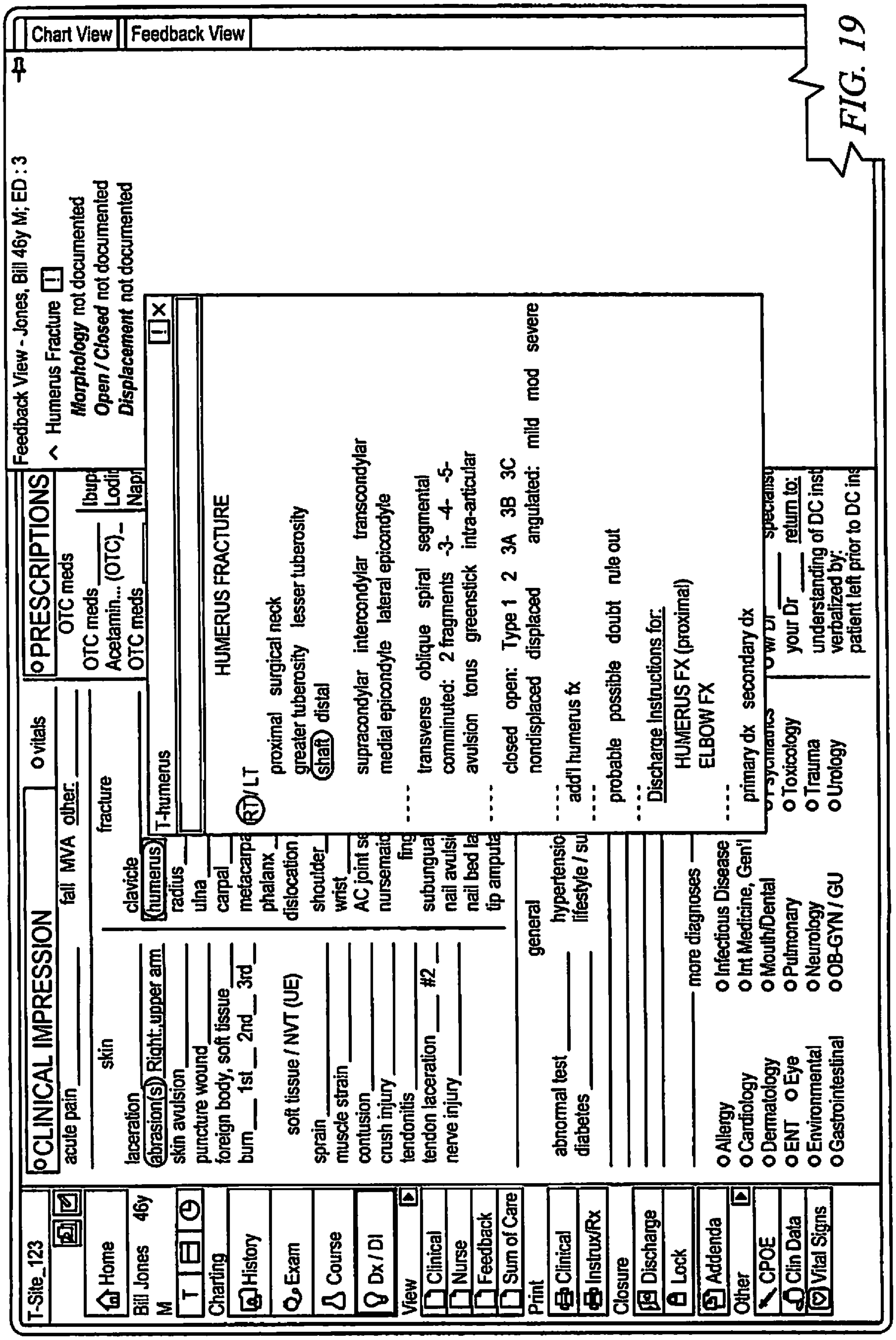
FIG. 19 illustrates an example display for a medical data entry program in accordance with an embodiment of the present application.

At FIG. 17, the user has selected that the fracture is on the right side of the patient and that site of the fracture is on the shaft portion of the bone. Accordingly, at FIG. 18 when the user clicks/hovers/etc. on the exclamation point, two of the previous entry categories are removed because appropriate data for matching a diagnosis code has been obtained. FIG.

19 illustrates an alternate embodiment where a separate frame may be utilized to track possible errors or deficient data. Such a frame may be provided outside of the detail pop up screens and may document where a user needs to enter additional data for clinical or coding purposes. In some aspects, the data in the side frame may be linked to particular areas in the entry system in order to allow a user to jump to an area to provide additional detail FIG. 20 illustrates another embodiment where deficiencies in received information are indicated to a user. In this example, a user may still click the exclamation point in the upper corner of the humerus fracture pop up window. However, as shown previously, the missing information may correspond to one or more categories of information of which at least one data item should be selected. Such categories may be highlighted in different colors or any other indication which distinguishes categories may be provided. In the illustrated example, in order to complete a correlated diagnosis code, the user must select at least one data entry point from each of the highlighted categories (although it is appreciated that some cases may require multiple selections within a category to fulfill the requirement and remove the highlight). For example, the user must indicate whether the broken humerus is open/closed, displaced/nondisplaced, etc. Therefore, deficient data entries may be gathered at or near the point of contact with the patient rather than based on additional or later knowledge.

Figure 21:
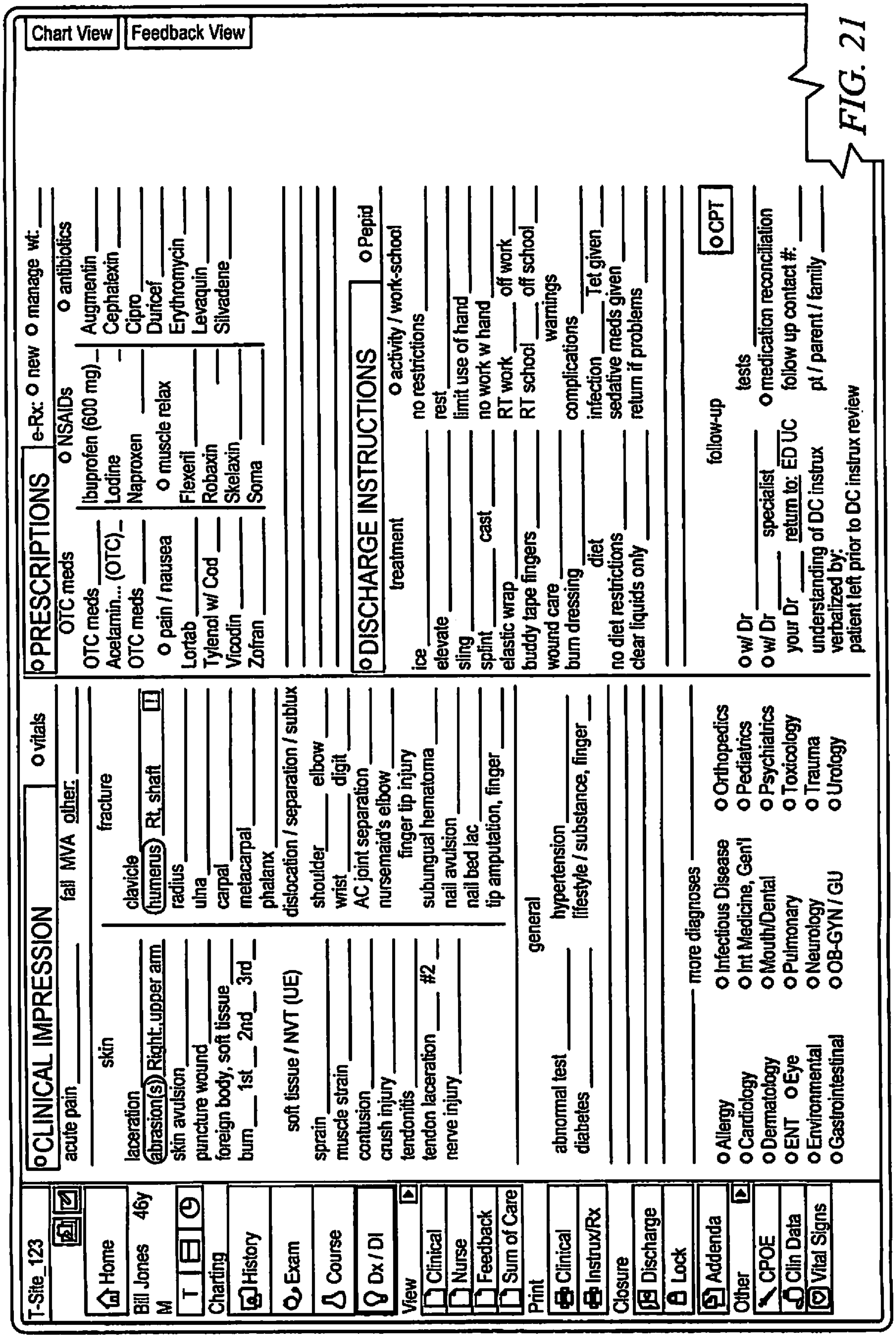
FIG. 21 illustrates an example display for a medical data entry program in accordance with an embodiment of the present application.

FIG. 21 illustrates an additional notification of deficiencies in entered data in accordance with another embodiment. After the humerus fracture content box has been closed, if there is no selection of data which has been indicated as missing, a notifier may be placed on the line item for the selected humerus fracture. This notifier may be implemented as an exclamation point as described with the previous example, whereupon a user may click or hover over the icon and see what information is missing. Further, clicking on the alert icon may link the user to a particular portion of the entry system where the missing information may be entered.

Figure 22:
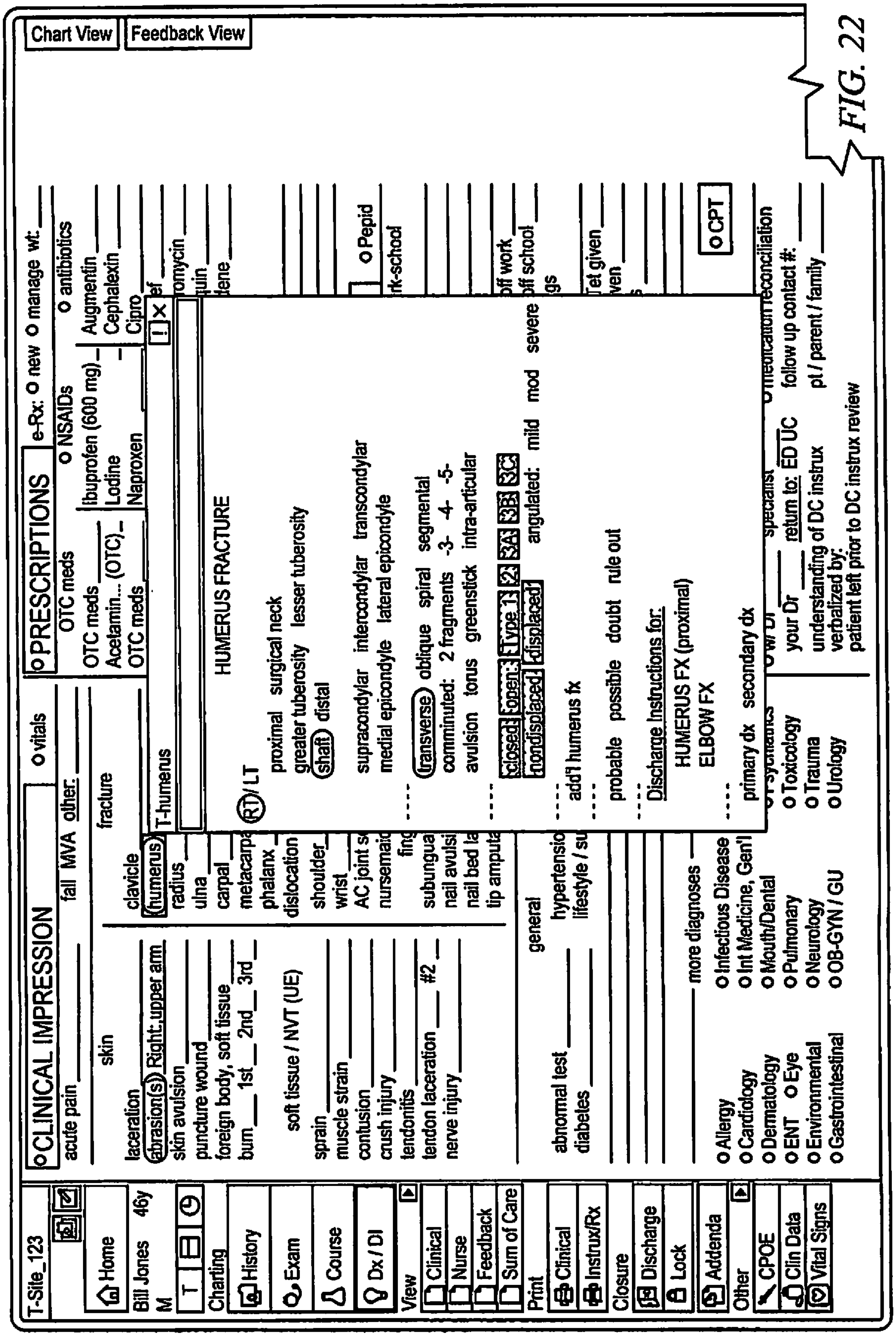
FIG. 22 illustrates an example display for a medical data entry program in accordance with an embodiment of the present application.

In the event that a user selects one or more items from within the highlighted categories of FIG. 20, the highlight of that category may disappear. For example, at FIG. 22 the user has selected the transverse data item, whereupon each of the other items in that category are no longer highlighted. The removal of the highlighting may indicate that a requirement for a specified diagnosis code has been satisfied. A user may continue to document/select items from within that group if appropriate. However, a disappearing highlight may symbolize that the present entry is sufficient for coding purposes.

Figure 24:
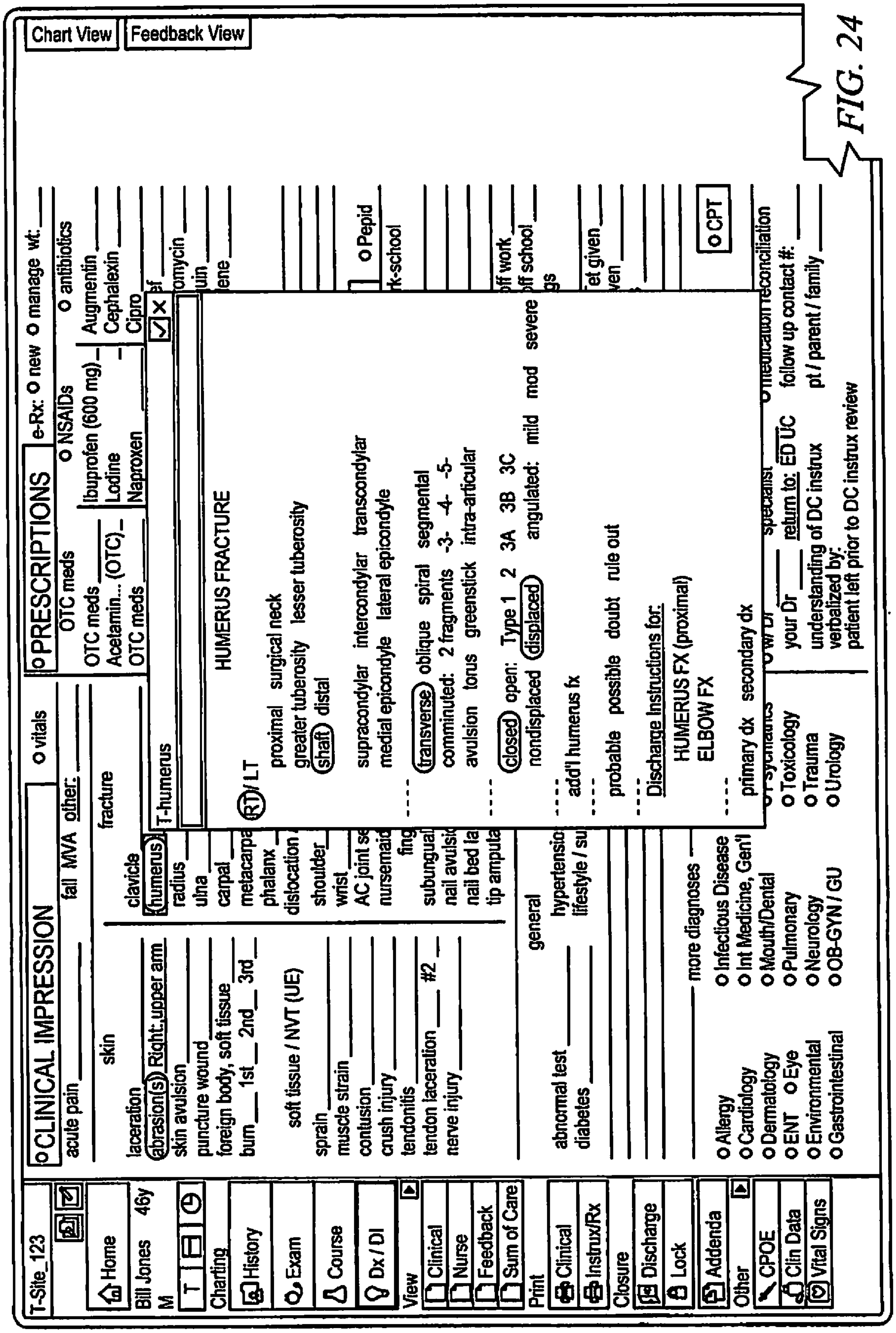
FIG. 24 illustrates an example display for a medical data entry program in accordance with an embodiment of the present application.

FIG. 23 illustrates additional categories being addressed by selecting the "closed" data point and FIG. 24 illustrates the final category being selected, whereupon all highlighted items have been addressed. In accordance with another embodiment, an indicator may be provided to the user to notify them that the appropriate data entry points have been received for generating a particular diagnosis code. This indicator may take any form. For example, in the illustrated embodiment the exclamation in the top right corner of the humerus fracture pop up window has been changed to a check mark icon to indicate that each requirement has been met.

It is noted that the illustrated embodiment is recognizing/correlating one diagnosis code with the data points being entered. In some instances multiple diagnoses may closely correlate with the received selections. In such circumstances, embodiments may add to the list of required items shown when hovering over the exclamation indicator. In some embodiments, multiple indicators may be given, each having their own listings of needed items that correspond to different diagnosis codes. Further, the marking or color coding of categories may include marking a first set of categories for a first diagnosis code and a second set for a second diagnosis code. Accordingly, the systems and methods described herein may be adapted to handle circumstances where multiple diagnoses exist and may function to notify a user when additional information is needed for the multiple diagnoses.

At FIG. 25, the physician may then complete the DX/DI template charting page for the patient encounter. This may include adding prescription information, discharge instructions, follow up recommendations, and the like.

Figure 26A:
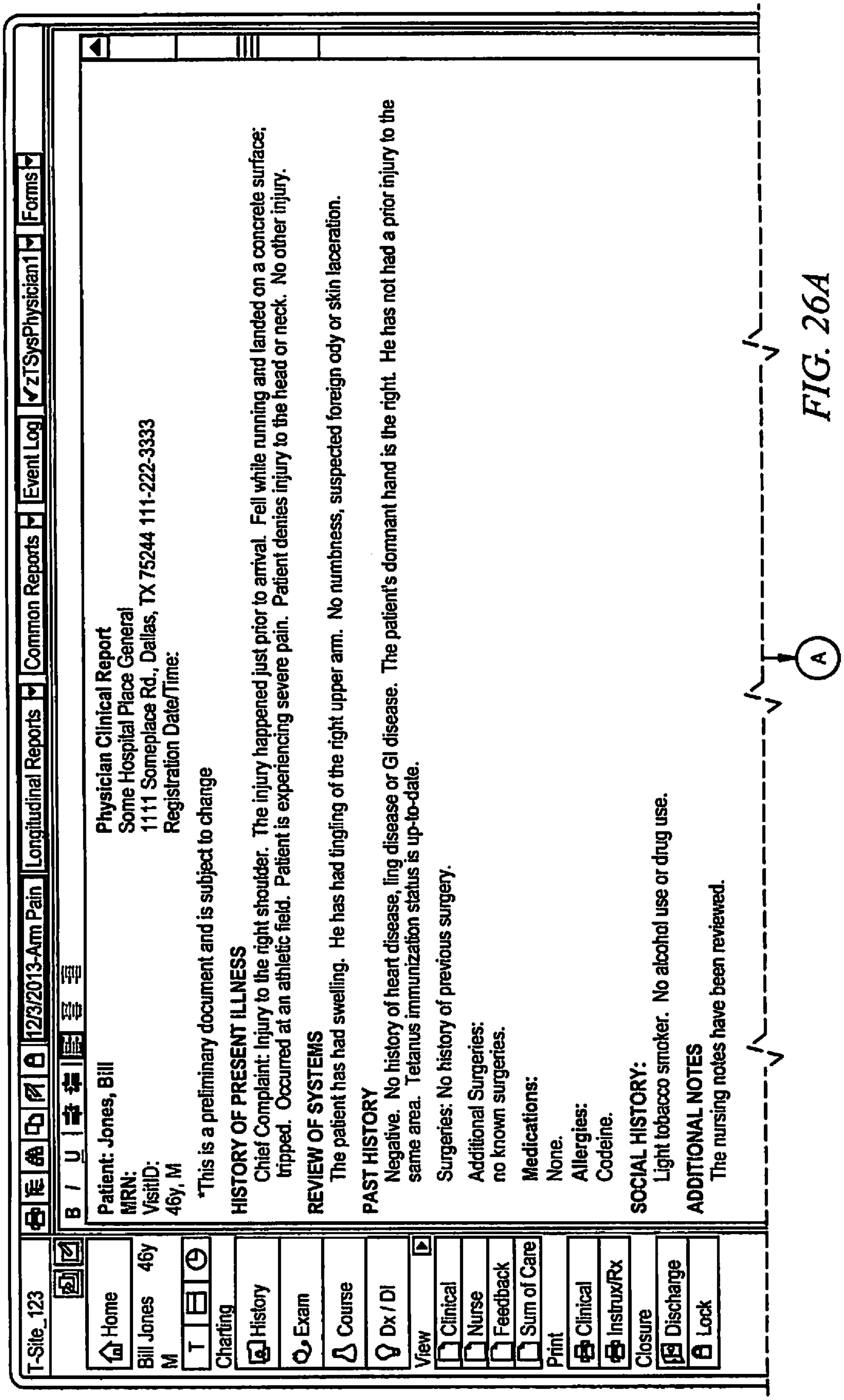

FIGS. 26 and 27 illustrate a medical report which is generated in response to the selected data elements which are selected throughout the course of the patient encounter. The line items of this report may be automatically generated and/or may be manually filled in by a medical professional, The information contained in the medical report may be further utilized by coding personnel to confirm or refine ICD-10 code selections. FIG. 28 illustrates instructions which may be given to a patient which contain pertinent information regarding the patient's diagnosis, recommendations/instructions for treatment and the like. Each of these reports may be automatically generated by the data entry system.

When the medical chart is ready to be finalized, embodiments may implement another error check procedure to ensure that all necessary data has been obtained/documented. For example, if deficiencies relating to procedures, regulatory requirements and/or diagnosis coding information exists, a feedback report may be generated and provided to a user. Such feedback may be in the form of an error report or may be provided in any other manner to conveniently notify the user of missing information/data points. FIG. 29 illustrates such a report for the example patient. In this example, there are no ICD-10 deficiencies or any other deficiencies in documentation. In the event that an error exists, a link to the appropriate portion of the data entry system may be provided in the error report in order to allow a user quick access to remedy the errors.

A coding summary report may also be generated at FIG. 30. It is appreciated that data relevant to coding may be summarized and provided in the illustrated report in a manner that it may be utilized by another individual to generate the codes while having all necessary information for a particular code. Further, in some aspects the diagnosis codes may be automatically generated in response to the data item selections. Such diagnoses may be provided to the physician or another medical professional for approval or confirmation.

It is appreciated that the above workflow example may be altered in many ways while still remaining consistent with inventive concepts described herein. For example, portions of the charting process may be skipped all together. Further, information regarding coding may only be obtained, correlated, etc., at the stage of filling out the diagnosis template page. Additionally, it is noted that the particular layout of various screens is provided as an example that facilitates quick and easy selection of selectable data items for a user. Other layouts and/or displays may be utilized.

Figure 31:
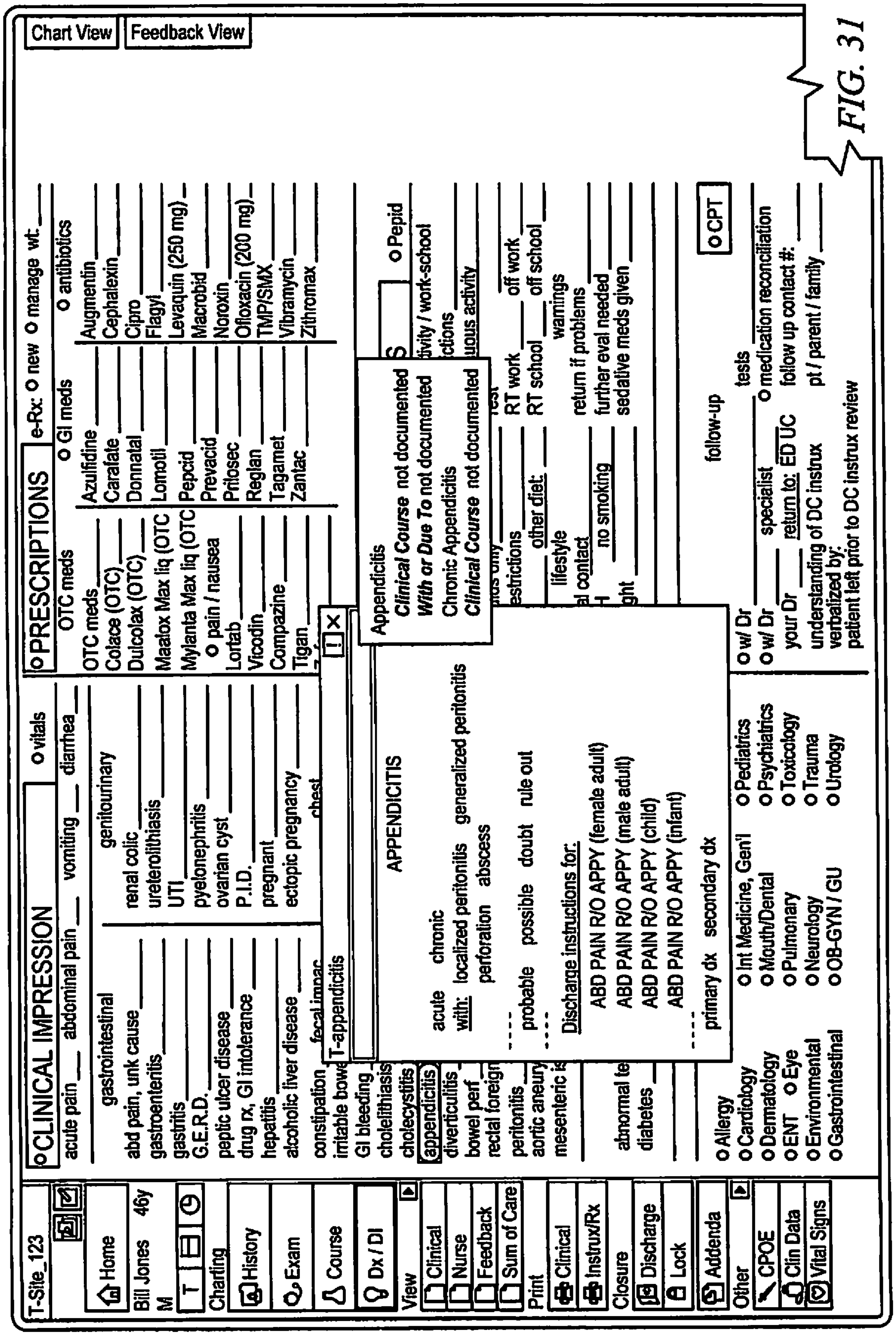
FIG. 31 illustrates an example display for a medical data entry program in accordance with an embodiment of the present application.

FIGS. 31-35 illustrate another example work flow in accordance with an embodiment of the present application. In this example, the chief medical complaint of "abdominal pain" from FIG. 2 has been selected. Referring to FIG. 31, in the DX/DI template screen the user has selected "appendicitis" which has caused a pop-up window to display. When clicking or hovering over the exclamation indicator in the pop-up window it can be seen that two different paths may be taken for providing the requisite information for different diagnosis codes. In one case, if the appendicitis is classified as "acute" additional information is needed, whereas if the appendicitis is classified as chronic, no other information is needed to correlate a particular diagnosis code.

Figure 34:
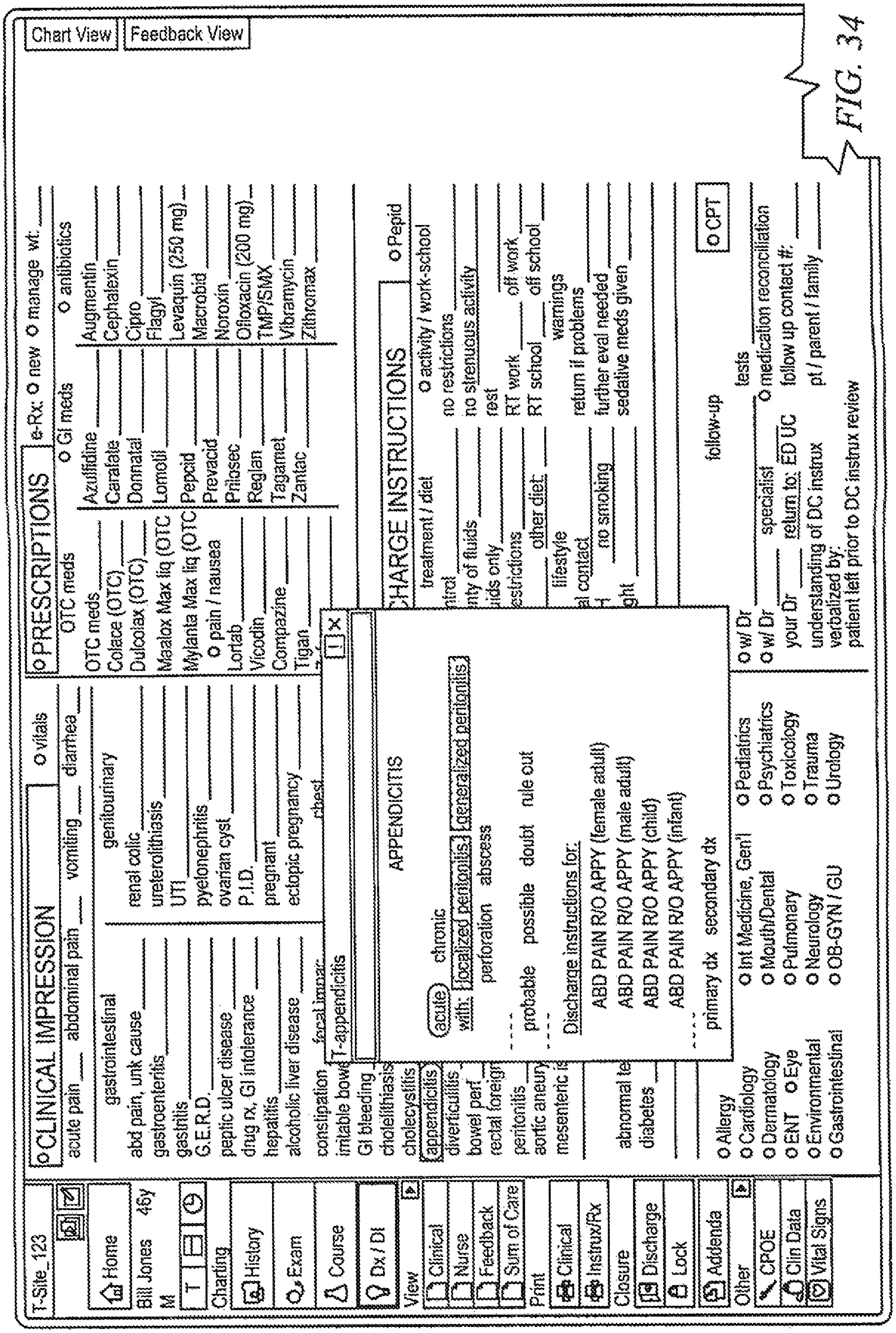
FIG. 34 illustrates an example display for a medical data entry program in accordance with an embodiment of the present application.
Figure 35:
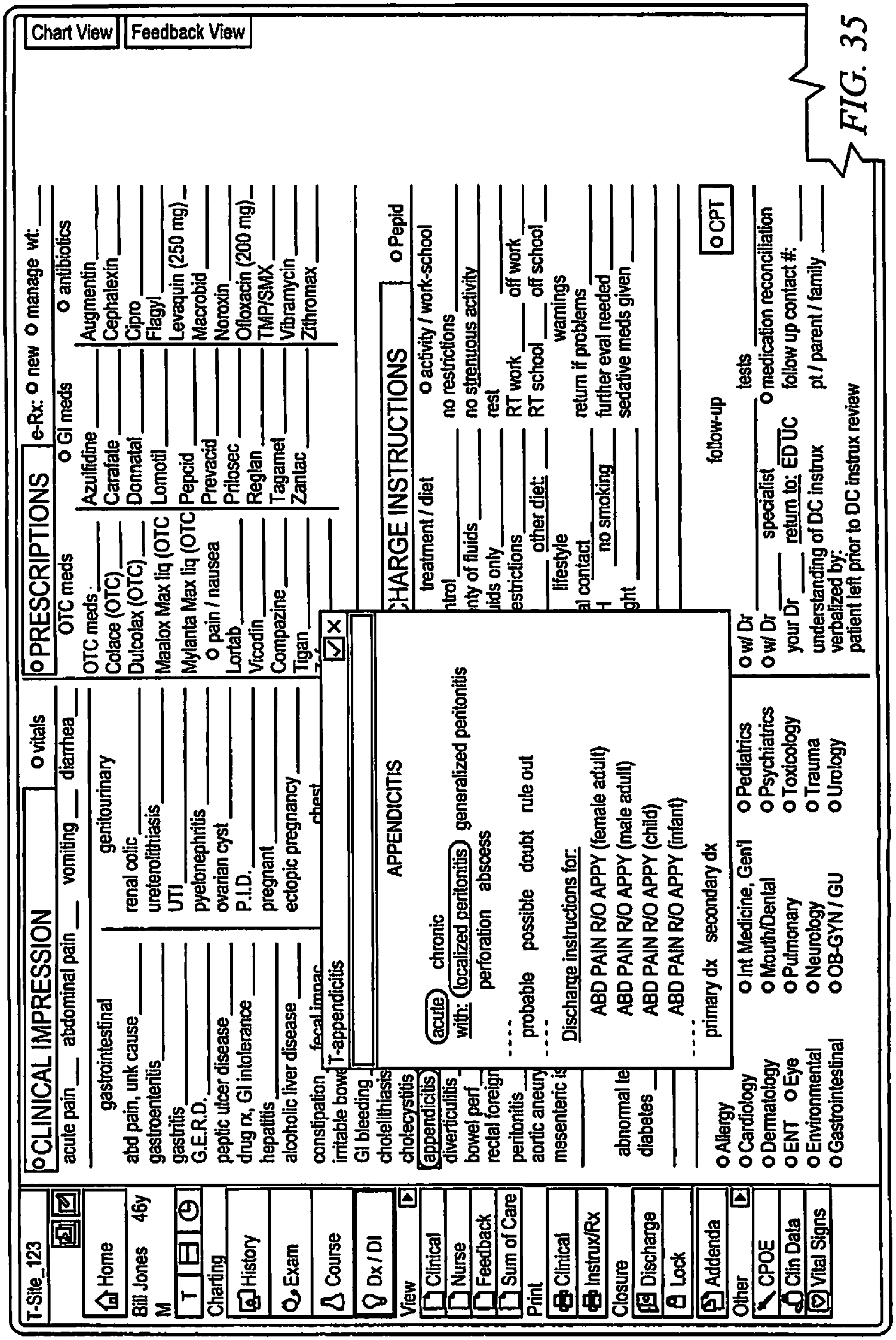
FIG. 35 illustrates an example display for a medical data entry program in accordance with an embodiment of the present application.

At FIG. 32, upon the user attempting to close a window, color coded required field selections become highlighted. It is appreciated that the second category is optional depending on the selection of acute or chronic appendicitis. In the event that "chronic" is selected (e.g. FIG. 33), the highlights on the second category may be removed and the exclamation indicator changes to a check mark to illustrate a positive correlation between entered data and a diagnosis code. Alternatively, as shown in FIG. 34, if "acute" is selected the second category of data remains highlighted and upon making a selection within the second category, highlights on the second category may be removed and the exclamation indicator changes to a check mark to illustrate a positive correlation between entered data and a diagnosis code as shown in FIG. 35.

In view of exemplary systems and functionality shown and described herein, methodologies that may be implemented in accordance with the disclosed subject matter will be better appreciated with reference to various functional block diagrams. While, for purposes of simplicity of explanation, methodologies are shown and described as a series of acts/blocks, it is to be understood and appreciated that the claimed subject matter is not limited by the number or order of blocks, as some blocks may occur in different orders and/or at substantially the same time with other blocks from what is depicted and described herein. Moreover, not all illustrated blocks may be required to implement methodologies described herein. It is to be appreciated that functionality associated with blocks may be implemented by software, hardware, a combination thereof or any other suitable means (e.g., device, system, process, or component). Additionally, it should be further appreciated that methodologies disclosed throughout this specification are capable of being stored on an article of manufacture to facilitate transporting and transferring such methodologies to various devices. Those skilled in the art will understand and appreciate that a methodology could alternatively be represented as a series of interrelated states or events, such as in a state diagram.

Figure 36:
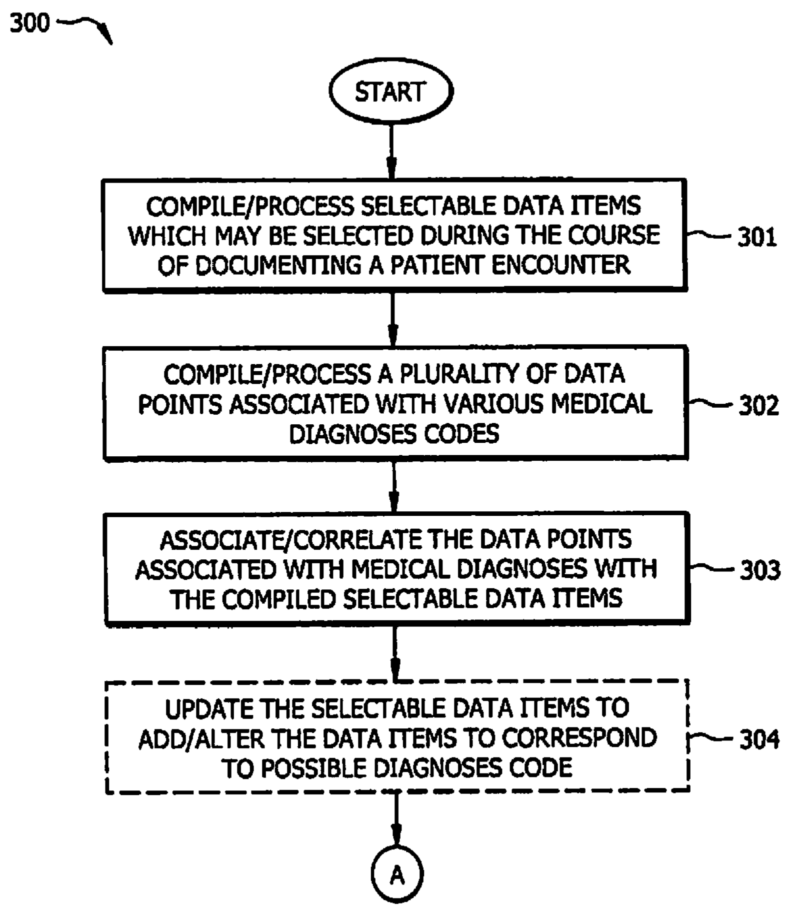
FIG. 36 illustrates a methodology operable on one or more processing devices for obtaining one or more diagnosis codes.

In accordance with one or more embodiments, with reference to FIG. 36, there is shown a methodology 300, operable on one or more processing devices for obtaining one or more diagnosis codes. Specifically, method 300 may involve, at 301 compiling or processing selectable data items which may be selected during the course of documenting a patient encounter. Such compiling may include determining what specific data items are present and determining what relations such data items have with each other. Method 300 may further include, at 302, compiling/processing a plurality of data points associated with medical diagnoses codes. For example, specific requirements for specific codes may be determined such as the requirement to specify which side of the body has a broken bone, etc.

At step 303, method 300 includes associating and/or correlating the data points associated with medical diagnosis and/or procedure codes of 302 with the compiled selectable data items of 301. Once the data points and delectable data items are associated with each other, systems may then monitor selected items and begin associating or predicting a possible code, and therefore prompt the user regarding whether additional data is needed, or if sufficient data has been received to generate a fully specified code.

Method 300 further includes optional step 304 which allows a system to update the selectable data items to add or alter these data items in order to closer correspond to a possible code. For example, if a diagnosis code requires a specific finding to be selected by a user, method 300 may add a selectable data element to the documentation system in order to allow for the selection of that finding.

Figure 37:
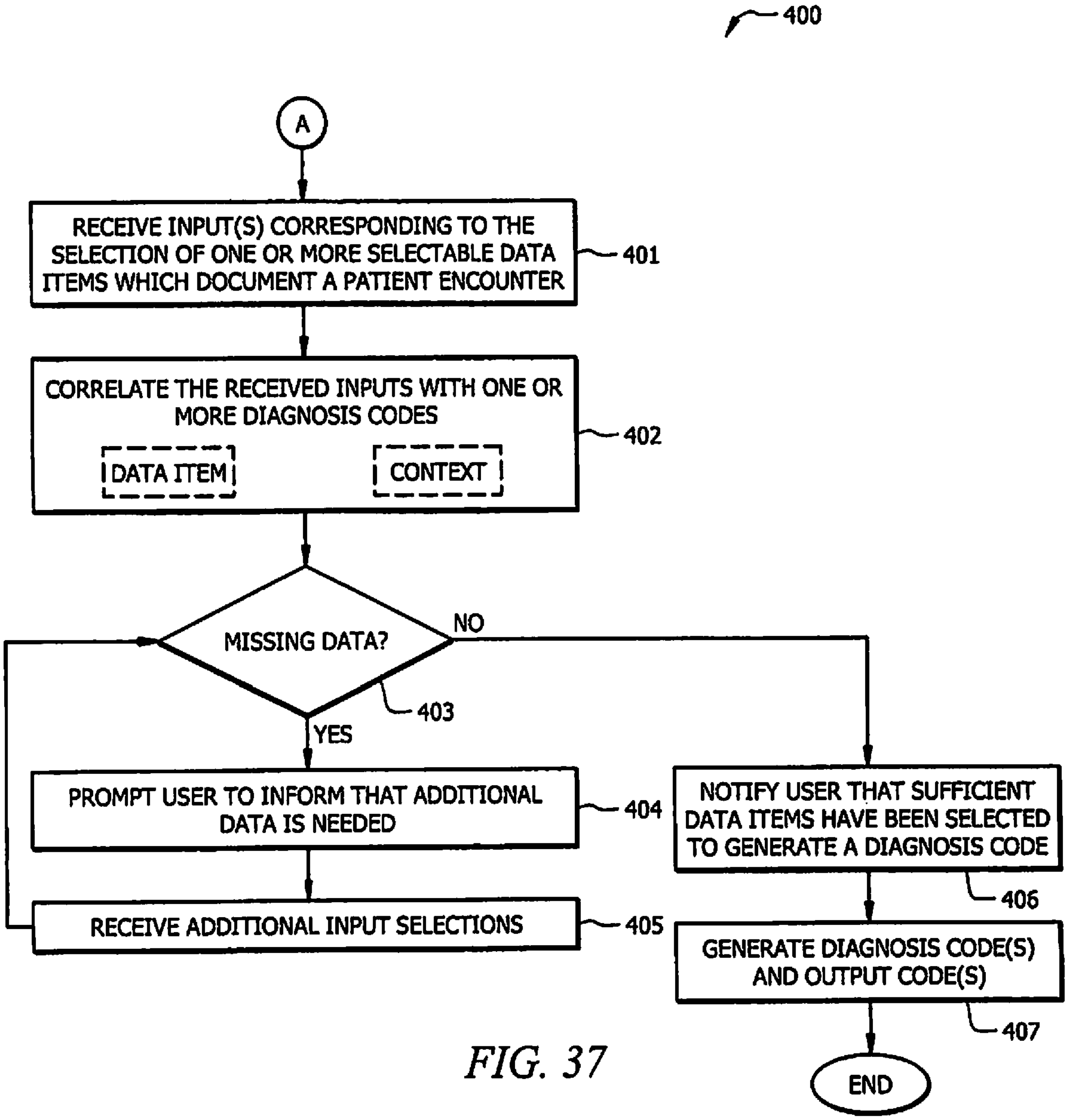
FIG. 37 illustrates a methodology operable on one or more processing devices for obtaining one or more diagnosis codes.

In accordance with one or more embodiments, with reference to FIG. 37, there is shown a methodology 400, operable on one or more processing devices for obtaining one or more diagnosis codes. It is noted that method 400 may be implemented as a continuation to method 300, or may be implemented separately. Method 400 may involve, at 401, receiving one or more inputs at a processing device that correspond to the selection of one or more selectable data elements which are selected to document a doctor-patient encounter. Such selections may be similar to those described above with respect to the charting application illustrated in FIGS. 1-35.

At step 402, method 400 includes correlating the received inputs with one or more diagnosis codes. It is appreciated that this correlation may include point to point correlation where selected data points align with required information for a diagnosis and/or procedure code. Alternatively or additionally, a contextual analysis of one or more inputs may be utilized to correlate the inputs to a code. For example, the finding of a diagnosis or procedure code may be seen as a dynamic calculation. Multiple selected items may include or exclude various diagnosis codes. For example, selecting a chief medical complaint of "abdominal pain" will likely rule out diagnoses that correspond to non-related issues such as a broken leg. Accordingly, a selection while not being directly on point with a diagnosis code, still provides contextual information. As a user selects additional items, target codes may be narrowed, changed, etc., which in turn may change the type of information that a user may be prompted to input in order to complete the information needed to generate a code.

At 403, method 400 determines whether there is missing data, e.g. whether the current selection of data items is insufficient to meet the elements of a fully specified diagnosis and/or procedure code. If there is missing data, at 404 a user may be prompted to provide additional data. This may be implemented in any manner which provides sufficient notification, e.g. as described above with respect to the exclamation point notification and/or color coded missing field indicators. Additional input selections may then be received at a processing device at step 405. Once there is no missing data (e.g. sufficient information exists to specify one or more diagnosis codes), a notification may be sent to the user that sufficient data items have been collected to generate a fully specified code at 406. Such a notification may be an affirmative notification or may be in the form of removing a notification that insufficient items have been selected.

In some embodiments, step 407 may be provided wherein a processing device may automatically generate one or more diagnosis codes and output these codes to a user or other processing device. Such a step is optional as the entered data may be sent to a coder who then manually selects and generates the codes.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed:

1. A method for controlling elements of a graphical user interface (GUI) for a medical data entry system, said method comprising:

providing a processing device having a first GUI element, the processing device configured to receive an input relating to a clinical concept, wherein the clinical concept is associated with a diagnosis code; and wherein the diagnosis code is associated with a data requirement;

determining at the processing device, in receipt of the input, whether the data requirement is met to associate the clinical concept with the diagnosis code;

designating the diagnosis code as a fully specified diagnosis code when the data requirement is met;

generating, in response to receiving the input and in response to determining that the data requirement is not met to associate the clinical concept with the diagnosis code, a second GUI element on the processing device configured to present a selectable data item adapted to include a positive selection state and a negative selection state, the selectable data item corresponding to the data requirement, the second GUI element configured to indicate whether the data requirement is met;

determining at the processing device, in response to the selection of the selectable data item, whether the data requirement has been met to associate the clinical concept with the diagnosis code, wherein determining whether the data requirement is met to associate the clinical concept with the diagnosis code comprises iteratively obtaining additional inputs associated with the clinical concept until a stop condition is met; and evaluating each of the additional inputs against a plurality of diagnosis codes;

excluding one or more of the plurality of diagnosis codes from the evaluating each of the additional inputs step based on the additional inputs;

designating the stop condition as met upon identification of the diagnosis code from the plurality of diagnosis codes that corresponds to the clinical concept and is identified based on the additional inputs;

configuring the second GUI element based on determining, in response to the selection of the selectable data item, to one of a first state indicating the data requirement has not been met and a second state indicating the data requirement has been met;

executing, in response to determining that the data requirement has not been met, a GUI control adapted to require a user to positively or negatively select the selectable data item such that the data requirement is met to associate the clinical concept with the diagnosis code;

wherein executing the GUI control includes activating a graphical indicator on the second GUI element indicating that the data requirement has not been met;

providing a feedback report to the user in response to receipt of a selection of the selectable data item;

wherein the feedback report identifies a deficiency in received data to generate the fully specified diagnosis code;

designating the diagnosis code as the fully specified diagnosis code in response to determining that the data requirement has been met; and updating the graphical indicator to display an indication that the data requirement has been met to designate the diagnosis code as the fully specified diagnosis code.

2. The method of claim 1, wherein different inputs are received during each iteration.

3. The method of claim 1, wherein at least some of the additional inputs are unrelated to generation of a diagnosis but are related to associating the clinical concept with the diagnosis code.

4. The method of claim 1, wherein the plurality of diagnosis codes correspond to payer codes.

5. The method of claim 1, wherein the graphical indicator is configurable to open a third GUI element displayed simultaneously with the second GUI element, and wherein the third GUI element identifies an additional data item to designate the diagnosis code as the fully specified diagnosis code, the method further comprising.

6. The method of claim 1, wherein the graphical indicator is configurable to open a third GUI element displayed simultaneously with the second GUI element, and wherein the third GUI element identifies an additional data item to designate the diagnosis code as the fully specified diagnosis code, the method further comprising:

updating the third GUI element in response to receiving the additional data item.

7. The method of claim 1, further comprising:

initiating, in response to determining that the data requirement has been met, a notification to indicate that sufficient data is available to associate the clinical concept with the diagnosis code;

determining, based on the selection of the selectable data item, that the data requirement has been met; and automatically applying, in response to determining that the data requirement has been met, a second control command to the second GUI to enable closing of the second GUI element.

8. The method of claim 1, wherein the data requirement includes one or more categories each having a selectable data item, and wherein the data requirement is considered met when the selectable data item from each of the one or more categories has been positively or negatively selected.

9. The method of claim 1, wherein the data requirement includes one or more categories each having a selectable data item, and wherein the data requirement is considered met when the selectable data item from each of the one or more categories has been positively or negatively selected; and further comprising:

notifying a user when the data requirement has been met by the positive or negative selection of the selectable data item from each of the one or more categories; and wherein the notifying a user includes providing the fully specified diagnosis code to the user.

10. The method of claim 1, wherein iteratively obtaining the additional inputs associated with the clinical concept until a stop condition is met further comprises changing a type of additional inputs prompted to be entered to generate the fully specified diagnosis code.

11. The method of claim 1, further comprising:

backfilling one or more entries in an examination history based on selections of a selectable data item in the GUI.

12. The method of claim 1, further comprising backfilling one or more entries in an examination history based on selections of a selectable data item in the GUI; and carrying the selection of the selectable data item forward as additional sections of the GUI are presented.

13. The method of claim 1, further comprising:

indicating, in response to the selection of the selectable data item, that the data requirement has been met by removing highlighting from items rendered on the GUI.

14. The method of claim 1, wherein the step of determining whether the data requirement is met comprises:

performing point to point correlation of each additional input with information corresponding to each diagnosis code of the plurality of diagnosis codes; and performing a contextual analysis of each additional input to correlate each additional input with the information corresponding to each diagnosis code of the plurality of diagnosis codes.

15. A method for controlling elements of a graphical user interface (GUI) for a medical data entry system, said method comprising:

providing a processing device configured to display information to and receive input from a user;

iteratively receiving, at the processing device, one or more inputs from the GUI until identification of a diagnosis code from among a plurality of diagnosis codes that corresponds to a clinical concept, wherein a plurality of different inputs are received during each iteration;

determining, at the processing device, whether a data requirement is met to associate the clinical concept with the diagnosis code by comparing the plurality of different inputs received during each iteration against the plurality of diagnosis codes;

in response to determining that the data requirement is not met:

generating, by the processing device, one or more GUI elements including one or more graphical indicators configured to collect additional inputs, the additional inputs used to determine whether the data requirement is met;

in response to determining that the data requirement is met:

designating, by the processing device, the diagnosis code as a fully specified diagnosis code; and updating the one or more graphical indicators to present a selectable data item, the selectable data item corresponding to the data requirement, the second GUI element configured to indicate whether the data requirement is met;

determining at the processing device, in response to the selection of the selectable data item, whether the data requirement has been met to associate the clinical concept with the diagnosis code, wherein determining whether the data requirement is met to associate the clinical concept with the diagnosis code comprises iteratively obtaining additional inputs associated with the clinical concept until a stop condition is met; and evaluating each of the additional inputs against the plurality of diagnosis codes;

in evaluating each of the additional inputs against the plurality of diagnosis codes, excluding one or more of the plurality of diagnosis codes from the evaluating each of the additional inputs based on the additional inputs;

designating the stop condition as met upon identification of the diagnosis code from the plurality of diagnosis codes that corresponds to the clinical concept and is identified based on the additional inputs;

configuring the second GUI element based on determining, in response to the selection of the selectable data item, to one of a first state indicating the data requirement has not been met and a second state indicating the data requirement has been met;

executing, in response to determining that the data requirement has not been met, a GUI control adapted to require a user to positively or negatively select the selectable data item such that the data requirement is met to associate the clinical concept with the diagnosis code;

wherein executing the GUI control includes activating a graphical indicator on the second GUI element indicating that the data requirement has not been met;

providing a feedback report to the user in response to receipt of a selection of the selectable data item;

wherein the feedback report identifies a deficiency in received data to generate the fully specified diagnosis code;

designating the diagnosis code as the fully specified diagnosis code in response to determining that the data requirement has been met; and updating the graphical indicator to display an indication that the data requirement has been met to designate the diagnosis code as the fully specified diagnosis code.

16. The method of claim 15, further comprising:

providing a feedback report to the user, wherein the feedback report identifies any deficiencies in data to generate a fully specified diagnosis code.

17. The method of claim 15, wherein at least some of the additional inputs are unrelated to generation of a diagnosis but are related to associating the clinical concept with the diagnosis code.

18. The method of claim 15, wherein the plurality of diagnosis codes correspond to payer codes.

19. The method of claim 15, further comprising evaluating the inputs by excluding one or more diagnosis codes of the plurality of diagnosis codes from consideration during each iteration based on the plurality of different inputs.

20. The method of claim 15, further comprising:

backfilling entries in an examination history based on the one or more inputs and the plurality of different inputs within the GUI; and carrying one or more of the inputs forward as additional sections of the GUI are presented.

21. The method of claim 15, further comprising:

indicating, in response to the one or more inputs and the plurality of different inputs, that the data requirement has been met by removing highlighting from items rendered on the GUI.

22. The method of claim 15, wherein determining whether the data requirement is met further comprises:

performing point to point correlation of each input with information corresponding to each diagnosis code of the plurality of diagnosis codes; and performing a contextual analysis of each input to correlate each input with the information corresponding to each diagnosis code of the plurality of diagnosis codes.

23. A system for aiding and guiding a practitioner in creation of a fully specified diagnosis code by controlling elements of a graphical user interface (GUI) for a medical data entry system, comprising:

a processing device configured to display information to and receive input from a user, wherein the processing device further configured to receive an input relating to a clinical concept;

wherein the clinical concept is associated with a diagnosis code; and wherein the diagnosis code is associated with a data requirement;

wherein the processing device further configured to determine, in receipt of the input, whether the data requirement is met to associate the clinical concept with the diagnosis code;

wherein the processing device further configured to designate the diagnosis code as a fully specified diagnosis code when the data requirement is met;

wherein the processing device further configured to generate, in response to receiving the input and in response to determining that the data requirement is not met to associate the clinical concept with the diagnosis code, a second GUI element on the processing device configured to present a selectable data item adapted to include a positive selection state and a negative selection state, the selectable data item corresponding to the data requirement, the second GUI element configured to indicate whether the data requirement is met;

wherein the processing device further configured to determine, in response to the selection of the selectable data item, whether the data requirement has been met to associate the clinical concept with the diagnosis code, wherein determining whether the data requirement is met to associate the clinical concept with the diagnosis code comprises iteratively obtaining additional inputs associated with the clinical concept until a stop condition is met; and wherein the processing device further configured to evaluate each of the additional inputs against a plurality of diagnosis codes;

wherein the processing device further configured to exclude one or more of the plurality of diagnosis codes from the evaluating each of the additional inputs step based on the additional inputs;

wherein the processing device further configured to designate the stop condition as met upon identification of the diagnosis code from the plurality of diagnosis codes that corresponds to the clinical concept and is identified based on the additional inputs;

configuring the second GUI element based on determining, in response to the selection of the selectable data item, to one of a first state indicating the data requirement has not been met and a second state indicating the data requirement has been met;

wherein the processing device further configured to execute, in response to determining that the data requirement has not been met, a GUI control adapted to require a user to positively or negatively select the selectable data item such that the data requirement is met to associate the clinical concept with the diagnosis code;

wherein executing the GUI control includes activating a graphical indicator on the second GUI element indicating that the data requirement has not been met;

wherein the processing device further configured to provide a feedback report to the user in response to receipt of a selection of the selectable data item;

wherein the feedback report identifies a deficiency in received data to generate the fully specified diagnosis code;

wherein the processing device further configured to designate the diagnosis code as the fully specified diagnosis code in response to determining that the data requirement has been met; and wherein the processing device further configured to update the graphical indicator to display an indication that the data requirement has been met to designate the diagnosis code as the fully specified diagnosis code.

24. The system of claim 23, wherein at least some of the additional inputs are unrelated to generation of a diagnosis but are related to associating the clinical concept with the diagnosis code.

25. The system of claim 23, wherein the plurality of diagnosis codes correspond to payer codes.

26. The system of claim 23, wherein the processing device is further configured to:

backfill entries in an examination history based on the one or more inputs within the GUI; and carrying one or more of the inputs forward as additional sections of the GUI are presented.

27. The system of claim 23, wherein the processing device is further configured to:

indicate, in response to the one or more inputs, that the data requirement has been met by removing highlighting from items rendered on the GUI.

28. The system of claim 23, wherein the processing device determines whether the data requirement is met by:

performing point to point correlation of each input with information corresponding to each diagnosis code of the plurality of diagnosis codes; and performing a contextual analysis of each input to correlate each input with the information corresponding to each diagnosis code of the plurality of diagnosis codes.

* * * * *